US011140902B2

(12) United States Patent
Bonning et al.

(10) Patent No.: US 11,140,902 B2
(45) Date of Patent: Oct. 12, 2021

(54) INSECT TOXIN DELIVERY MEDIATED BY A DENSOVIRUS COAT PROTEIN

(71) Applicants: University of Florida Research Foundation, Inc., Gainesville, FL (US); Iowa State University Research Foundation, Inc., Ames, IA (US)

(72) Inventors: Bryony C. Bonning, Gainesville, FL (US); Mariah Kemmerer, Gainesville, FL (US)

(73) Assignees: University of Florida Research Foundation, Inc., Gainesville, FL (US); Iowa State University Research Foundation, Inc., Ames, IA (US)

( * ) Notice: Subject to any disclaimer, the term of this patent is extended or adjusted under 35 U.S.C. 154(b) by 27 days.

(21) Appl. No.: 16/336,789

(22) PCT Filed: Sep. 27, 2017

(86) PCT No.: PCT/IB2017/055903
§ 371 (c)(1),
(2) Date: Mar. 26, 2019

(87) PCT Pub. No.: WO2018/060881
PCT Pub. Date: Apr. 5, 2018

(65) Prior Publication Data
US 2019/0239513 A1    Aug. 8, 2019

Related U.S. Application Data

(60) Provisional application No. 62/400,381, filed on Sep. 27, 2016.

(51) Int. Cl.
| *A01N 63/00* | (2020.01) |
| *C07K 14/435* | (2006.01) |
| *C07K 14/005* | (2006.01) |
| *A01N 37/46* | (2006.01) |
| *A01N 25/06* | (2006.01) |
| *C07K 14/015* | (2006.01) |
| *C12N 7/00* | (2006.01) |
| *C12N 15/86* | (2006.01) |
| *C12N 15/85* | (2006.01) |

(52) U.S. Cl.
CPC .......... *A01N 63/00* (2013.01); *A01N 25/06* (2013.01); *A01N 37/46* (2013.01); *C07K 14/005* (2013.01); *C07K 14/015* (2013.01); *C07K 14/43563* (2013.01); *C12N 7/00* (2013.01); *C12N 15/86* (2013.01); *C07K 2319/55* (2013.01); *C12N 2015/8518* (2013.01); *C12N 2750/14022* (2013.01); *C12N 2750/14031* (2013.01)

(58) Field of Classification Search
None
See application file for complete search history.

(56) References Cited

U.S. PATENT DOCUMENTS

| 4,458,066 A | 7/1984 | Caruthers et al. |
| 4,658,082 A | 4/1987 | Simpson et al. |
| 4,945,050 A | 7/1990 | Sanford et al. |
| 5,262,306 A | 11/1993 | Robeson et al. |
| 5,268,463 A | 12/1993 | Jefferson |
| 5,366,892 A | 11/1994 | Foncerrada et al. |
| 5,583,210 A | 12/1996 | Neill et al. |
| 5,593,881 A | 1/1997 | Thompson et al. |
| 5,599,670 A | 2/1997 | Jefferson |
| 5,602,321 A | 2/1997 | John |
| 5,643,776 A | 7/1997 | Hammock et al. |
| 5,674,747 A | 10/1997 | Hammock et al. |
| 5,683,439 A | 11/1997 | Jensen |
| 5,693,512 A | 12/1997 | Finer et al. |
| 5,703,049 A | 12/1997 | Rao |
| 5,723,756 A | 3/1998 | Peferoen et al. |
| 5,736,369 A | 4/1998 | Bowen et al. |
| 5,736,514 A | 4/1998 | Iizuka et al. |
| 5,747,450 A | 5/1998 | Ohba et al. |
| 5,792,931 A | 8/1998 | Duvick et al. |
| 5,850,016 A | 12/1998 | Jung et al. |
| 5,885,801 A | 3/1999 | Rao |
| 5,885,802 A | 3/1999 | Rao |
| 5,952,544 A | 9/1999 | Browse et al. |
| 5,981,840 A | 11/1999 | Zhao et al. |
| 5,990,389 A | 11/1999 | Rao et al. |

(Continued)

FOREIGN PATENT DOCUMENTS

| EP | 604662 A1 | 7/1994 |
| EP | 672752 A1 | 9/1995 |

(Continued)

OTHER PUBLICATIONS

Abd-Alla et al., NS-3 protein of the Junonia coenia densovirus is essential for viral DNA replication in an Ld 652 cell line and Spodoptera littoralis larvae, *J. Virol.* 78:790-7 (2004).

Amoah et al., Factors influencing Agrobacterium-mediated transient expression of uidA in wheat inflorescence tissue, *J. Exp. Bot.* 52:1135-42 (2001).

An et al., Functional analysis of the 3' control region of the potato wound-inducible proteinase inhibitor II gene, *Plant Cell.* 1:115-22 (1989).

Atanassova et al., A 126 bp fragment of a plant histone gene promoter confers preferential expression in meristems of transgenic *Arabidopsis, Plant J.* 2:291-300 (1992).

(Continued)

*Primary Examiner* — Anand U Desai
(74) *Attorney, Agent, or Firm* — Marshall, Gerstein & Borun LLP

(57) ABSTRACT

A coat protein of *Junonia coenia* densovirus (JcDNV) is used to deliver attached peptide insect toxin across the gut epithelium of a fall armyworm, *Spodoptera frugiperda*. A fusion protein comprising VP4 attached to an insect toxin via a peptide linker is developed. A composition comprising a JcDNV coat protein attached to an insect toxin via a peptide linker can be used for insect pest control.

13 Claims, 12 Drawing Sheets

Specification includes a Sequence Listing.

(56) References Cited

U.S. PATENT DOCUMENTS

| | | |
|---|---|---|
| 6,232,529 B1 | 5/2001 | Singletary et al. |
| 6,300,543 B1 | 10/2001 | Cass et al. |
| 6,673,340 B1 | 1/2004 | Harrison et al. |
| 7,312,080 B2 | 12/2007 | Miller et al. |
| 7,547,677 B2 | 6/2009 | Bonning et al. |
| 2011/0167517 A1 | 7/2011 | Danilevskaya et al. |
| 2013/0097729 A1 | 4/2013 | Bonning et al. |
| 2014/0142164 A1* | 5/2014 | Ogliastro ......... C07K 14/43522 514/44 R |

FOREIGN PATENT DOCUMENTS

| | | |
|---|---|---|
| WO | WO-1991/10725 A1 | 7/1991 |
| WO | WO-1994/11516 A1 | 5/1994 |
| WO | WO-1996/19256 A1 | 6/1996 |
| WO | WO-1996/30530 A1 | 10/1996 |
| WO | WO-1998/20122 A1 | 5/1998 |
| WO | WO-1998/20133 A2 | 5/1998 |
| WO | WO-1999/25821 A1 | 5/1999 |
| WO | WO-1999/61619 A2 | 12/1999 |
| WO | WO-2000/17364 A2 | 3/2000 |

OTHER PUBLICATIONS

Baim et al., A chimeric mammalian transactivator based on the lac repressor that is regulated by temperature and isopropyl beta-D-thiogalactopyranoside, *Proc. Natl. Acad. Sci. USA.* 88:5072-6 (1991).

Bao et al., Transfection of a reporter plasmid into cultured cells by sonoporation in vitro, *Ultrasound Med. Biol.* 23:953-9 (1997).

Bevan et al., Structure and transcription of the nopaline synthase gene region of T-DNA, *Nucleic Acids Res.* 11:369-85 (1983).

Bolte et al., The N-myristoylated Rab-GTPase m-Rabmc is involved in post-Golgi trafficking events to the lytic vacuole in plant cells, *J. Cell. Sci.* 117:943-54 (2004).

Bonning et al., Delivery of intrahemocoelic peptides for insect pest management., *Trends Biotechnol.* 32:91-8 (2014).

Bonning et al., Toxin delivery by the coat protein of an aphid-vectored plant virus provides plant resistance to aphids, *Nat. Biotechnol.* 32:102-5 (2014).

Bossin et al., Junonia coenia densovirus-based vectors for stable transgene expression in Sf9 cells: influence of the densovirus sequences on genomic integration, *J. Virol.* 77:11060-71 (2003).

Brown et al., Chemical synthesis and cloning of a tyrosine tRNA gene, *Methods Enzymol.* 68:109-51 (1979).

Bruemmer et al., Structure of an insect parvovirus (Junonia coenia Densovirus) determined by cryo-electron microscopy, *J. Mol. Biol.* 347:791-801 (2005).

Buchman et al., Comparison of intron-dependent and intron-independent gene expression, *Mol. Cell Biol.* 8:4395-405 (1988).

Bytebier et al., T-DNA organization in tumor cultures and transgenic plants of the monocotyledon Asparagus officinalis, *Proc. Natl. Acad. Sci. USA.* 84:5345-9 (1987).

Callis et al., Introns increase gene expression in cultured maize cells, *Genes Dev.* 1:1183-200 (1987).

Casartelli et al., A megalin-like receptor is involved in protein endocytosis in the midgut of an insect (Bombyx mori, Lepidoptera), *Am. J. Physiol. Regul. Integr. Comp. Physiol.* R1290-300 (2008).

Casartelli et al., Absorption of albumin by the midgut of a lepidopteran larva, *J. Insect. Physiol.* 51:933-40 (2005).

Cermenati et al., A morphological and functional characterization of Bombyx mori larval midgut cells in culture, *Invertebr. Survival.* 4:119-26 (2007).

Cermenati et al., The CPP Tat enhances eGFP cell internalization and transepithelial transport by the larval midgut of Bombyx mori (Lepidoptera, Bombycidae), *J. Insect. Physiol.* 57:1689-97 (2011).

Chiu et al., Engineered GFP as a vital reporter in plants, *Curr. Biol.* 6:325-30 (1996).

Christou et al., Stable Transformation of Soybean Callus by DNA-Coated Gold Particles, *Plant Physiol.* 87:671-4 (1988).

Dahlman et al., A teratocyte gene from a parasitic wasp that is associated with inhibition of insect growth and development inhibits host protein synthesis, *Insect Mol. Biol.* 12:527-34 (2003).

Datta et al.,Genetically engineered fertile indica-rice recovered from protoplasts, *Biotechnology.* 8:736-40 (1990).

De Wet et al., Firefly luciferase gene: structure and expression in mammalian cells, *Mol. Cell. Biol.* 7:725-37 (1987).

Degenkolb et al., Structural requirements of tetracycline-Tet repressor interaction: determination of equilibrium binding constants for tetracycline analogs with the Tet repressor, *Antimicrob. Agents Chemother.* 35:1591-5 (1991).

Deshayes et al., Liposome-mediated transformation of tobacco mesophyll protoplasts by an *Escherichia coli* plasmid, *EMBO J.* 4:2731-7 (1985).

Deuschle et al., Regulated expression of foreign genes in mammalian cells under the control of coliphage T3 RNA polymerase and lac repressor, *Proc. Natl. Acad. Sci. USA.* 86:5400-4 (1989).

Deuschle et al., RNA polymerase II transcription blocked by *Escherichia coli* lac repressor, *Science.* 248:480-3 (1990).

Devereux et al., A comprehensive set of sequence analysis programs for the VAX, *Nucleic Acids Res.* 12:387-95 (1984).

Dratewka-Kos et al., Polypeptide structure of germin as deduced from cDNA sequencing, *J. Biol. Chem.* 264:4896-900 (1989).

Drummond et al., The effect of capping and polyadenylation on the stability, movement and translation of synthetic messenger RNAs in Xenopus oocytes, *Nucleic Acids Res.* 13:7375-94 (1985).

Ffrench et al., Insecticidal toxins from Photorhabdus bacteria and their potential use in agriculture, *Toxicon.* 49:436-51 (2007).

Ffrench-Constant et al., Does resistance really carry a fitness cost?, *Curr. Opin. Insect Sci.* 21:39-46 (2017).

Fiandra et al., The intestinal barrier in lepidopteran larvae: permeability of the peritrophic membrane and of the midgut epithelium to two biologically active peptides, *J. Insect Physiol.* 55:10-8 (2009).

Figge et al., Stringent regulation of stably integrated chloramphenicol acetyl transferase genes by *E. coli* lac repressor in monkey cells, *Cell.* 52:713-22 (1988).

Finer et al., Use of Agrobacterium expressing green fluorescent protein to evaluate colonization of sonication-assisted Agrobacterium-mediated transformation-treated soybean cotyledons, *Lett. Appl. Microbiol.* 30:406-10 (2000).

Fitches et al., In vitro and in vivo binding of snowdrop (Galanthus nivalis agglutinin; GNA) and jackbean (Canavalia ensiformis; Con A) lectins within tomato moth (Lacanobia olercea) larvae; mechanism of insecticidal action, *J. Insect. Physiol.* 47:777-87 (2001).

Fuerst et al., Transfer of the inducible lac repressor/operator system from *Escherichia coli* to a vaccinia virus expression vector, *Proc. Natl. Acad. Sci. USA.* 86:2549-53 (1989).

Gade, Regulation of intermediary metabolism and water balance of insects by neuropeptides, *Annu. Rev. Entomol.* 49:93-113 (2004).

Goff et al., Transactivation of anthocyanin biosynthetic genes following transfer of B regulatory genes into maize tissues, *EMBO J.* 9:2517-22 (1990).

Gordon-Kamm et al., Transformation of maize cells and regeneration of fertile transgenic plants, *Plant Cell.* 2:603-18 (1990).

International Preliminary Report on Patentability, PCT/IB2017/055903 (dated Apr. 2, 2019).

International Search Report and Written Opinion, PCT/IB2017/055903 (dated Dec. 22, 2017).

Ishida et al., High efficiency transformation of maize (*Zea mays* L.) mediated by Agrobacterium tumefaciens, *Nat. Biotechnol.* 14:745-50 (1996).

Ishizuka et al., Putrescine oxidase of Micrococcus rubens: primary structure and *Escherichia coli, J. Gen. Microbiol.* 139:425-32 (1993).

Jeffers et al., The movement of proteins across the insect and tick digestive system, *J. Insect. Physiol.* 54:319-32 (2008).

Jones et al., Isolation of the tomato Cf-9 gene for resistance to Cladosporium fulvum by transposon tagging, *Science.* 266:789-93 (1994).

Kaeppler et al., Silicon carbide fiber-mediated DNA delivery into plant cells, *Plant Cell Rep.* 9:415-8 (1990).

Kaeppler et al., Silicon carbide fiber-mediated stable transformation of plant cells, *Theor. Appl. Genet.* 84:560-6 (1992).

(56) References Cited

OTHER PUBLICATIONS

Kato et al., Spectral profiling for the simultaneous observation of four distinct fluorescent proteins and detecction of protein-protein interaction via flouorescence resonance energy transfer in tobacco leag nuclei, *Plant Physiol.* 129:931-42 (2002).
Keil et al., Primary structure of a proteinase inhibitor II gene from potato (Solanum tuberosum), *Nucleic Acids Res.* 14:5641-50 (1986).
Kemmerer et al., Transcytosis of Junonia coenia densovirus VP4 across the gut epithelium of Spodoptera frugiperda (Lepidoptera: Noctuidae), *Insect Science.* 27:22-32 (2018).
Labow et al., Conversion of the lac repressor into an allosterically regulated transcriptional activator for mammalian cells, *Mol. Cell Biol.* 10:3343-56 (1990).
Li et al., An improved rice transformation system using the biolistic method, *Plant Cell Rep.* 12:250-5 (1993).
Martin et al., Map-based cloning of a protein kinase gene conferring disease resistance in tomato, *Science.* 262:1432-6 (1993).
Masumura et al., cDNA cloning of an mRNA encoding a sulfur-rich 10 kDa prolamin polypeptide in rice seeds, *Plant Mol. Biol.* 12:123-30 (1989).
Matsuoka et al., Propeptide of a precursor to a plant vacuolar protein required for vacuolar targeting, *Proc. Natl. Acad. Sci. USA.* 88:834-8 (1991).
McCabe et al., Stable transformation of soybean (Glycine max) by practice acceleration, *Biotechnology.* 6:923-6 (1988).
McElroy et al., Isolation of an efficient actin promoter for use in rice transformation, *Plant Mol. Biol.* 163-71 (1990).
Meyers et al., Optimal alignments in linear space, *Comput Appl. Biosci.* 4:11-7 (1988).
Miki et al., Procedure for Introducing Foreign DNA into Plants, Methods in Plant Molecular Biology and Biotechnology, CRC Press, Inc., Boca Raton, pp. 67-88 (1993).
Mindrinos et al., The *A. thaliana* disease resistance gene RPS2 encodes a protein containing a nucleotide-binding site and leucine-rich repeats, *Cell.* 78:1089-99 (1994).
Mogen et al., Upstream sequences other than AAUAAA are required for efficient messenger RNA 3'-end formation in plants, *Plant Cell.* 2:1261-72 (1990).
Moloney et al., High efficiency transformation of Brassica napus using Agrobacterium vectors, *Plant Cell Reports.* 8:238-42 (1989).
Mosbach et al., Formation of proinsulin by immobilized Bacillus subtilis, *Nature.* 302:543-5 (1983).
Muesing et al., Regulation of mRNA accumulation by a human immunodeficiency virus trans-activator protein, *Cell.* 48:691-701 (1987).
Mukherjee et al., Orally active acaricidal peptide toxins from spider venom, *Toxicon.* 47:182-7 (2006).
Murray et al., Codon usage in plant genes, *Nucleic Acids Res.* 17:477-98 (1989).
Narang et al., Improved phosphotriester method for the synthesis of gene fragments, *Meth. Enzymol.* 68:90-98 (1979).
NCBI Accession No. AFN61295.1, omega-Hv1a/GNA FP5 insecticidal fusion protein, partial [synthetic construct], Jul. 18, 2012.
NCBI Accession No. AGO32183.1, omega-Hv1a/GNA FP5 insecticidal fusion protein, partial [synthetic construct], Aug. 14, 2013.

NCBI Accession No. NP_694823.1, hypothetical protein [Junonia coenia densovirus], Aug. 13, 2018.
Needham-VanDevanter et al., Characterization of an adduct between CC-1065 and a defined oligodeoxynucleotide duplex, *Nucleic Acids Res.* 12:6159-68 (1984).
Odell et al., Identification of DNA sequences required for activity of the cauliflower mosaic virus 35S promoter, *Nature.* 313:810-2 (1985).
Oliva et al., Evidence that tetracycline analogs whose primary target is not the bacterial ribosome cause lysis of *Escherichia coli.,* *Antimicrob. Agents Chemother.* 36:913-9 (1992).
Paszkowski et al., Direct gene transfer to plants, *EMBO J.* 3:2712-22 (1984).
Reznikoff, The lactose operon-controlling elements: a complex paradigm, *Mol. Microbiol.* 6:2419-22.
Riggs et al., Stable transformation of tobacco by electroporation: evidence for plasmid concatenation, *Proc. Natl. Acad. Sci. USA.* 83:5602-6 (1986).
Sanahuja et al., Bacillus thuringiensis: a century of research, development and commercial applications, *Plant Biotechnol.* 9:283-300 (2011).
Schneider, Cell lines derived from late embryonic stages of *Drosophila melanogaster,* *J. Embryol. Exp. Morphol.* 27:353-65 (1972).
Schoofs et al., Ecdysiostatins and allatostatins in Schistocerca gregaria, *Ann. NY. Acad. Sci.* 839:301-5 (1998).
Schubert et al., Cloning of the Alcaligenes eutrophus genes for synthesis of poly-beta-hydroxybutyric acid (PHB) and synthesis of PHB in *Escherichia coli, J. Bacteriol.* 170:5837-47 (1988).
Shahin et al., Totipotency of tomato protoplasts, *Theor. Appl. Genet.* 69:235-40 (1985).
Su et al., High-level secretion of functional green fluorescent protein from transgenic tobacco cell cultures: characterization and sensing, *Biotechnol. Bioeng.* 85:610-9 (2004).
Tedford et al., Functional significance of the beta hairpin in the insecticidal neurotoxin omega-atracotoxin-Hv1a, *J. Biol Chem.* 276:26568-76 (2001).
Tomes et al., "Direct DNA Transfer Into Intact Plant Cells via Microprojectile Bombardment," Plant Cell, Tissue and Organ Culture, Fundamental Methods, Berlin Heidelberg New York, pp. 197-213 (1995).
Tuma et al., Transcytosis: crossing cellular barriers, *Physiol. Rev.* 83:871-932 (2003).
Van Damme et al., Molecular cloning of mannose-binding lectins from Olivia miniata, *Plant Mol. Biol.* 24:825-30 (1994).
Wang et al., Densovirus crosses the insect midgut by transcytosis and disturbs the epithelial barrier function, *J. Virol.* 87:12380-91 (2013).
Windley et al., Spider-venom peptides as bioinsecticides, *Toxins (Basel).* 4:191-227 (2012).
Wolfsberger et al., Preparation and partial characterization of amino acid transporting brush border membrane vesicles from the larval midgut of the gypsy moth (Lymantria dispar), *Arch. Insect. Biochem. Physiol.* 24:139-47 (1993).
Yao et al., *Drosophila* ultraspiracle modulates ecdysone receptor function via heterodimer formation, *Cell.* 71:63-72 (1992).
Yarranton, Inducible vectors for expression in mammalian cells, *Curr. Opin. Biotechnol.* 3:506-11 (1992).

\* cited by examiner

FIG. 1

Scorpion - *Androctonus australis* Hector insect toxin

AaHIT

FIG. 5

Scorpion, *Leiurus quinquestriatus hebraeus*

LqHIT2

SEQUENCE LISTING

```
<160> NUMBER OF SEQ ID NOS: 16

<210> SEQ ID NO 1
<211> LENGTH: 810
<212> TYPE: PRT
<213> ORGANISM: Junonia coenia densovirus
<220> FEATURE:
<221> NAME/KEY: misc_feature
<222> LOCATION: (368)..(368)
<223> OTHER INFORMATION: Xaa can be any naturally occurring amino acid

<400> SEQUENCE: 1

Met Ser Phe Tyr Thr Ala Gly Leu Ile His Arg Ala Arg Pro Gly Tyr
1               5                   10                  15

Arg Ile Ile Pro Glu Ser Thr Ala Thr Glu Asp Ile Glu Leu Gly Ala
            20                  25                  30

Ile Gly Glu Glu Thr Pro Leu Leu Ser Glu Gly Ala Val Thr Ala Val
        35                  40                  45

Glu Glu Ser Ala Ala Val Gly Leu Pro Glu Leu Gly Ala Gly Leu Ala
    50                  55                  60

Gly Ala Ile Gly Thr His Ala Asp Val Leu Tyr Arg Asn Arg Asn Val
65                  70                  75                  80

Phe Lys Ser Val Leu Thr Gly Asn Tyr Thr Asp Leu Lys Gly Asn Pro
                85                  90                  95

Leu Lys Gln Arg Asn Ala Ile Ser Glu Lys Thr Lys Gln Leu Gly Arg
            100                 105                 110

Gly Ile Phe Gln Gly Asp Phe Asn Arg Ala Phe Pro Asp Asp Leu Lys
        115                 120                 125

Leu Glu Thr Glu Gln Glu Lys Lys Asp Leu Leu Arg Tyr Tyr Asn His
    130                 135                 140

Asn Arg Arg Leu Ala Gly Leu Ser Glu Ala Tyr Pro Gln Gly Lys Gly
145                 150                 155                 160

Tyr Ala Tyr Ala Lys Ser Gln Lys Val Leu Glu Ala Glu Arg Arg Gly
                165                 170                 175

Leu Thr Val Pro Gly Tyr Lys Tyr Leu Gly Pro Gly Asn Ser Leu Asn
            180                 185                 190

Arg Gly Gln Pro Thr Asn Gln Ile Asp Glu Asp Ala Lys Glu His Asp
        195                 200                 205

Glu Ala Tyr Asp Lys Ala Lys Thr Ser Gln Glu Val Ser Gln Ala Asp
    210                 215                 220
```

-continued

Asn Thr Phe Val Asn Lys Ala Leu Asp His Ile Val Asn Ala Ile Asn
225                 230                 235                 240

Leu Lys Glu Thr Pro Gly Asn Ala Phe Gly Ala Ile Gly Ala Ile
            245                 250                 255

Gly Ile Gly Thr Lys Gln Ala Ile Glu Lys His Ser Gly Val Ile Tyr
            260                 265                 270

Pro Ser Val Ser Gly Met Ser Arg Gln Ile Asn Ser Lys Tyr Leu Asn
            275                 280                 285

Ser Trp His Asp Trp Ile Glu Gln Asn Lys His Asn Asn Phe Glu Gly
            290                 295                 300

Ile Gln Leu Pro Glu Asp Phe Tyr Thr Glu Gln Thr Leu Ser Asp
305                 310                 315                 320

Ser Pro Met Ser Glu Gly Thr Lys Arg Lys Ala Asp Thr Pro Val Glu
            325                 330                 335

Glu Gly Pro Ser Lys Lys Gly Ala His Asn Ala Pro His Asn Ser Gln
            340                 345                 350

Gly Thr Asp Pro Gln Asn Pro Ser Ser Gly Ala Thr Thr Ser Xaa
            355                 360                 365

Asp Val Glu Met Ala Met Ser Leu Pro Gly Thr Gly Ser Gly Thr Ser
370                 375                 380

Ser Gly Gly Asn Thr Ser Gly Gln Glu Val Tyr Val Ile Pro Arg
385                 390                 395                 400

Pro Phe Ser Asn Phe Gly Lys Lys Leu Ser Thr Tyr Thr Lys Ser His
            405                 410                 415

Lys Phe Met Ile Phe Gly Leu Ala Asn Asn Val Ile Gly Pro Thr Gly
            420                 425                 430

Thr Gly Thr Thr Ala Val Asn Arg Leu Ile Thr Thr Cys Leu Ala Glu
            435                 440                 445

Ile Pro Trp Gln Lys Leu Pro Leu Tyr Met Asn Gln Ser Glu Phe Asp
450                 455                 460

Leu Leu Pro Pro Gly Ser Arg Val Val Glu Cys Asn Val Lys Val Ile
465                 470                 475                 480

Phe Arg Thr Asn Arg Ile Ala Phe Glu Thr Ser Ser Thr Ala Thr Lys
            485                 490                 495

Gln Ala Thr Leu Asn Gln Ile Ser Asn Leu Gln Thr Ala Val Gly Leu
            500                 505                 510

Asn Lys Leu Gly Trp Gly Ile Asp Arg Ser Phe Thr Ala Phe Gln Ser
            515                 520                 525

Asp Gln Pro Met Ile Pro Thr Ala Thr Ser Ala Pro Lys Tyr Glu Pro
530                 535                 540

Ile Thr Gly Thr Thr Gly Tyr Arg Gly Met Ile Ala Asp Tyr Tyr Gly
545                 550                 555                 560

Ala Asp Ser Thr Asn Asp Ala Ala Phe Gly Asn Ala Gly Asn Tyr Pro
            565                 570                 575

His His Gln Val Gly Ser Phe Thr Phe Ile Gln Asn Tyr Tyr Cys Met
            580                 585                 590

Tyr Gln Gln Thr Asn Gln Gly Thr Gly Gly Trp Pro Cys Leu Ala Glu
            595                 600                 605

His Leu Gln Gln Phe Asp Ser Lys Thr Val Asn Asn Gln Cys Leu Ile
            610                 615                 620

Asp Val Thr Tyr Lys Pro Lys Met Gly Leu Ile Lys Pro Pro Leu Asn
625                 630                 635                 640

```
Tyr Lys Ile Ile Gly Gln Pro Thr Ala Lys Gly Thr Ile Ser Val Gly
            645                 650                 655
Asp Asn Leu Val Asn Met Arg Gly Ala Val Ile Asn Pro Pro Glu
        660                 665                 670
Ala Thr Gln Ser Val Thr Glu Ser Thr His Asn Leu Thr Arg Asn Phe
        675                 680                 685
Pro Ala Asn Leu Phe Asn Ile Tyr Ser Asp Ile Glu Lys Ser Gln Ile
        690                 695                 700
Leu His Lys Gly Pro Trp Gly His Glu Asn Pro Gln Ile Gln Pro Ser
705                 710                 715                 720
Val His Ile Gly Ile Gln Ala Val Pro Ala Leu Thr Thr Gly Ala Leu
            725                 730                 735
Leu Val Asn Ser Ser Pro Leu Asn Ser Trp Thr Asp Ser Met Gly Tyr
            740                 745                 750
Ile Asp Val Met Ser Ser Cys Thr Val Met Glu Ser Gln Pro Thr His
            755                 760                 765
Phe Pro Phe Ser Thr Asp Ala Asn Thr Asn Pro Gly Asn Thr Ile Tyr
        770                 775                 780
Arg Ile Asn Leu Thr Pro Asn Ser Leu Thr Ser Ala Phe Asn Gly Leu
785                 790                 795                 800
Tyr Gly Asn Gly Ala Thr Leu Gly Asn Val
            805                 810

<210> SEQ ID NO 2
<211> LENGTH: 437
<212> TYPE: PRT
<213> ORGANISM: Junonia coenia densovirus

<400> SEQUENCE: 2

Met Ser Leu Pro Gly Thr Gly Ser Gly Thr Ser Ser Gly Gly Gly Asn
1               5                   10                  15
Thr Ser Gly Gln Glu Val Tyr Val Ile Pro Arg Pro Phe Ser Asn Phe
            20                  25                  30
Gly Lys Lys Leu Ser Thr Tyr Thr Lys Ser His Lys Phe Met Ile Phe
        35                  40                  45
Gly Leu Ala Asn Asn Val Ile Gly Pro Thr Gly Thr Gly Thr Thr Ala
    50                  55                  60
Val Asn Arg Leu Ile Thr Thr Cys Leu Ala Glu Ile Pro Trp Gln Lys
65                  70                  75                  80
Leu Pro Leu Tyr Met Asn Gln Ser Glu Phe Asp Leu Leu Pro Pro Gly
                85                  90                  95
Ser Arg Val Val Glu Cys Asn Val Lys Val Ile Phe Arg Thr Asn Arg
            100                 105                 110
Ile Ala Phe Glu Thr Ser Ser Thr Ala Thr Lys Gln Ala Thr Leu Asn
        115                 120                 125
Gln Ile Ser Asn Leu Gln Thr Ala Val Gly Leu Asn Lys Leu Gly Trp
    130                 135                 140
Gly Ile Asp Arg Ser Phe Thr Ala Phe Gln Ser Asp Gln Pro Met Ile
145                 150                 155                 160
Pro Thr Ala Thr Ser Ala Pro Lys Tyr Glu Pro Ile Thr Gly Thr Thr
                165                 170                 175
Gly Tyr Arg Gly Met Ile Ala Asp Tyr Gly Ala Asp Ser Thr Asn
            180                 185                 190
Asp Ala Ala Phe Gly Asn Ala Gly Asn Tyr Pro His His Gln Val Gly
        195                 200                 205
```

Ser Phe Thr Phe Ile Gln Asn Tyr Tyr Cys Met Tyr Gln Gln Thr Asn
          210                 215                 220

Gln Gly Thr Gly Gly Trp Pro Cys Leu Ala Glu His Leu Gln Gln Phe
225                 230                 235                 240

Asp Ser Lys Thr Val Asn Asn Gln Cys Leu Ile Asp Val Thr Tyr Lys
            245                 250                 255

Pro Lys Met Gly Leu Ile Lys Pro Pro Leu Asn Tyr Lys Ile Ile Gly
            260                 265                 270

Gln Pro Thr Ala Lys Gly Thr Ile Ser Val Gly Asp Asn Leu Val Asn
            275                 280                 285

Met Arg Gly Ala Val Val Ile Asn Pro Pro Glu Ala Thr Gln Ser Val
            290                 295                 300

Thr Glu Ser Thr His Asn Leu Thr Arg Asn Phe Pro Ala Asn Leu Phe
305                 310                 315                 320

Asn Ile Tyr Ser Asp Ile Glu Lys Ser Gln Ile Leu His Lys Gly Pro
            325                 330                 335

Trp Gly His Glu Asn Pro Gln Ile Gln Pro Ser Val His Ile Gly Ile
            340                 345                 350

Gln Ala Val Pro Ala Leu Thr Thr Gly Ala Leu Leu Val Asn Ser Ser
            355                 360                 365

Pro Leu Asn Ser Trp Thr Asp Ser Met Gly Tyr Ile Asp Val Met Ser
370                 375                 380

Ser Cys Thr Val Met Glu Ser Gln Pro Thr His Phe Pro Phe Ser Thr
385                 390                 395                 400

Asp Ala Asn Thr Asn Pro Gly Asn Thr Ile Tyr Arg Ile Asn Leu Thr
            405                 410                 415

Pro Asn Ser Leu Thr Ser Ala Phe Asn Gly Leu Tyr Gly Asn Gly Ala
            420                 425                 430

Thr Leu Gly Asn Val
        435

<210> SEQ ID NO 3
<211> LENGTH: 704
<212> TYPE: PRT
<213> ORGANISM: Artificial Sequence
<220> FEATURE:
<223> OTHER INFORMATION: fusion protein sequence of Junonia coenia
      Densovirus structural protein VP4 fused to eGFP via a peptide
      linker

<400> SEQUENCE: 3

Met Ser Leu Pro Gly Thr Gly Ser Gly Thr Ser Ser Gly Gly Gly Asn
1               5                   10                  15

Thr Ser Gly Gln Glu Val Tyr Val Ile Pro Arg Pro Phe Ser Asn Phe
            20                  25                  30

Gly Lys Lys Leu Ser Thr Tyr Thr Lys Ser His Lys Phe Met Ile Phe
        35                  40                  45

Gly Leu Ala Asn Asn Val Ile Gly Pro Thr Gly Thr Gly Thr Thr Ala
    50                  55                  60

Val Asn Arg Leu Ile Thr Thr Cys Leu Ala Glu Ile Pro Trp Gln Lys
65                  70                  75                  80

Leu Pro Leu Tyr Met Asn Gln Ser Glu Phe Asp Leu Leu Pro Pro Gly
                85                  90                  95

Ser Arg Val Val Glu Cys Asn Val Lys Val Ile Phe Thr Asn Arg
            100                 105                 110

```
Ile Ala Phe Glu Thr Ser Ser Thr Ala Thr Lys Gln Ala Thr Leu Asn
            115                 120                 125
Gln Ile Ser Asn Leu Gln Thr Ala Val Gly Leu Asn Lys Leu Gly Trp
        130                 135                 140
Gly Ile Asp Arg Ser Phe Thr Ala Phe Gln Ser Asp Gln Pro Met Ile
145                 150                 155                 160
Pro Thr Ala Thr Ser Ala Pro Lys Tyr Glu Pro Ile Thr Gly Thr Thr
                165                 170                 175
Gly Tyr Arg Gly Met Ile Ala Asp Tyr Tyr Gly Ala Asp Ser Thr Asn
            180                 185                 190
Asp Ala Ala Phe Gly Asn Ala Gly Asn Tyr Pro His His Gln Val Gly
        195                 200                 205
Ser Phe Thr Phe Ile Gln Asn Tyr Tyr Cys Met Tyr Gln Gln Thr Asn
    210                 215                 220
Gln Gly Thr Gly Gly Trp Pro Cys Leu Ala Glu His Leu Gln Gln Phe
225                 230                 235                 240
Asp Ser Lys Thr Val Asn Asn Gln Cys Leu Ile Asp Val Thr Tyr Lys
                245                 250                 255
Pro Lys Met Gly Leu Ile Lys Pro Leu Asn Tyr Lys Ile Ile Gly
            260                 265                 270
Gln Pro Thr Ala Lys Gly Thr Ile Ser Val Gly Asp Asn Leu Val Asn
        275                 280                 285
Met Arg Gly Ala Val Val Ile Asn Pro Pro Glu Ala Thr Gln Ser Val
    290                 295                 300
Thr Glu Ser Thr His Asn Leu Thr Arg Asn Phe Pro Ala Asn Leu Phe
305                 310                 315                 320
Asn Ile Tyr Ser Asp Ile Glu Lys Ser Gln Ile Leu His Lys Gly Pro
                325                 330                 335
Trp Gly His Glu Asn Pro Gln Ile Gln Pro Ser Val His Ile Gly Ile
            340                 345                 350
Gln Ala Val Pro Ala Leu Thr Thr Gly Ala Leu Leu Val Asn Ser Ser
        355                 360                 365
Pro Leu Asn Ser Trp Thr Asp Ser Met Gly Tyr Ile Asp Val Met Ser
    370                 375                 380
Ser Cys Thr Val Met Glu Ser Gln Pro Thr His Phe Pro Phe Ser Thr
385                 390                 395                 400
Asp Ala Asn Thr Asn Pro Gly Asn Thr Ile Tyr Arg Ile Asn Leu Thr
                405                 410                 415
Pro Asn Ser Leu Thr Ser Ala Phe Asn Gly Leu Tyr Gly Asn Gly Ala
            420                 425                 430
Thr Leu Gly Asn Val Gly Asp Asp Ala Pro Pro Ser Pro Gly Pro Asp
        435                 440                 445
Pro Gly Pro Gln Pro Pro Pro Pro Pro Pro Ser Pro Thr Pro Val
    450                 455                 460
Gly Met Val Ser Lys Gly Glu Glu Leu Phe Thr Gly Val Val Pro Ile
465                 470                 475                 480
Leu Val Glu Leu Asp Gly Asp Val Asn Gly His Lys Phe Ser Val Ser
                485                 490                 495
Gly Glu Gly Glu Gly Asp Ala Thr Tyr Gly Lys Leu Thr Leu Lys Phe
            500                 505                 510
Ile Cys Thr Thr Gly Lys Leu Pro Val Pro Trp Pro Thr Leu Val Thr
        515                 520                 525
Thr Phe Thr Tyr Gly Val Gln Cys Phe Ser Arg Tyr Pro Asp His Met
```

```
                530             535             540
Lys Gln His Asp Phe Phe Lys Ser Ala Met Pro Glu Gly Tyr Val Gln
545                 550                 555                 560

Glu Arg Thr Ile Phe Phe Lys Asp Asp Gly Asn Tyr Lys Thr Arg Ala
                565                 570                 575

Glu Val Lys Phe Glu Gly Asp Thr Leu Val Asn Arg Ile Glu Leu Lys
            580                 585                 590

Gly Ile Asp Phe Lys Glu Asp Gly Asn Ile Leu Gly His Lys Leu Glu
        595                 600                 605

Tyr Asn Tyr Asn Ser His Asn Val Tyr Ile Met Ala Asp Lys Gln Lys
    610                 615                 620

Asn Gly Ile Lys Val Asn Phe Lys Ile Arg His Asn Ile Glu Asp Gly
625                 630                 635                 640

Ser Val Gln Leu Ala Asp His Tyr Gln Gln Asn Thr Pro Ile Gly Asp
                645                 650                 655

Gly Pro Val Leu Leu Pro Asp Asn His Tyr Leu Ser Thr Gln Ser Ala
                660                 665                 670

Leu Ser Lys Asp Pro Asn Glu Lys Arg Asp His Met Val Leu Leu Glu
            675                 680                 685

Phe Val Thr Ala Ala Gly Ile Thr His Gly Met Asp Glu Leu Tyr Lys
        690                 695                 700

<210> SEQ ID NO 4
<211> LENGTH: 32
<212> TYPE: PRT
<213> ORGANISM: Artificial Sequence
<220> FEATURE:
<223> OTHER INFORMATION: peptide linker

<400> SEQUENCE: 4

Gly Asp Asp Ala Pro Pro Ser Pro Gly Pro Asp Pro Gly Pro Gln Pro
1               5                   10                  15

Pro Pro Pro Pro Pro Pro Ser Pro Thr Pro Val Gly Gly Ala Ala Gly
            20                  25                  30

<210> SEQ ID NO 5
<211> LENGTH: 6
<212> TYPE: PRT
<213> ORGANISM: Artificial Sequence
<220> FEATURE:
<223> OTHER INFORMATION: artificial peptide sequence of an affinity tag

<400> SEQUENCE: 5

His His His His His His
1               5

<210> SEQ ID NO 6
<211> LENGTH: 37
<212> TYPE: PRT
<213> ORGANISM: Hadronyche versuta

<400> SEQUENCE: 6

Ser Pro Thr Cys Ile Pro Ser Gly Gln Pro Cys Pro Tyr Asn Glu Asn
1               5                   10                  15

Cys Cys Ser Gln Ser Cys Thr Phe Lys Glu Asn Glu Asn Gly Asn Thr
            20                  25                  30

Val Lys Arg Cys Asp
        35
```

```
<210> SEQ ID NO 7
<211> LENGTH: 88
<212> TYPE: PRT
<213> ORGANISM: Androctonus australis

<400> SEQUENCE: 7

Met Lys Phe Leu Leu Leu Phe Leu Val Val Leu Pro Ile Met Gly Val
1               5                   10                  15

Phe Gly Lys Lys Asn Gly Tyr Ala Val Asp Ser Ser Gly Lys Ala Pro
            20                  25                  30

Glu Cys Leu Leu Ser Asn Tyr Cys Asn Asn Glu Cys Thr Lys Val His
        35                  40                  45

Tyr Ala Asp Lys Gly Tyr Cys Cys Leu Leu Ser Cys Tyr Cys Phe Gly
    50                  55                  60

Leu Asn Asp Asp Lys Lys Val Leu Glu Ile Ser Asp Thr Arg Lys Ser
65                  70                  75                  80

Tyr Cys Asp Thr Thr Ile Ile Asn
                85

<210> SEQ ID NO 8
<211> LENGTH: 88
<212> TYPE: PRT
<213> ORGANISM: Androctonus australis

<400> SEQUENCE: 8

Met Lys Phe Leu Leu Leu Phe Leu Val Val Leu Pro Ile Met Gly Val
1               5                   10                  15

Leu Gly Lys Lys Asn Gly Tyr Ala Val Asp Ser Ser Gly Lys Ala Pro
            20                  25                  30

Glu Cys Leu Leu Ser Asn Tyr Cys Tyr Asn Glu Cys Thr Lys Val His
        35                  40                  45

Tyr Ala Asp Lys Gly Tyr Cys Cys Leu Leu Ser Cys Tyr Cys Phe Gly
    50                  55                  60

Leu Asn Asp Asp Lys Lys Val Leu Glu Ile Ser Asp Thr Arg Lys Ser
65                  70                  75                  80

Tyr Cys Asp Thr Pro Ile Ile Asn
                85

<210> SEQ ID NO 9
<211> LENGTH: 65
<212> TYPE: PRT
<213> ORGANISM: Androctonus australis

<400> SEQUENCE: 9

Glu His Gly Tyr Leu Leu Asn Lys Tyr Thr Gly Cys Lys Val Trp Cys
1               5                   10                  15

Val Ile Asn Asn Glu Glu Cys Gly Tyr Leu Cys Asn Lys Arg Arg Gly
            20                  25                  30

Gly Tyr Tyr Gly Tyr Cys Tyr Phe Trp Lys Leu Ala Cys Tyr Cys Gln
            35                  40                  45

Gly Ala Arg Lys Ser Glu Leu Trp Asn Tyr Lys Thr Asn Lys Cys Asp
    50                  55                  60

Leu
65

<210> SEQ ID NO 10
<211> LENGTH: 60
<212> TYPE: PRT
<213> ORGANISM: Androctonus australis
```

<400> SEQUENCE: 10

Asp Gly Tyr Ile Lys Arg His Asp Gly Cys Lys Val Thr Cys Leu Ile
1               5                   10                  15

Asn Asp Asn Tyr Cys Asp Thr Glu Cys Lys Arg Glu Gly Gly Ser Tyr
            20                  25                  30

Gly Tyr Cys Tyr Ser Val Gly Phe Ala Cys Trp Cys Glu Gly Leu Pro
        35                  40                  45

Asp Asp Lys Ala Trp Lys Ser Glu Thr Asn Thr Cys
    50                  55                  60

<210> SEQ ID NO 11
<211> LENGTH: 64
<212> TYPE: PRT
<213> ORGANISM: Leiurus quinquestriatus

<400> SEQUENCE: 11

Asp Gly Tyr Ile Lys Arg Arg Asp Gly Cys Lys Val Ala Cys Leu Ile
1               5                   10                  15

Gly Asn Glu Gly Cys Asp Lys Glu Cys Lys Ala Tyr Gly Gly Ser Tyr
            20                  25                  30

Gly Tyr Cys Trp Thr Trp Gly Leu Ala Cys Trp Cys Glu Gly Leu Pro
        35                  40                  45

Asp Asp Lys Thr Trp Lys Ser Glu Thr Asn Thr Cys Gly Gly Lys Lys
    50                  55                  60

<210> SEQ ID NO 12
<211> LENGTH: 61
<212> TYPE: PRT
<213> ORGANISM: Leiurus quinquestriatus

<400> SEQUENCE: 12

Asp Gly Tyr Ile Arg Lys Arg Asp Gly Cys Lys Leu Ser Cys Leu Phe
1               5                   10                  15

Gly Asn Glu Gly Cys Asn Lys Glu Cys Lys Ser Tyr Gly Gly Ser Tyr
            20                  25                  30

Gly Tyr Cys Trp Thr Trp Gly Leu Ala Cys Trp Cys Glu Gly Leu Pro
        35                  40                  45

Asp Asp Lys Thr Trp Lys Ser Glu Thr Asn Thr Cys Gly
    50                  55                  60

<210> SEQ ID NO 13
<211> LENGTH: 2124
<212> TYPE: DNA
<213> ORGANISM: Artificial Sequence
<220> FEATURE:
<223> OTHER INFORMATION: recombinant DNA sequence encoding Junonia
      coenia Densovirus coat protein VP4 fused to eGFP via a peptide
      linker

<400> SEQUENCE: 13
atgtcattac ctggaactgg ttctggaaca tcatctggag gaggcaacac ttcaggtcaa      60
gaggtttatg taattcctcg tccattttcg aactttggta aaaaattaag tacttataca     120
aagtctcata aatttatgat atttggtctt gccaataatg ttattggacc tacaggtact     180
ggtacaacag ctgtaaatcg tttaattaca acttgtttgg ctgaaattcc atggcagaaa     240
ttgcctttgt atatgaacca atctgaattt gatttattac ctcctggtag tagagtagtt     300
gaatgtaatg ttaaagtaat attcagaact aatcgtattg catttgagac tagttcaact     360

```
gctactaaac aagctacatt gaatcaaata tctaatttac aaactgctgt tggattaaat      420
aaacttggat ggggtattga tagatcattt actgcttttc aatcagatca acctatgatt      480
cccactgcta ctagtgcacc aaaatatgaa cctataactg gtacgactgg ttatagaggt      540
atgatagctg attattatgg tgctgattct actaatgatg ctgcatttgg taatgctggt      600
aactatcctc atcatcaagt tggttcattt acttttattc aaaattatta ttgtatgtat      660
caacaaacca atcaaggtac tggaggttgg ccatgtttag ctgaacatct tcaacaattt      720
gattctaaaa ctgttaataa tcaatgttta attgatgtaa cttataaacc taaaatgggt      780
ttaattaaac caccgttaaa tttataaaatt attggtcaac ctactgcaaa aggtactata      840
tctgttggtg ataatttagt taacatgcga ggagctgttg taataaatcc acctgaagca      900
acacaatctg ttactgaatc aactcataat ttgactcgca atttccagc taatttgttt      960 aatatttatt ctgacattga aaaatctcaa attttacata aaggaccttg gggacacgaa     1020
aatccacaga taaaccaag tgttcatatt ggtattcaag ctgtaccagc attaactaca     1080
ggagctttac ttgtaaattc aagtccttta aattcatgga ctgattctat gggttatatt     1140
gatgttatgt ctagttgtac tgttatggaa tctcagccta cacactttcc attttcgact     1200
gatgctaata ctaaccctgg taataccatt tatcgtatta atcttacacc gaactctctt     1260
actagtgctt tcaatggatt gtacggtaat ggagctactc ttggtaacgt tgggacgac      1320 gctccccgt caccagggcc tgatcccggg ccccaaccac caccacctcc acccccaagt     1380
cccactcccg taggaatggt gagcaagggc gaggagctgt tcaccggggt ggtgcccatc     1440
ctggtcgagc tggacggcga cgtaaacggc cacaagttca gcgtgtccgg cgagggcgag     1500
ggcgatgcca cctacggcaa gctgaccctg aagttcatct gcaccaccgg caagctgccc     1560
gtgccctggc ccaccctcgt gaccaccttc acctacggcg tgcagtgctt cagccgctac     1620
cccgaccaca tgaagcagca cgacttcttc aagtccgcca tgcccgaagg ctacgtccag     1680
gagcgcacca tcttcttcaa ggacgacggc aactacaaga cccgcgccga ggtgaagttc     1740
gagggcgaca ccctggtgaa ccgcatcgag ctgaagggca tcgacttcaa ggaggacggc     1800
aacatcctgg ggcacaagct ggagtacaac tacaacagcc acaacgtcta tatcatggcc     1860
gacaagcaga agaacggcat caaggtgaac ttcaagatcc gccacaacat cgaggacggc     1920
agcgtgcagc tcgccgacca ctaccagcag aacaccccca tcggcgacgg ccccgtgctg     1980
ctgcccgaca ccactacct gagcacccag tccgccctga gcaaagaccc caacgagaag     2040
cgcgatcaca tggtcctgct ggagttcgtg accgccgccg ggatcactca cggcatggac     2100
gagctgtaca agtaaagcgg ctaa                                             2124
```

<210> SEQ ID NO 14
<211> LENGTH: 84
<212> TYPE: DNA
<213> ORGANISM: Artificial Sequence
<220> FEATURE:
<223> OTHER INFORMATION: DNA sequence for PolyProline Linker

<400> SEQUENCE: 14

```
ggggacgacg ctcccccgtc accagggcct gatcccgggc cccaaccacc accacctcca       60
cccccaagtc ccactcccgt agga                                              84
```

<210> SEQ ID NO 15
<211> LENGTH: 533
<212> TYPE: PRT
<213> ORGANISM: Junonia coenia
<220> FEATURE:
<221> NAME/KEY: misc_feature
<222> LOCATION: (91)..(91)
<223> OTHER INFORMATION: Xaa can be any naturally occurring amino acid

<400> SEQUENCE: 15

```
Met Ser Arg Gln Ile Asn Ser Lys Tyr Leu Asn Ser Trp His Asp Trp
1               5                   10                  15

Ile Glu Gln Asn Lys His Asn Asn Phe Glu Gly Ile Gln Leu Pro Glu
            20                  25                  30

Asp Phe Tyr Thr Glu Glu Gln Thr Leu Ser Asp Ser Pro Met Ser Glu
        35                  40                  45

Gly Thr Lys Arg Lys Ala Asp Thr Pro Val Glu Glu Gly Pro Ser Lys
    50                  55                  60

Lys Gly Ala His Asn Ala Pro His Asn Ser Gln Gly Thr Asp Pro Gln
65                  70                  75                  80

Asn Pro Ser Ser Ser Gly Ala Thr Thr Ser Xaa Asp Val Glu Met Ala
                85                  90                  95

Met Ser Leu Pro Gly Thr Gly Ser Gly Thr Ser Ser Gly Gly Gly Asn
            100                 105                 110

Thr Ser Gly Gln Glu Val Tyr Val Ile Pro Arg Pro Phe Ser Asn Phe
        115                 120                 125

Gly Lys Lys Leu Ser Thr Tyr Thr Lys Ser His Lys Phe Met Ile Phe
    130                 135                 140

Gly Leu Ala Asn Asn Val Ile Gly Pro Thr Gly Thr Gly Thr Thr Ala
145                 150                 155                 160

Val Asn Arg Leu Ile Thr Thr Cys Leu Ala Glu Ile Pro Trp Gln Lys
                165                 170                 175

Leu Pro Leu Tyr Met Asn Gln Ser Glu Phe Asp Leu Leu Pro Pro Gly
            180                 185                 190

Ser Arg Val Val Glu Cys Asn Val Lys Val Ile Phe Arg Thr Asn Arg
        195                 200                 205

Ile Ala Phe Glu Thr Ser Ser Thr Ala Thr Lys Gln Ala Thr Leu Asn
    210                 215                 220

Gln Ile Ser Asn Leu Gln Thr Ala Val Gly Leu Asn Lys Leu Gly Trp
225                 230                 235                 240

Gly Ile Asp Arg Ser Phe Thr Ala Phe Gln Ser Asp Gln Pro Met Ile
                245                 250                 255

Pro Thr Ala Thr Ser Ala Pro Lys Tyr Glu Pro Ile Thr Gly Thr Thr
            260                 265                 270

Gly Tyr Arg Gly Met Ile Ala Asp Tyr Tyr Gly Ala Asp Ser Thr Asn
        275                 280                 285

Asp Ala Ala Phe Gly Asn Ala Gly Asn Tyr Pro His His Gln Val Gly
    290                 295                 300

Ser Phe Thr Phe Ile Gln Asn Tyr Tyr Cys Met Tyr Gln Gln Thr Asn
305                 310                 315                 320

Gln Gly Thr Gly Gly Trp Pro Cys Leu Ala Glu His Leu Gln Gln Phe
                325                 330                 335

Asp Ser Lys Thr Val Asn Asn Gln Cys Leu Ile Asp Val Thr Tyr Lys
            340                 345                 350

Pro Lys Met Gly Leu Ile Lys Pro Leu Asn Tyr Lys Ile Ile Gly
        355                 360                 365

Gln Pro Thr Ala Lys Gly Thr Ile Ser Val Gly Asp Asn Leu Val Asn
    370                 375                 380
```

```
Met Arg Gly Ala Val Val Ile Asn Pro Pro Glu Ala Thr Gln Ser Val
385                 390                 395                 400

Thr Glu Ser Thr His Asn Leu Thr Arg Asn Phe Pro Ala Asn Leu Phe
            405                 410                 415

Asn Ile Tyr Ser Asp Ile Glu Lys Ser Gln Ile Leu His Lys Gly Pro
        420                 425                 430

Trp Gly His Glu Asn Pro Gln Ile Gln Pro Ser Val His Ile Gly Ile
    435                 440                 445

Gln Ala Val Pro Ala Leu Thr Thr Gly Ala Leu Leu Val Asn Ser Ser
450                 455                 460

Pro Leu Asn Ser Trp Thr Asp Ser Met Gly Tyr Ile Asp Val Met Ser
465                 470                 475                 480

Ser Cys Thr Val Met Glu Ser Gln Pro Thr His Phe Pro Phe Ser Thr
                485                 490                 495

Asp Ala Asn Thr Asn Pro Gly Asn Thr Ile Tyr Arg Ile Asn Leu Thr
            500                 505                 510

Pro Asn Ser Leu Thr Ser Ala Phe Asn Gly Leu Tyr Gly Asn Gly Ala
        515                 520                 525

Thr Leu Gly Asn Val
    530

<210> SEQ ID NO 16
<211> LENGTH: 488
<212> TYPE: PRT
<213> ORGANISM: Junonia coenia
<220> FEATURE:
<221> NAME/KEY: misc_feature
<222> LOCATION: (46)..(46)
<223> OTHER INFORMATION: Xaa can be any naturally occurring amino acid

<400> SEQUENCE: 16

Met Ser Glu Gly Thr Lys Arg Lys Ala Asp Thr Pro Val Glu Glu Gly
1               5                   10                  15

Pro Ser Lys Lys Gly Ala His Asn Ala Pro His Asn Ser Gln Gly Thr
            20                  25                  30

Asp Pro Gln Asn Pro Ser Ser Ser Gly Ala Thr Thr Ser Xaa Asp Val
        35                  40                  45

Glu Met Ala Met Ser Leu Pro Gly Thr Gly Ser Gly Thr Ser Ser Gly
50                  55                  60

Gly Gly Asn Thr Ser Gly Gln Glu Val Tyr Val Ile Pro Arg Pro Phe
65                  70                  75                  80

Ser Asn Phe Gly Lys Lys Leu Ser Thr Tyr Thr Lys Ser His Lys Phe
                85                  90                  95

Met Ile Phe Gly Leu Ala Asn Asn Val Ile Gly Pro Thr Gly Thr Gly
            100                 105                 110

Thr Thr Ala Val Asn Arg Leu Ile Thr Thr Cys Leu Ala Glu Ile Pro
        115                 120                 125

Trp Gln Lys Leu Pro Leu Tyr Met Asn Gln Ser Glu Phe Asp Leu Leu
    130                 135                 140

Pro Pro Gly Ser Arg Val Val Glu Cys Asn Val Lys Val Ile Phe Arg
145                 150                 155                 160

Thr Asn Arg Ile Ala Phe Glu Thr Ser Ser Thr Ala Thr Lys Gln Ala
                165                 170                 175

Thr Leu Asn Gln Ile Ser Asn Leu Gln Thr Ala Val Gly Leu Asn Lys
            180                 185                 190

Leu Gly Trp Gly Ile Asp Arg Ser Phe Thr Ala Phe Gln Ser Asp Gln
```

```
                195                 200                 205
Pro Met Ile Pro Thr Ala Thr Ser Ala Pro Lys Tyr Glu Pro Ile Thr
        210                 215                 220
Gly Thr Thr Gly Tyr Arg Gly Met Ile Ala Asp Tyr Tyr Gly Ala Asp
225                 230                 235                 240
Ser Thr Asn Asp Ala Ala Phe Gly Asn Ala Gly Asn Tyr Pro His His
                245                 250                 255
Gln Val Gly Ser Phe Thr Phe Ile Gln Asn Tyr Tyr Cys Met Tyr Gln
                260                 265                 270
Gln Thr Asn Gln Gly Thr Gly Gly Trp Pro Cys Leu Ala Glu His Leu
            275                 280                 285
Gln Gln Phe Asp Ser Lys Thr Val Asn Asn Gln Cys Leu Ile Asp Val
        290                 295                 300
Thr Tyr Lys Pro Lys Met Gly Leu Ile Lys Pro Pro Leu Asn Tyr Lys
305                 310                 315                 320
Ile Ile Gly Gln Pro Thr Ala Lys Gly Thr Ile Ser Val Gly Asp Asn
                325                 330                 335
Leu Val Asn Met Arg Gly Ala Val Val Ile Asn Pro Pro Glu Ala Thr
            340                 345                 350
Gln Ser Val Thr Glu Ser Thr His Asn Leu Thr Arg Asn Phe Pro Ala
        355                 360                 365
Asn Leu Phe Asn Ile Tyr Ser Asp Ile Glu Lys Ser Gln Ile Leu His
370                 375                 380
Lys Gly Pro Trp Gly His Glu Asn Pro Gln Ile Gln Pro Ser Val His
385                 390                 395                 400
Ile Gly Ile Gln Ala Val Pro Ala Leu Thr Thr Gly Ala Leu Leu Val
                405                 410                 415
Asn Ser Ser Pro Leu Asn Ser Trp Thr Asp Ser Met Gly Tyr Ile Asp
            420                 425                 430
Val Met Ser Ser Cys Thr Val Met Glu Ser Gln Pro Thr His Phe Pro
            435                 440                 445
Phe Ser Thr Asp Ala Asn Thr Asn Pro Gly Asn Thr Ile Tyr Arg Ile
        450                 455                 460
Asn Leu Thr Pro Asn Ser Leu Thr Ser Ala Phe Asn Gly Leu Tyr Gly
465                 470                 475                 480
Asn Gly Ala Thr Leu Gly Asn Val
            485
```

INSECT TOXIN DELIVERY MEDIATED BY A DENSOVIRUS COAT PROTEIN

CROSS-REFERENCE TO RELATED APPLICATIONS AND INCORPORATION BY REFERENCE MATERIAL SUBMITTED ELECTRONICALLY

This application is a U.S. National Stage application of International Application No. PCT/IB2017/055903, filed Sep. 27, 2017, which claims the benefit of priority to U.S. Provisional Patent Application No. 62/400,381, entitled "Insect Toxin Delivery Mediated by a Densovirus Coat Protein," filed Sep. 27, 2016. The entire contents and disclosure of these patent applications are incorporated herein by reference in its entirety.

This application makes reference to the following U.S. patents and U.S. patent applications: U.S. Provisional Patent Application No. 62/400,381, entitled "Insect Toxin Delivery Mediated by a Densovirus Coat Protein," filed Sep. 27, 2016; U.S. patent application Ser. No. 13/492,779, entitled "Aphicidal Toxins and Methods," filed Jun. 8, 2012, which claims priority from U.S. Provisional Patent Application No. 61/494,559, entitled "Aphicidal Toxins and Methods," filed Jun. 8, 2011; U.S. Pat. No. 7,547,677, entitled "Plant virus transmission inhibitor and methods," filed Jun. 16, 2009, which claims benefit of U.S. Provisional Application 60/869,545, filed Dec. 11, 2006; U.S. Pat. No. 6,673,340, entitled "Basement membrane degrading proteases as insect toxins and methods of use for same," filed Jan. 6, 2004, which claims the benefit of U.S. Provisional Application(s) No(s) 60/143,586 filed Jul. 13, 1999; U.S. Pat. No. 7,312,080, entitled "Plant Resistance to Insect Pests Mediated by Viral Proteins," filed Jan. 15, 2003, which is a continuation of U.S. application Ser. No. 09/395,401 filed Sep. 14, 1999, now abandoned, which claims priority from U.S. Provisional Application No. 60/100,132 filed Sep. 14, 1998; U.S. Pat. No. 5,674,747, entitled "Viral vector coding for juvenile hormone esterase," filed Oct. 7, 1997, which is a division of U.S. application Ser. No. 07/927,851, filed Aug. 10, 1992; U.S. Pat. No. 5,643,776, which is a continuation-in part of U.S. application Ser. No. 07/725,226, filed Jun. 26, 1991, now abandoned, which was a continuation of U.S. application Ser. No. 07/265,507, filed Nov. 1, 1988, now abandoned; U.S. Pat. No. 5,643,776, entitled "Insect diagnostic and control compositions," filed Jul. 1, 1997, which is a continuation in part of U.S. application Ser. No. 07/725,226, filed Jun. 26, 1991, now abandoned which was a continuation of U.S. application Ser. No. 07/265,507, filed Nov. 1, 1988, now abandoned. The entire disclosure and contents of these patents/applications are incorporated herein by reference.

A Sequence Listing, which is a part of the present disclosure, is submitted concurrently with the specification as a text file. The name of the text file containing the Sequence Listing is "53066_Seqlisting.txt." The Sequence Listing was created on Mar. 26, 2019, and is 34,840 bytes in size. The subject matter of the Sequence Listing is incorporated herein in its entirety by reference.

STATEMENT OF JOINT RESEARCH AGREEMENT

In compliance with 37 C.F.R. § 1.71(g)(1), disclosure is herein made that the inventions described and claimed herein were made pursuant to a Joint Research Agreement as defined in 35 U.S.C. 103 (c)(3), that was in effect on or before the date the inventions were made, and as a result of activities undertaken within the scope of the Joint Research Agreement, by or on the behalf of the University of Florida and Iowa State University.

STATEMENT REGARDING SEQUENCE LISTING

The Sequence Listing associated with this application is provided in text format in lieu of a paper copy, and is hereby incorporated by reference into the specification. The name of the text file containing the Sequence Listing is T2315-22736WO01-ST25.txt. The text file is 34 KB, was created on Sep. 25, 2017, and is being submitted electronically via EFS-Web, concurrent with the filing of the specification.

BACKGROUND

Field of the Invention

The disclosed invention relates generally to the field of insect pest control.

Related Art

Insects cause agricultural loss and economic damage worldwide. The extensive use of chemical insecticides for insect pest management has resulted in chemical insecticide resistance now being recorded in more than 500 species of insects and mites. In addition, current chemical control has no target effects. There is a long felt need in the art for environmentally friendly and economical methods for reducing damage to both crop and ornamental plants from insect infestation. Novel approaches for insect pest management are needed.

SUMMARY

According to a first broad aspect, the disclosed invention provides a fusion protein comprising a carrier protein attached to a second peptide via a peptide linker, wherein the carrier protein is derived from a *Junonia coenia* densovirus (JcDNV) coat protein (VP).

According to a second broad aspect, the disclosed invention provides a composition comprising a fusion protein. The fusion protein comprises a carrier protein attached to a second peptide via a peptide linker. The carrier protein is derived from a *Junonia coenia* densovirus (JcDNV) coat protein (VP).

According to a third broad aspect, the disclosed invention provides a recombinant DNA comprising a nucleic acid sequence encoding a fusion protein, wherein the fusion protein comprises a carrier protein attached to a second peptide via a peptide linker, and wherein the carrier protein is derived from a *Junonia coenia* densovirus (JcDNV) coat protein.

According to a fourth broad aspect, the disclosed invention provides an expression cassette for expression of a fusion protein comprising a regulatory region operably linked to a nucleic acid sequence encoding a fusion protein. The fusion protein comprises a carrier protein attached to a second peptide via a peptide linker. The carrier protein is derived from a *Junonia coenia* densovirus (JcDNV) coat protein.

According to a fifth broad aspect, the disclosed invention provides a vector comprising an expression cassette for expression of a fusion protein. The expression cassette comprises a regulatory region operably linked to a nucleic acid sequence encoding a fusion protein. The fusion protein comprises a carrier protein attached to a second peptide via a peptide linker. The carrier protein is derived from a *Junonia coenia* densovirus (JcDNV) coat protein.

According to a sixth broad aspect, the disclosed invention provides a method of controlling insect pests. The method comprises feeding a fall armyworm, *Spodoptera frugiperda*, with a food source comprising a fusion protein. The fusion protein comprises a JcDNV coat protein attached to an insect toxin via a peptide linker, thereby allowing the fusion protein to pass across the gut epithelium of the fall armyworm and act within the hemocoel of the fall armyworm after the fusion protein is ingested by the fall armyworm.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 1 is an illustration showing proteins capable of transcellular transport;

FIG. 5 illustrates Scorpion, *Androctonus australis*, derived Hector insect toxin (AaHIT1 (SEQ ID NO: 7), AaHIT2 (SEQ ID NO: 8), AaHIT3 (SEQ ID NO: 9), AaHIT4 (SEQ ID NO: 10) and AaHIT5 (SEQ ID NO: 11) that can be fused to a JcDNV coat protein according to one embodiment of the disclosed invention;

FIG. 6 illustrates insect toxins LqHIT2 (SEQ ID NO: 1) and LqqIT2 (SEQ ID NO: 12) that can be fused to a JcDNV coat protein, respectively, according to one embodiment of the disclosed invention;

DETAILED DESCRIPTION OF THE PREFERRED EMBODIMENTS

Definitions

Figure 2:
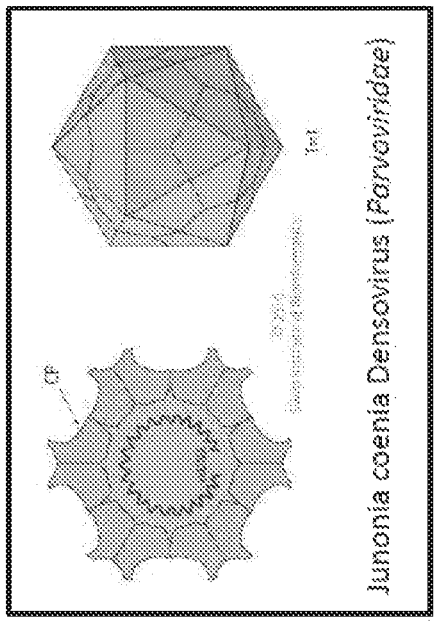
FIG. 2 is a set of images showing a natural transport system of virus.
Figure 2:
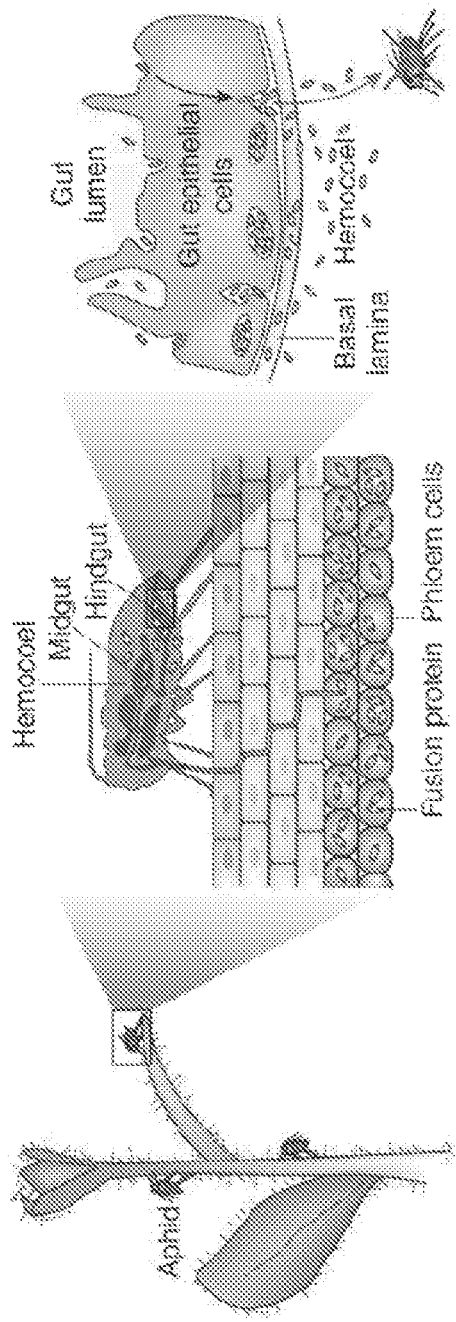

Where the definition of terms departs from the commonly used meaning of the term, applicant intends to utilize the definitions provided below, unless specifically indicated.

The practice of the disclosed invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., Langenheim and Thimann, (1982) *Botany: Plant Biology and Its Relation to Human Affairs*, John Wiley; *Cell Culture and Somatic Cell Genetics of Plants*, vol. 1, Vasil, ed. (1984); Stanier, et al., (1986) *The Microbial World*, 5$^{th}$ ed., Prentice-Hall; Dhringra and Sinclair, (1985) *Basic Plant Pathology Methods*, CRC Press; Maniatis, et al., (1982) *Molecular Cloning: A Laboratory Manual; DNA Cloning*, vols. I and II, Glover, ed. (1985); *Oligonucleotide Synthesis*, Gait, ed. (1984); *Nucleic Acid Hybridization*, Hames and Higgins, eds. (1984); and the series *Methods in Enzymology*, Colowick and Kaplan, eds, Academic Press, Inc., San Diego, Calif.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

For purposes of the disclosed invention, it should be noted that the singular forms, "a," "an" and "the" include reference to the plural unless the context as herein presented clearly indicates otherwise.

For purpose of the disclosed invention, the term "adjacent" refers to "next to" or "adjoining something else."

For purposes of the disclosed invention, a value or property is "based" on a particular value, property, the satisfaction of a condition, or other factor, if that value is derived by performing a mathematical calculation or logical decision using that value, property or other factor.

For purposes of the disclosed invention, the term "comprising", the term "having", the term "including," and variations of these words are intended to be open-ended and mean that there may be additional elements other than the listed elements.

For purposes of the disclosed invention, directional terms such as "top," "bottom," "upper," "lower," "above," "below," "left," "right," "horizontal," "vertical," "up," "down," etc., are used merely for convenience in describing the various embodiments of the disclosed invention. The embodiments of the disclosed invention may be oriented in various ways. For example, the diagrams, apparatuses, etc., shown in the drawing figures may be flipped over, rotated by 90° in any direction, reversed, etc.

For purposes of the disclosed invention, the term "toward" refers to decreasing the distance between two aligned objects. For example, a contact controlling positioning device may be used to move: a stamp towards an ink palette, an ink palette towards a stamp, a stamp towards a substrate, a substrate towards a stamp, etc.

For purposes of the disclosed invention, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80% or 90%, preferably 60-90% of the native protein for its native substrate. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). See also, Creighton, Proteins, W.H. Freeman and Co. (1984).

For purpose of the disclosed invention, the term "polypeptide" and the term "protein" are used interchangeably herein to refer to a polymer of amino acid residues. The terms encompass amino acid polymers in which one or more amino acid residues are artificial chemical mimetic of a corresponding naturally occurring amino acids, as well as to naturally occurring amino acid polymers and non-naturally occurring amino acid polymer.

For purpose of the disclosed invention, the term "coat protein" or the term "viral coat protein" refer to a protein component of a capsid of a virus.

For purpose of the disclosed invention, the term "correspond" and the term "corresponding" refer to that a protein sequence refer interchangeably to an amino acid position(s) of a protein. An amino acid at a position of a protein may be found to be equivalent or corresponding to an amino acid at a position of one or more other protein(s) based on any relevant evidence, such as the primary sequence context of the each amino acid, its position in relation to the N-terminal ends of its respective protein, the structural and functional roles of each amino acid in its respective protein, etc. In a similar fashion, the C-terminal is also contemplated as discussed above.

For purpose of the disclosed invention, the term "fragment" of a molecule such as a protein or nucleic acid refers to a portion of the amino acid or nucleotide sequence.

For purpose of the disclosed invention, the term "fuse" refers to join together physically, or to make things join together and become a single thing.

For purpose of the disclosed invention, the term "fusion protein" refers to a polypeptide or a protein created through the joining of two or more genes that originally coded for separate proteins.

For purpose of the disclosed invention, the term "identical" or the term "identity" refers to the percentage of amino acid residues of two or more polypeptide sequences having the same amino acid at corresponding positions.

For purpose of the disclosed invention, the term "linked" refers to a covalent linkage between two polypeptides in a fusion protein. The polypeptides are typically joined via a peptide bond, either directly to each other or via one or more additional amino acids.

For purpose of the disclosed invention, the term "linker" refers to short peptide sequences that occur between functional protein domains and link the functional domains together. Linkers designed by researchers are generally classified into three categories according to their structures: flexible linkers, rigid linkers, and in vivo cleavable linkers. A flexible linker is often composed of flexible residues like glycine and serine so that the adjacent protein domains are free to move relative to one another. A linker also may play a role in releasing the free functional domain in vivo (as in in vivo cleavable linkers). Linkers may offer many other advantages for the production of fusion proteins, such as improving biological activity, increasing expression yield, and achieving desirable pharmacokinetic profiles. The composition and length of a linker may be determined in accordance with methods well known in the art and may be tested for efficacy. A linker is generally from about 3 to about 15 amino acids long, in some embodiments about 5 to about 10 amino acids long, however, longer or shorter linkers may be used or the linker may be dispensed with entirely. According to embodiments of the present disclosure, either a proline-rich linker or a glycine linker may be utilized. For example, a linker used in embodiments can be a porline-rich linker having the amino acid sequence set forth in SEQ ID NO: 4.

For purpose of the disclosed invention, the term "mutant protein" refers to a protein product encoded by a gene with mutation.

For purpose of the disclosed invention, the term "protein domain" refers to a distinct functional or structural unit in a protein. Usually, a protein domain is responsible for a particular function or interaction, contributing to the overall role of a protein. Domains may exist in a variety of biological contexts, where similar domains can be found in proteins with different functions.

For purpose of the disclosed invention, the term "recombinant protein" refers to a protein derived from a recombinant DNA, that is, it's code was carried by a "recombinant DNA" molecule. Recombinant DNA molecules are DNA molecules formed by laboratory methods of genetic recombination (such as molecular cloning) to bring together genetic material from multiple sources, creating sequences that would not otherwise be found in biological organisms.

For purpose of the disclosed invention, the term "recombinant protein" refers to a protein derived from a recombinant DNA, that is, it's code was carried by a "recombinant DNA" molecule. Recombinant DNA molecules are DNA molecules formed by laboratory methods of genetic recombination (such as molecular cloning) to bring together genetic material from multiple sources, creating sequences that would not otherwise be found in biological organisms.

For purpose of the disclosed invention, the term "recombinant vaccine" refers to a vaccine made by genetic engineering, the process and method of manipulating the genetic material of an organism. Usually, a recombinant vaccine encompasses one or more protein antigens that have either been produced and purified in a heterologous expression system (e.g., bacteria or yeast) or purified from large amounts of the pathogenic organism. The vaccinated person produces antibodies to the one or more protein antigens, thus protecting him/her from disease.

For purpose of the disclosed invention, the term "subject" or the term "individual" refers interchangeably to a mammalian organism, such as a human, mouse, etc., that is administered a mutant protein of the disclosed invention for a therapeutic or experimental purpose.

For purpose of the disclosed invention, the term "subunit" refers to a separate polypeptide chain that makes a certain protein which is made up of two or more polypeptide chains joined together. In a protein molecule composed of more than one subunit, each subunit can form a stable folded structure by itself. The amino acid sequences of subunits of a protein can be identical, similar, or completely different.

For purpose of the disclosed invention, the term "suitable vector" refers to any vector (for example, a plasmid or virus) which may incorporate a nucleic acid sequence encoding an antigenic polypeptide and any desired control sequences. It may bring about the expression of the nucleic acid sequence. The choice of the vector will typically depend on the compatibility of the vector with a host cell into which the vector is to be introduced.

For purpose of the disclosed invention, the term "suitable vector" refers to any vector (for example, a plasmid or virus) which may incorporate a nucleic acid sequence encoding an antigenic polypeptide and any desired control sequences. It may bring about the expression of the nucleic acid sequence. The choice of the vector will typically depend on the compatibility of the vector with a host cell into which the vector is to be introduced.

For purposes of the disclosed invention, the following terms are used to describe the sequence relationships between two or more nucleic acids or polynucleotides or polypeptides: (a) "reference sequence," (b) "comparison window," (c) "sequence identity," (d) "percentage of sequence identity," and (e) "substantial identity."

For purposes of the disclosed invention, the phrase "consisting essentially of" when used in relation to a specified nucleic acid, includes reference to the inclusion of additional sequences to an object polynucleotide where the additional sequences do not selectively hybridize, under stringent hybridization conditions, to the same cDNA as the polynucleotide and where the hybridization conditions include a wash step in 0.1×SSC and 0.1% sodium dodecyl sulfate at 65° C.

For purposes of the disclosed invention, the term "analogue" and the term "analog" include reference to one of a group of chemical compounds that share structural and/or functional similarities but are different in respect to elemental composition. A structural analog is a compound having a structure similar to that of another one, but differing from it in respect of one or more components, such as one or more atoms, functional groups, or substructures, etc. Functional analogs are compounds that has similar physical, chemical, biochemical, or pharmacological properties. Functional analogs are not necessarily also structural analogs with a similar chemical structure.

For purposes of the disclosed invention, the term "bind," the term "binding" or the term "bound" refers to any type of chemical or physical binding, which includes but is not limited to covalent binding, hydrogen binding, electrostatic binding, biological tethers, transmembrane attachment, cell surface attachment and expression.

For purposes of the disclosed invention, the term "carrier protein" or the term "carrier peptide" refers to a protein or peptide that moves from the insect gut into the hemocoel. A carrier protein is a protein that may deliver an insecticidal toxin from an insect gut into the hemocoel of the insect. Potential carrier proteins are proteins that move from the insect gut into the hemocoel. Gut binding proteins can bind to receptors on an insect gut membrane and a subset will transcytose across the gut epithelium into the insect hemocoel. They are potential carrier proteins that can help delivery of toxins to target sites in the hemocoel.

For purposes of the disclosed invention, the term "chimeric insecticidal toxin" and the term "fusion insecticidal toxin" refer to a fusion protein comprising an insecticidal toxin portion and a peptide portion that mediates binding of the insecticidal toxin portion to an insect gut membrane and allows transcytosis in an insect in which the insecticidal toxin without that peptide portion is not active or has very little activity.

For purposes of the disclosed invention, the term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, and 50, 100 or longer. Those of skill in the art understand that to avoid a high similarity to a reference sequence due to inclusion of gaps in the polynucleotide sequence a gap penalty is typically introduced and is subtracted from the number of matches. Methods of alignment of nucleotide and amino acid sequences for comparison are well known in the art. The local homology algorithm (BESTFIT) of Smith and Waterman, (1981) *Adv. Appl. Math* 2:482, may conduct optimal alignment of sequences for comparison; by the homology alignment algorithm (GAP) of Needleman and Wunsch, (1970) *J. Mol. Biol.* 48:443-53; by the search for similarity method (Tfasta and Fasta) of Pearson and Lipman, (1988) *Proc. Natl. Acad. Sci. USA* 85:2444; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Version 8 (available from Genetics Computer Group (GCG® programs (Accelrys, Inc., San Diego, Calif.).). The CLUSTAL program is well described by Higgins and Sharp, (1988) *Gene* 73:237-44; Higgins and Sharp, (1989) *CABIOS* 5:151-3; Corpet, et al., (1988) *Nucleic Acids Res.* 16:10881-90; Huang, et al., (1992) *Computer Applications in the Biosciences* 8:155-65, and Pearson, et al., (1994) *Meth. Mol. Biol.* 24:307-31. The preferred program to use for optimal global alignment of multiple sequences is PileUp (Feng and Doolittle, (1987) *J. Mol. Evol.*, 25:351-60 which is similar to the method described by Higgins and Sharp, (1989) *CABIOS* 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel et al., eds., Greene Publishing and Wiley-Interscience, New York (1995). GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, and 40, 50 or greater. GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) Proc. Natl. Acad. Sci. USA 89:10915). Unless otherwise stated, sequence identity/similarity values provided herein refer to the value obtained using the BLAST 2.0 suite of programs using default parameters (Altschul, et al., (1997) Nucleic Acids Res. 25:3389-402). As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

For purposes of the disclosed invention, the term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) J. Gen. Microbiol. 139:425-32) can be modified to yield a functionally identical molecule. Accordingly, each silent variation of a nucleic acid, which encodes a polypeptide of the disclosed invention, is implicit in each described polypeptide sequence and incorporated herein by reference.

For purposes of the disclosed invention, the term "crop plants" and the term "agricultural plants" refer to plants that have economic importance for human or animal food production, or for animal fodder production. "Crop plants" or "agricultural plants" can include grains, fruits and vegetables as well as grasses. Horticultural plants include those for turfgrass, windbreaks and landscaping and include ornamental plants such as flowers, shrubs, vines and the like.

For purposes of the disclosed invention, the term "encoding" and the term "encoded," when used in relation to a specified nucleic acid, include reference to comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (Yamao, et al., (1985) Proc. Natl. Acad. Sci. USA 82:2306-9), or the ciliate *Macronucleus*, may be used when the nucleic acid is expressed using these organisms. When the nucleic acid is prepared or altered synthetically, advantage can be taken of known codon preferences of the intended host where the nucleic acid is to be expressed. For example, although nucleic acid sequences of the disclosed invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) Nucleic Acids Res. 17:477-98 and herein incorporated by reference). Thus, the rice preferred codon for a particular amino acid might be derived from known gene sequences from rice.

For purposes of the disclosed invention, the term "expression cassette" refers to a part of a vector DNA used for cloning and transformation. In each successful transformation, the expression cassette directs the cell's machinery to make RNA and protein. Some expression cassettes are designed for modular cloning of protein-encoding sequences so that the same cassette can easily be altered to make different proteins. Expression cassettes may also refer to a recombinantly produced nucleic acid molecule that is capable of expressing a genetic sequence in a cell. An expression cassette typically includes a regulatory region such as a promoter, (allowing transcription initiation), and a sequence encoding one or more proteins or RNAs. Optionally, the expression cassette may include transcriptional enhancers, non-coding sequences, splicing signals, transcription termination signals, and polyadenylation signals. The sequences controlling the expression of the gene, i.e. its transcription and the translation of the transcription product, are commonly referred to as regulatory unit. Most parts of the regulatory unit are located upstream of coding sequence of the heterologous gene and are operably linked thereto. The expression cassette may also contain a downstream 3' untranslated region comprising a polyadenylation site. The regulatory unit of the invention is either directly linked to the gene to be expressed, i.e. transcription unit, or is separated therefrom by intervening DNA such as for example by the 5'-untranslated region of the heterologous gene. Preferably the expression cassette is flanked by one or more suitable restriction sites in order to enable the insertion of the expression cassette into a vector and/or its excision from a vector. Thus, the expression cassette according to the disclosed invention can be used for the construction of an expression vector, in particular a mammalian expression vector.

For purposes of the disclosed invention, the term "expression vector," otherwise known as an expression construct, refers to a plasmid or virus designed for protein expression in cells. The vector is used to introduce a specific gene into a target cell, and can commandeer the cell's mechanism for protein synthesis to produce the protein encoded by the gene. The plasmid is engineered to contain regulatory sequences that act as enhancer and promoter regions and lead to efficient transcription of the gene carried on the expression vector. The goal of a well-designed expression vector is the production of significant amount of stable messenger RNA, and therefore proteins.

For purposes of the disclosed invention, the term "fusion protein," the term "chimeric protein," the term "fusion polypeptide," the term "fusion toxic," and the term "chimeric toxin" are used herein to describe a protein comprising portions from different sources (not both parts of the same naturally occurring polypeptide chain). Optionally, a peptide linker can be included to facilitate folding of the domains (portions) into their natural conformations by reducing steric hindrance between those domains. Such a fusion protein may have an additional domain, for example a tag sequence to facilitate purification of the fusion protein. A tag can be any of a number of known tags widely known and available to the art (Streptavidin-binding, glutathione binding, polyhistidine, flagellar antigen and others). refers to a polypeptide or a protein created through the joining of two or more genes that originally coded for separate proteins. Translation of this fusion gene results in a single or multiple polypeptides with functional properties derived from each of the original proteins. Usually, a fusion protein has at least two heterologous polypeptides covalently linked, either directly or via an amino acid linker (peptide linker). The heterologous polypeptides forming a fusion protein are typically linked C-terminus to N-terminus, although they can also be linked C-terminus to C-terminus, N-terminus to N-terminus, or N-terminus to C-terminus. The polypeptides of the fusion protein can be in any order and may include more than one of either or both of the constituent polypeptides. These terms encompass conservatively modified variants, polymorphic variants, alleles, mutants, subsequences, interspecies homologs, and immunogenic fragments of the antigens that make up the fusion protein. Recombinant fusion proteins are created artificially by recombinant DNA technology for use in biological research or therapeutics.

For purposes of the disclosed invention, the term "gut binding protein," the term "gut binding peptide," the term "gut binding delivery protein" refer to a protein that binds to a protein receptor on a gut membrane of an insect and can pass across the gut epithelium and transcytose into the insect hemocoel. According to the embodiments of the disclosed invention, a gut binding protein that is transcytosed across the gut epithelium can be exploited to devise novel delivery systems for toxins that act within the hemocoel, thereby providing a new approach for arthropod pest management. In particular, a "gut binding protein" as used in this invention is preferably an insect virus coat protein used to transport a neurotoxin across the gut epithelium.

For purposes of the disclosed invention, the term "heterologous," when used in relation to a nucleic acid, includes reference to a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

For purposes of the disclosed invention, the term "host cell" includes reference to a cell that can be used as a host that can be introduced with foreign nucleic acid. For example, a host cell can comprise a heterologous nucleic acid sequence of the invention, which contains a vector and supports the replication and/or expression of the expression vector. Host cells may be prokaryotic cells such as *E. coli*, or eukaryotic cells such as yeast, insect, plant, amphibian, or mammalian cells. Preferably, host cells are monocotyledonous or dicotyledonous plant cells, including but not limited to maize, sorghum, sunflower, soybean, wheat, alfalfa, rice, cotton, canola, lawn grass, barley, millet, and tomato.

For purposes of the disclosed invention, the term "introduce," when used in relation to a nucleic acid, refers to inserting a nucleic acid into a cell. Introducing a nucleic acid into a cell can be done by "transfection," "transformation," or "transduction." In some situations, introducing a nucleic acid into a cell can include the incorporation of a nucleic acid into a eukaryotic or prokaryotic cell, where the nucleic acid can be incorporated into the genome of the cell (e.g., chromosome, plasmid, plastid or mitochondrial DNA), converted into an autonomous replicon, or transiently expressed (e.g., transfected mRNA).

For purposes of the disclosed invention, the term "isolated," "isolated nucleic acid," or "isolated protein," includes reference to a material, such as a nucleic acid or a protein, which is substantially or essentially free from components which normally accompany or interact with it as found in its naturally occurring environment. The isolated material optionally comprises material not found with the material in its natural environment.

For purposes of the disclosed invention, the term "nucleic acid library" refers to a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, (1987) *Guide To Molecular Cloning Techniques*, from the series *Methods in Enzymology*, vol. 152, Academic Press, Inc., San Diego, Calif.; Sambrook, et al., (1989) *Molecular Cloning: A Laboratory Manual*, 2*nd* ed., vols. 1-3; and *Current Protocols in Molecular Biology*, Ausubel, et al., eds, Current Protocols, a joint venture between Greene Publishing Associates, Inc. and John Wiley & Sons, Inc. (1994 Supplement).

For purposes of the disclosed invention, the term "nucleic acid" and the term "polynucleotide," as used interchangeably herein, include reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

For purposes of the disclosed invention, the term "operably linked," the term "operably associated," and the term "functionally linked" are used interchangeably and include reference to a functional relationship between two or more DNA segment. Particularly, "operably linked" refers to refer to a functional linkage between a first nucleic acid sequence, such as a promoter, in a functional relationship with a second nucleic acid sequence, wherein the promoter sequence initiates and mediates transcription of the DNA corresponding to the second sequence. A promoter/enhancer sequence, including any combination of cis-acting transcriptional control elements is operably associated to a coding sequence if the promoter/enhancer sequence affects the transcription or expression of the coding sequence in an appropriate host cell or other expression system. Promoter regulatory sequences that are operably linked to the transcribed gene sequence are physically contiguous to the transcribed sequence. Generally, operably linked means that the nucleic acid sequences being linked are contiguous and, where necessary to join two protein coding regions, contiguous and in the same reading frame.

For purposes of the disclosed invention, the term "peptide linker" and the term "linker" are interchangeable and refer to short peptide sequences that occur between functional protein domains and link the functional domains together. Linkers designed by researchers are generally classified into three categories according to their structures: flexible linkers, rigid linkers, and in vivo cleavable linkers. A flexible linker is often composed of flexible residues like glycine and serine so that the adjacent protein domains are free to move relative to one another. A linker also may play a role in releasing the free functional domain in vivo (as in in vivo cleavable linkers). Linkers may offer many other advantages for the production of fusion proteins, such as improving biological activity, increasing expression yield, and achieving desirable pharmacokinetic profiles. The composition and length of a linker may be determined in accordance with methods well known in the art and may be tested for efficacy. A linker may have about 3 to about 15 amino acids. In some embodiments of the disclosed invention, a linker may have about 5 to about 10 amino acids, however, longer linker may be used in embodiments of the disclosed invention.

For purposes of the disclosed invention, the term "percentage of sequence identity" refers to the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

For purposes of the disclosed invention, the term "plant" includes reference to whole plants, plant organs (e.g., leaves, stems, roots, etc.), seeds and plant cells and progeny of same. Plant cell, as used herein includes, without limitation, cells in or from seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium*, and *Triticum*. A particularly preferred plant is *Zea mays*.

For purposes of the disclosed invention, the term "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

For purposes of the disclosed invention, the term "polypeptide," the term "peptide," and the term "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

For purposes of the disclosed invention, the term "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such *Agrobacterium* or *Rhizobium*. Examples are promoters that preferentially initiate transcription in certain tissues, such as leaves, roots, seeds, fibres, xylem vessels, tracheids, or sclerenchyma. Such promoters are referred to as "tissue-preferred." A "cell type" specific promoter primarily drives expression in certain cell types in one or more organs, for example, vascular cells in roots or leaves. An "inducible" or "regulatable" promoter is a promoter which is under environmental control. Examples of environmental conditions that may affect transcription by inducible promoters include anaerobic conditions or the presence of light. Another type of promoter is a developmentally regulated promoter, for example, a promoter that drives expression during pollen development. Tissue preferred, cell type specific, developmentally regulated, and inducible promoters constitute the class of "non-constitutive" promoters. A "constitutive" promoter is a promoter, which is active under most environmental conditions.

For purposes of the disclosed invention, the term "purified" refers to the component in a relatively pure state, e.g. about 80% pure or greater. In one embodiment, VP4-P-eGFP used an experiment disclosed herein is about 80-90%.

For purposes of the disclosed invention, the term "recombinant expression cassette" refers to a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

For purposes of the disclosed invention, the term "recombinant" refers to a genetic material formed by a genetic recombination process. A "recombinant protein is made through genetic engineering. A recombinant protein is coded by a DNA sequence created artificially. A recombinant protein is a protein that is coded by a recombinant nucleic acid sequence. A recombinant nucleic acid sequence has a sequence from two or more sources incorporated into a single molecule.

For purposes of the disclosed invention, the term "reference sequence" refers to a defined sequence used as a basis for sequence comparison. A reference sequence may be a subset or the entirety of a specified sequence; for example, as a segment of a full-length cDNA or gene sequence, or the complete cDNA or gene sequence.

For purposes of the disclosed invention, the term "residue," the term "amino acid residue," or the term "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

For purposes of the disclosed invention, the term "room temperature" refers to a temperature of from about 20° C. to about 25° C.

For purposes of the disclosed invention, the term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

For purposes of the disclosed invention, the term "sequence identity" or the term "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

For purposes of the disclosed invention, the term "site of action" refers to the location in a target insect where an insect toxin has biological activity. For example, the site of action for a neurotoxin would have biological activity with nerves.

For purposes of the disclosed invention, the term "stringent conditions" or the term "stringent hybridization conditions" include reference to conditions under which a probe can hybridize to its target sequence, to a detectably greater degree than other sequences (e.g., at least 2-fold over background). Stringent conditions are sequence-dependent and can be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence. Typically, stringent conditions are those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, (1984) Anal. Biochem., 138:267-84: $T_m$=81.5° C.+16.6 (log M)+0.41 (% GC)−0.61 (% form)− 500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, part I, chapter 2, "Overview of principles of hybridization and the strategy of nucleic acid probe assays," Elsevier, New York (1993); and *Current Protocols in Molecular Biology*, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

For purposes of the disclosed invention, the term "substantial identity" refers to that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, supra.

An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides which are "substantially similar" share sequences as noted above, except that residue positions which are not identical may differ by conservative amino acid changes. One of skill will recognize that these values can be appropriately adjusted to determine corresponding identity of proteins encoded by two nucleotide sequences by taking into account codon degeneracy, amino acid similarity, reading frame positioning and the like. Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

For purposes of the disclosed invention, the term "target insect" refers to an insect to be killed or inhibited in feeding by a insecticidal fusion protein as described herein.

For purposes of the disclosed invention, the term "transfection" refers to a variety of art-recognized techniques for introducing foreign nucleic acid (e.g., DNA) into a host cell by calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEI™ (Polyplus-transfection Inc., New York, N.Y.), EFFECTENE® (Qiagen, Valencia, Calif.), DREAMFECT™ (OZ Biosciences, France) and the like), electroporation (e.g., in vivo electroporation), etc. Suitable methods for transfecting host cells can be found in Sambrook, et al., ("Molecular Cloning: A Laboratory Manual." 2nd, ed., Cold Spring harbor Laboratory, Cold Spring Harbor Laboratory Press, Cold Spring Harbor, N.Y., 1989), and other laboratory manuals.

For purposes of the disclosed invention, the term "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

For purposes of the disclosed invention, the term "vector" includes reference to a nucleic acid used in transfection of a host cell and into which can be inserted a polynucleotide. Vectors are often replicons. Expression vectors permit transcription of a nucleic acid inserted therein.

DESCRIPTION

While the invention is susceptible to various modifications and alternative forms, specific embodiment thereof has been shown by way of example in the drawings and will be described in detail below. It should be understood, however that it is not intended to limit the invention to the particular forms disclosed, but on the contrary, the invention is to cover all modifications, equivalents, and alternatives falling within the spirit and the scope of the invention.

Insect pests continue to reduce crop yields. With resistance developing in many cases to classical chemical insecticides, novel alternative approaches to insect pest control are needed. Although gut-active toxins such as those derived from *Bacillus thuringiensis* (Bt) have been successfully used for insect pest management, a diverse range of insect-specific insecticidal peptides remains an untapped resource for pest management efforts. These toxins act within the insect hemocoel (body cavity) and hence require a delivery system to access their target site. Recently, an appropriate delivery of such hemocoelic insect toxins, via fusion to a second protein such as a plant lectin or a luteovirus coat protein for transcytosis across the gut epithelium, or via entomopathogenic fungi has been developed.[4]

The disclosed technology exploits an alternative approach to use the biological toxins and peptides for insect pest control, targeting the needs for environmentally friendly and economical methods for reducing damage to both crop and ornamental plants from insect infestation.

Toxins and Peptides with Insecticidal Activity

Insecticidal activity of some toxins and peptides are illustrated in Table 1.

ins that act within the insect hemocoel remain an untapped resource for pest management efforts. Insect-specific toxins either act at the gut epithelium or act within the hemocoel (body cavity), requiring appropriate delivery to their site of action.[2] Due to the challenge of appropriate delivery to their target site, hemocoelic toxins have not been widely adopted.

The venom from a wide range of predatory species (e.g., scorpions, wasps, predaceous mites, cone snails, anemones, lacewings, and parasitoids), provides an outstanding resource for isolation of insect-specific neurotoxins. These insecticidal neurotoxins typically target sodium, potassium, calcium, or chloride channels. With few exceptions, these neurotoxins are not orally active and require appropriate delivery systems to access their target site, the nerves.

Arachnids have a venom apparatus and secrete a complex chemical mixture of low molecular mass organic molecules, enzymes and polypeptide neurotoxins designed to paralyze or kill their prey. Based on the number of species and number of toxins present in the venoms of those examined, there are an estimated 0.5-1.5 million arachnid-derived insecticidal peptides. It is predicted that there are at least 10 million bioactive spider-venom peptides. ArachnoServer is a database containing information on the sequence, three-dimensional structure, and biological activity of protein toxins derived from spider venom. Of 800 peptides in the ArachnoServer 2.0 Database, 136 are insecticidal peptides, of which 38 are insect selective, 34 are nonselective, and 64 are unknown phyletic selectivity.

Arthropod-derived neuropeptides, enzymes, and hormones that function to regulate insect development and maintain homeostasis (e.g., diuretic hormones, and juvenile hormone esterase) also include peptides that have potentially insecticidal effects when delivered outside their normal physiological timeframe. Although these peptides act as endogenous regulators and provide insect specificity, a major drawback of using these peptides as insecticides is that high concentrations of these peptides are usually required to overcome natural regulatory mechanisms that restore appropriate physiological levels within the insect.

TABLE 1

Toxins and Peptides that act within the hemocoel resulting in Insecticidal Activity

| Source | Toxin/Peptide | Targets | References |
|---|---|---|---|
| Bacteria | Makes Caterpillars Floppytoxin 1(Mcf1) | Cellapoptosis | Ffrench-Constant et al (2007)[15] |
| | *Photorhabdusvirulence* cassettes | Unknown | Ffrench-Constant et al (2007)[15] |
| Arachnids | Hv1A<br>PI1a<br>(Predicted 0.5-1.5 million insecticidal peptides) | Ion channels<br>Cell membrane<br>Neurons | Windley et al (2012)[2] |
| Vertebrates | Cobra neurotoxins | Muscles<br>Axonal conduction<br>Hemolytic activity | Primor et al. (1980)[16] |
| Insects | Adipokinetic hormone | Metabolic functions<br>Locomotion | Stone et al (1976)[17] |
| | Diuretic hormone | Water balance<br>Feeding behavior | Gade (2004),[18] |
| | Cockroach, Cricket, Moth Allatostatin | JH biosynthesis (Crickets),<br>Ecdysteroids (Lepidoptera) | Gade (2004),[18]<br>Schoofs et al. (1998)[19] |

Insect-specific toxins such as those derived from *Bacillus thuringiensis* have been employed successfully for the management of numerous arthropod pests.[1] However, a diverse range of insect-specific insecticidal peptides and neurotox- A few arthropod-derived insecticidal peptides (e.g., proctolin and *Aedes aegypti* trypsin modulating oostatic factor, TMOF) are transported at low levels across the insect gut epithelium. The target specificity of these naturally occurring arthropod-derived insecticidal peptides is particularly appealing for the development of novel pest management technologies where appropriate delivery systems are provided.

Spider, *Hadronyche versuta* omega atracotoxin, Hv1a (SEQ ID No: 6) is an insecticidal peptide derived from the venom of an Australian funnel-web spider (*Hadronyche versuta*), specifically inhibits insect but not mammalian voltage-gated calcium channels. Hv1a is highly toxic by injection towards many different insect pests including species from the orders Lepidoptera, Coleoptera, Diptera, and Dictyoptera, and is ineffective after oral ingestion. However, Hv1a is orally toxic against one tick species (*Amblyomma americanum*), which may be related to differences in gut physiology associated with blood feeding.[21] The spider-derived toxins, such as Hv1a, that contain a disulfide pseudoknot are classified as inhibitor cystine-knot (ICK) motif toxins. The cystine-knot in these neurotoxins results in strong chemical, thermal, and biological stability, contributing to their persistence and making them particularly attractive for use as model toxins.

Lack of effective oral delivery limits the adoption of many toxins and peptides with insecticidal activity. It is a challenge to overcome insect midgut and cuticle barriers for delivery of toxins and peptides to their target sites in the hemocoel.

Potential Carrier Proteins

Potential carrier proteins are proteins that move from the insect gut into the hemocoel. Gut binding proteins can bind to receptors on an insect gut membrane and a subset will transcytose across the gut epithelium into the insect hemocoel. They are potential carrier proteins that can help delivery of toxins to target sites in the hemocoel. A diverse range of proteins and peptides move from the gut into the hemocoel in a broad range of arthropods.[6] These proteins and peptides range widely in molecular mass and include bovine serum albumin (BSA), immunoglobulins (IgG), and teratocyte-secreted protein (TSP14).[6] Some proteins that have been observed to transcytose across the gut epithelium of insects (e.g., IgG, albumin, and horse radish peroxidase), are known to do the same in mammals.[3] Analyses show that the efficiency of transport of these proteins tends to be low. For example, about 1% of Bovine Serum Albumin (BSA) is transcytosed with the majority targeted to lysosomes in the silkworm, *B. mori*.[4]

Figure 1:
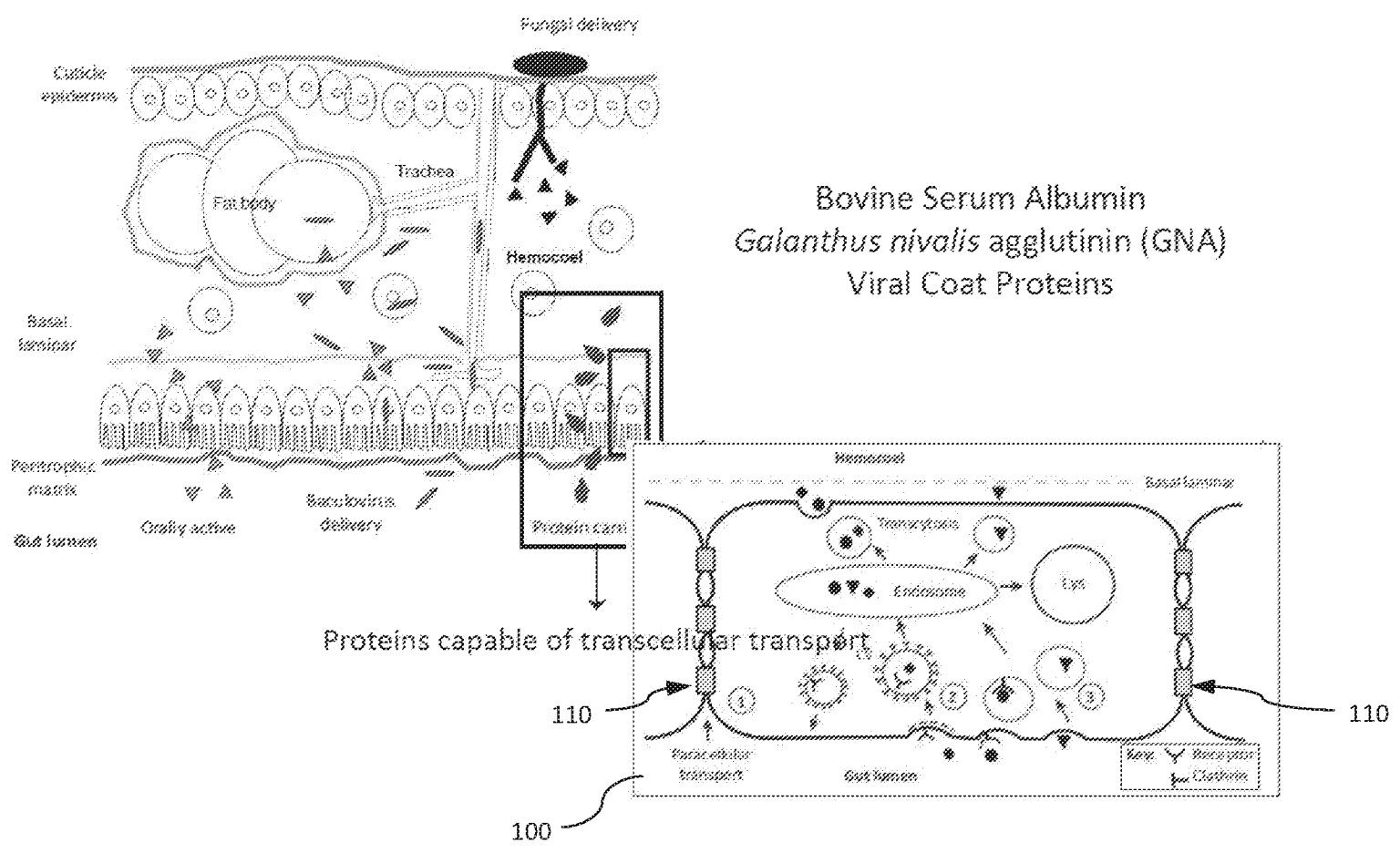

FIG. 1 shows proteins capable of transcellular transport. Such proteins are potential carrier proteins for delivery of intrahemocoelic toxins for management of insect pests. In FIG. 1, boxes 110 represent cell junctions. Abbreviation "cv" represents clathrin-coated vesicle; Abbreviation "Lys" represents lysosome. In a few cases such as teratocyte-secreted protein (TSP) 14, intrahemocoelic toxins (depicted as triangles) are orally active and can be delivered directly from transgenic plants. For intrahemocoelic toxins that are not orally active, a protein carrier (depicted by circles) such as a lectin (e.g., the snowdrop lectin, *Galanthus nivalis* agglutin, GNA) or the coat protein of an insect-vectored plant virus [e.g., Pea enation mosaic virus (PEMV) vectored by the pea aphid] can be used to deliver toxins into the hemocoel.[4] Alternatively, insect pathogens can be used as vectors for expression of the toxin and secretion into the hemocoel of the infected insect. Baculoviruses (depicted as rods in FIG. 1) infect the midgut epithelium and other tissues such as the fat body. Virus-expressed toxin secreted into the hemocoel results in death of the host insect.[4] Entomopathogenic fungi (depicted at top, right in FIG. 1) such as *Metarhizium anisopliae* can also be engineered for release of intrahemocoelic toxins into the hemocoel.[4] In contrast to other modes of delivery, fungal delivery is via the cuticle, rather than via the gut of the insect. Inset 100 illustrates the mechanisms of transport across the insect gut epithelium: (1) Paracellular transport: movement of proteins such as proctolin via intercellular septate junctions; Endocytosis (receptor-mediated or receptor-independent) via (2) clathrin-coated vesicles (e.g., PEMV coat protein, or albumin), or (3) independent of clathrin (e.g., ferritin). Endocytosed vesicles fuse with the endosome and are sorted for trafficking to the lysosome for degradation, apical membrane (receptor recycling), or basolateral plasma membrane (transcytosis).

FIG. 2 illustrates a set of images showing a natural transport system of virus. Transcytosis across the insect gut epithelium is a key event in the infection cycle (e.g. densoviruses) or for transmission (e.g. luteoviruses) of certain viruses. Coat proteins on the capsid of a virus mediate binding of the virus to cell surface and subsequent endocytosis of the virus. These viruses have coevolved over the millennia with their insect hosts or vectors and are expected to have evolved efficient mechanisms to avoid being trafficked to the lysosome. For example, a large number of plant viruses are vectored by sap-sucking insects (*Hemiptera*) including aphids, whiteflies, leafhoppers, plant hoppers, and thrips, with more than half of these viruses vectored by aphids.[4] The persistently transmitted viruses (i.e., plant viruses that enter and persist in the hemocoel of the insect vector) are ingested during vector feeding on plant sap, and then move from the gut of the vector into the hemocoel before being transmitted to other plants via the salivary glands. These plant viruses typically do not replicate in the insect vector. It is expected that plant viruses, e.g., luteoviruses, are evolved to avoid being targeted to the lysosome following receptor-mediated endocytosis into epithelial cells. Based on transmission electron micrographs, the movement of the luteoviruses across the gut epithelium of the aphid vector is mediated by clathrin-coated vesicles. These vesicles form tubular transport structures that release virus into the hemocoel. A similar clathrin-coated-vesicle-mediated process occurs for virus movement from the hemocoel across the accessory salivary gland into the duct of the aphid salivary gland.[4]

The ability of the virus to pass across gut into a hemocoel of an insect by transcytosis is of particular interest for the delivery of insect-specific toxins into the insect's hemocoel. Luteovirus coat protein (CP) has been shown to be able to be transcytosed with a great efficiency and can effectively deliver insect toxin against aphids.[4]

Different from plant virus, Densoviruses are insect virus. Densoviruses are small, nonenveloped, single-stranded DNA (ssDNA) viruses that are pathogenic for arthropods. They are parvoviruses that can be lethal for insects of different orders at larval stages.[8] Densoviral pathogenesis usually starts with the ingestion of contaminated food by the host. The success of infection is found to depend on the virus capacity to enter the intestinal epithelium. *Junonia coenia* densovirus (JcDNV) belongs to the densovirus genus of the Parvoviridae family and infects the larvae of the Common Buckeye butterfly. Transcytosis is the mechanism involved in JcDNV transport across the midgut epithelium.[8] Coat proteins mediate binding of JcDNV to cell surface and subsequent endocytosis. These coat proteins are evolved to cross barriers to establish infection. JcDNV capsid is icosahedral and consists of viral structural proteins, i.e., coat proteins, VP1 (88 kDa), VP2 (58 kDa), VP3 (52 kDa), and VP4 (47 kDa), which are splicing variants.

Figure 3:
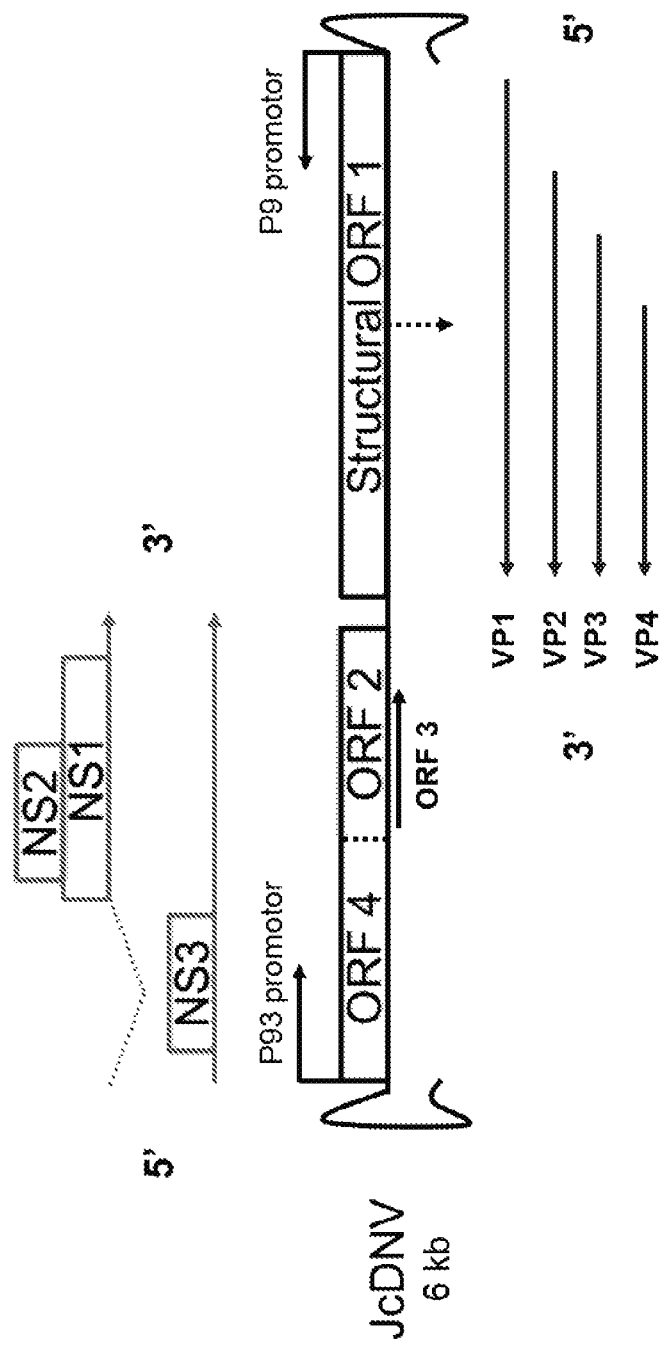
FIG. 3 is a schematic illustration showing the genome of *Junonia coenia* densovirus, depicting the open reading frames (ORF) of non-structural (NS) and structural proteins (VP), produced by leaky scanning and alternative splicing.

FIG. 3 is a schematic illustration showing the genome of *Junonia coenia* densovirus, depicting the open reading frames (ORF) of non-structural (NS) and structural proteins (VP), produced by leaky scanning and alternative splicing. As shown in FIG. 3, the linear, ssDNA genome of JcDNV includes ORF1, ORF2, ORF3, and ORF4, as well as long inverted terminal repeats. The four structural proteins VP1, VP2, VP3, and VP4 are nested in a single large open reading frame (ORF), ORF1, located in the 5' half of one strand, whereas in the 5' half of the complementary strand ORF2, ORF3, and ORF4 encode the three nonstructural (NS) proteins NS-1, NS-2, and NS-3, respectively.[26] VP and NS genes are transcribed from the P9 and P93 promoters, respectively. The four overlapping capsid polypeptides are synthesized from an unspliced 2.5-kb mRNA by a "leaky-scanning" mechanism whereby ribosomes initiate translation at the first, second, third, or fourth/fifth in-frame AUG codon. Thus, the four VPs share the same C-terminal sequence and differ only in their N-terminal region and the length of its N-terminal extension.[14, 27] The amino acid sequence for VP1 is set forth in SEQ ID No: 1. The amino acid sequence for VP1 is set forth in SEQ ID No: 15. The amino acid sequence for VP1 is set forth in SEQ ID No: 16. The amino acid sequence for VP4 is set forth in SEQ ID No: 2.

Wang et al. 2013 shows that JcDNV is specifically internalized *Spodoptera frugiperda* by endocytosis in absorptive cells and then cross the epithelium of the fall armyworm, (*S. frugiperda*) by transcytosis.[8] The fall armyworm, *S. frugiperda*, is part of the order of Lepidoptera and is the larval (caterpillar) life stage of a fall armyworm moth. Lepidoptera is an order of insects that includes butterflies and moths (both are called lepidopterans). The Lepidoptera includes about 180,000 species in about 126 families and about 46 superfamilies. The fall armyworm, *S. frugiperda*, is a continuous resident of the Gulf States and is also a major pest in the U.S. and South America. Corn, sorghum, and other plants of the grass family are its preferred foods. The fall armyworm also attacks alfalfa, bean, peanut, potato, sweet potato, turnip, spinach, tomato, cabbage, cucumber, cotton, tobacco, all grain crops, and clover. Each year the fall armyworm can be found as far north as Montana, Michigan, and New Hampshire. In the southeast it occurs annually on late corn. Traditional Bt toxins and chemical insecticides have been failed to control *S. frugiperda* due to the resistance of the fall armyworm to these BT toxins and insecticides. Although Wang et al. 2013 has described the movement of the virus across the gut epithelium of a fall armyworm, it has not been established that a JcDNV coat protein, without the virion structure, will do the same.

The present disclosure identifies that a JcDNV coat protein, e.g., VP4, rapidly crosses the midgut epithelium of a fall armyworm *Spodoptera frugiperda* (*S. frugiperda*). The ability of the JcDNV coat proteins to cross the gut epithelium into the hemocoel (body cavity) allows these proteins to be used as carrier proteins for delivery of attached insecticidal proteins or peptides that act within the hemocoel across the gut epithelium of a target insect for insect pest control.

In particular, a JcDNV coat protein, such as VP1, VP2, VP3, VP4, or combinations or fragments thereof, can be used as a carrier protein and be fused or attached to a second protein or peptide, and facilitate the transport of the second protein or peptide across the gut epithelium into the hemocoel of an insect. The second protein or peptide can be an insecticidal protein or peptide, e.g. insect-specific toxin, insect-specific neurotoxins, etc. Thus, an insecticidal protein or peptide can be attached to a JcDNV coat protein to form an insecticidal fusion protein. Such an insecticidal fusion protein, after being ingested by a target insect, can pass across the gut epithelial layer and act within the hemocoel of the target insect pest, thereby killing the target insect pest. The present disclosure demonstrates that a JcDNV coat protein is effective for delivery of an interested protein, such as an insect-specific toxin, to its target site in a fall armyworm. Accordingly, embodiments provide an insecticidal fusion protein comprising an insect-specific toxin portion attached to a JcDNV coat protein. In one embodiment, the insecticidal fusion protein is a fusion protein comprising an insect-specific neurotoxin attached to VP4 via a peptide linker. VP4, which acts as a carrier protein or delivery peptide, is capable of facilitating the transport of a hemocoelic insect toxin that is attached to VP4 across the midgut epithelium into the hemocoel of a fall armyworm. Therefore, the insect-specific neurotoxin attached to VP4 can be delivered by VP4 to its site of action. Alternatively, the coat protein of JcDNV can be VP1, VP2, or VP3. VP1, VP2, VP3, and VP4 all have common C termini and can function as carrier peptides to facilitate delivery of interested protein into the hemocoel of an insect.

Figure 4:
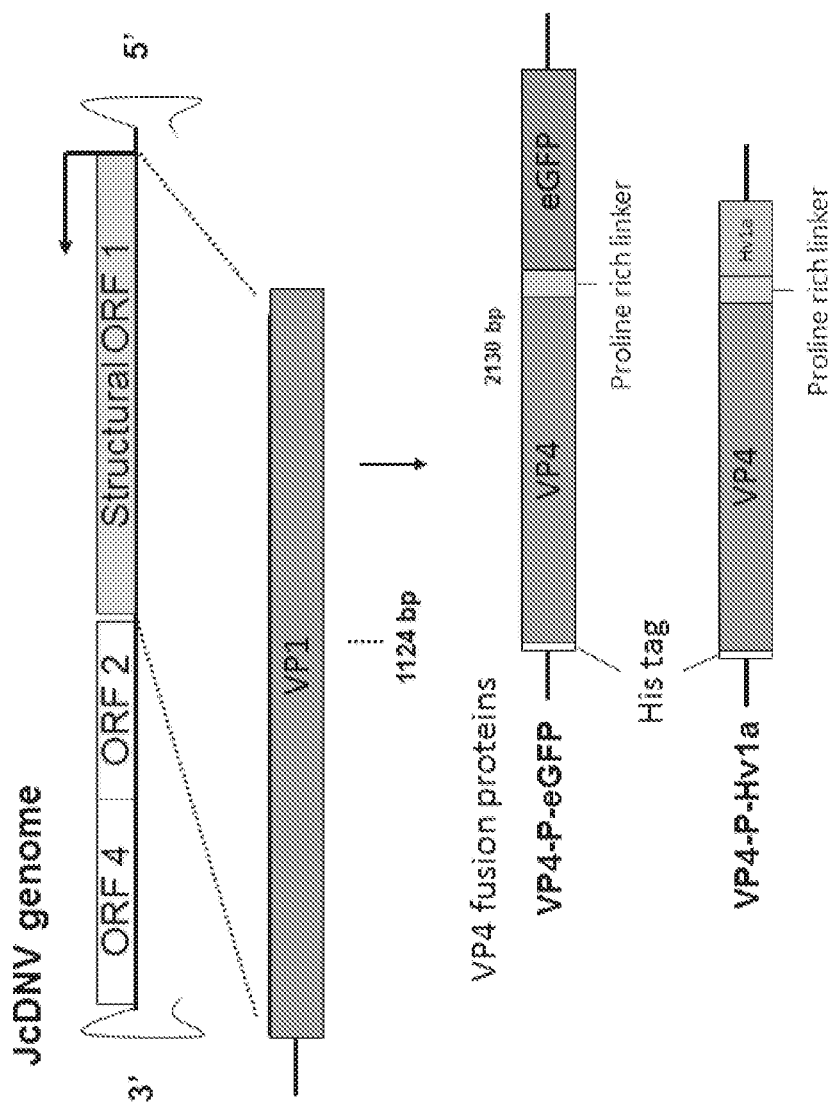
FIG. 4 is a schematic of JcDNV genome and the construction of a recombinant protein comprising a VP4-fusion protein sequence according to one embodiment of the disclosed invention.

FIG. 4 is a schematic of JcDNV genome and the construction of a recombinant protein comprising a VP4-fusion protein sequence according to one embodiment of the disclosed invention. VP4-P-eGFP is a fusion protein comprising VP4 attached to the N-terminus of eGFP through a proline rich linker. In one embodiment, the amino acid sequence for VP4-P-eGFP is set forth in SEQ ID No: 3. The proline rich linker has a sequence set forth in SEQ ID No: 4. A His tag is attached at the N-terminal end of VP4 for purification of the recombinant protein of His-tagged VP4-P-eGFP. In one embodiment, the His tag is a 6× poly(His) tag which has a sequence set forth in SEQ ID No: 5. Similarly, VP4-P-Hv1a shown in FIG. 4 is a fusion protein comprising VP4 attached to the N-terminus of insect toxin Hv1a through a proline rich linker. In one embodiment, the amino acid sequence for Hv1a is set forth in SEQ ID No: 6. The proline rich linker between VP4 and Hv1a is protease-resistant and has a sequence set forth in SEQ ID No: 4. A His tag is attached at the N-terminal end of VP4 for purification of the recombinant protein of His-tagged VP4-P-Hv1a. The His tag can be a 6× poly(His) tag which has a sequence set forth in SEQ ID No: 5.

For simplicity of illustration, FIG. 4 only shows His-tagged VP4-P-eGFP and His-tagged VP4-P-Hv1a. However, peptide or protein other than eGFP or Hv1a can be fused to VP4, or other JcDNV coat proteins such as VP1, VP2 or VP4. For example, in an alternative embodiment, a toxin fused to VP4 is a venom derived from an insect predatory species. The insect predatory species can be one or more of scorpions, wasps, predaceous mites, cone snails, anemones, lacewings, and parasitoids. The toxin can be an insect-specific neurotoxin. In an alternative embodiment, a toxin can be an insect-specific toxin derived from arthropod neuropeptides, enzymes, and/or hormone. The insect-specific toxin can further be proctolin or *Aedes aegypti* trypsin modulating oostatic factor (TMOF). In alternative embodiments, the second peptide or protein that is fused to a JcDNV coat protein such as VP4 can be an insect toxin derived from *Androctonus australis* Hector insect toxin (AaHIT), as shown in FIG. 5. The AaHIT fused to VP4 can be AaHIT1, AaHIT2, AaHIT4, or AaHIT5. The sequence for AaHIT1 is set forth in SEQ ID No: 7; the sequence for AaHIT2 is set forth in SEQ ID No: 8; the sequence for AaHIT4 is set forth in SEQ ID No: 9; the sequence for AaHIT5 is set forth in SEQ ID No: 10. Alternatively, an insecticidal fusion protein can comprise VP4 fused to insect toxin LqHIT2 or LqqIT2 shown in FIG. 6. LqHIT2 is an insect toxin derived from Scorpion, *Leiurus quinquestriatus hebraeus* and has a sequence set forth in SEQ ID No: 11. LqqIT2 is a beta-insect depressant toxin derived from Scorpion, *Leiurus quinquestriatus hebraeus*, and has a sequence set forth in SEQ ID No: 12.

For simplicity of illustration, FIG. 4 only shows the proline rich linker (SEQ ID No: 6). However, the peptide linker shown in FIG. 4 is not exclusive. One of ordinary skill in the art would readily appreciate that any peptide linker that is suitable for fusion a JcDNV coat protein to a second peptide or protein can be utilized. In an embodiment, a suitable peptide linker is a protease-resistant linker.

For simplicity of illustration, FIG. 4 only shows a His tag attached to the N terminal end of VP4 for purification of a VP4 fused protein. The His-tag can be a 6× His tag (SEQ ID No: 5) or a His tag with various number of poly-His. However, tags that can be used for purification of a fusion protein comprising a JcDNV coat protein fused to a second peptide or protein are not limited to the tag shown in FIG. 4. Other tags, such as a FLAG-tag, a STREP-TAG® II, a glutathione-S-transferase (GST), etc., can be used to purify the fusion protein disclosed herein. For example, an affinity tag such as a FLAG-tag or a GST tag can be attached to the N terminal of VP4 of a VP4 fusion protein to purify the VP4 fusion protein. The tags listed herein are not exclusive. One of ordinary skill in the art would readily appreciate a tag that is suitable for purification of a fusion protein described herein.

Disclosed embodiments further provide a composition including a fusion protein that comprises JcDNV coat protein attached to a second peptide or protein via a peptide linker. The JcDNV coat protein is a carrier protein for delivery of attached protein or peptide such as insecticidal proteins or peptides that act within the hemocoel across the gut epithelium of a target insect for insect pest control. Therefore, the second protein comprised in the fusion protein can be an insect toxin. In some alternative embodiments, a composition comprises an insecticidal fusion protein constructed by fusing a JcDNV coat protein such as VP4 to an insect toxin via a peptide linker such as a proline rich linker. The insect toxin can be an insect-specific toxin. To ensure the intact of the fusion protein during transport into hemocoel, the peptide linker can be a protease-resistant linker. In an alternative embodiment, an insect toxin is an insect-specific toxin such as Hv1a, AaHIT1, AaHIT2, AaHIT4, AaHIT5, LqHIT2, LqqIT2, etc. The insect-specific toxin can be an insect-specific neurotoxin. In an alternative embodiment, the insect-specific toxin comprises an arthropod-derived neuropeptides, enzymes, and/or hormone. Alternatively, the insect-specific toxin can be proctolin or *Aedes aegypti* trypsin modulating oostatic factor (TMOF). In one alternative embodiment, the second protein is eGFP.

In an alternative embodiment, a composition comprising a carrier protein attached to an insect toxin is prepared in a spray formulation for spray. The carrier protein is derived from a JcDNV coat protein. The composition can be a liquid or a fluid. The composition can be sprayed to plants or to insect prone areas and deposited on the surface of the plants or the insect prone areas. After springing of the composition comprising an insecticidal fusion protein disclosed herein to a plant, the insecticidal fusion protein comprised in the composition disclosed herein can be deposited on the surface of a leave, the branch, or other areas of the plant. After the plant is orally ingested by an insect such as a fall armyworm, the insecticidal fusion protein deposited on the surface of the plant can pass across the gut epithelium and enter into the hemocoel of the insect, and, therefore, act within the hemocoel of the insect and kill the insect.

Embodiments of the disclosed invention also provide a recombinant DNA encoding the fusion proteins disclosed herein. In an embodiment, a recombinant DNA comprises a nucleic acid sequence encoding a carrier protein attached to a second peptide or protein via a peptide linker. The carrier protein is derived from a JcDNV coat protein. In an alternative embodiment, a recombinant DNA encodes an insecticidal fusion protein that is disclosed herein. In particular, a recombinant DNA can comprise a nucleic acid sequence encoding an insecticidal fusion protein comprising a JcDNV coat protein fused to the N-terminus of an insect toxin via a peptide linker. In some embodiment, the JcDNV coat protein is derived from JcDNV VP4. In some embodiments, the JcDNV coat protein is derived from JcDNV VP1, VP2, or VP3.

Figure 7:
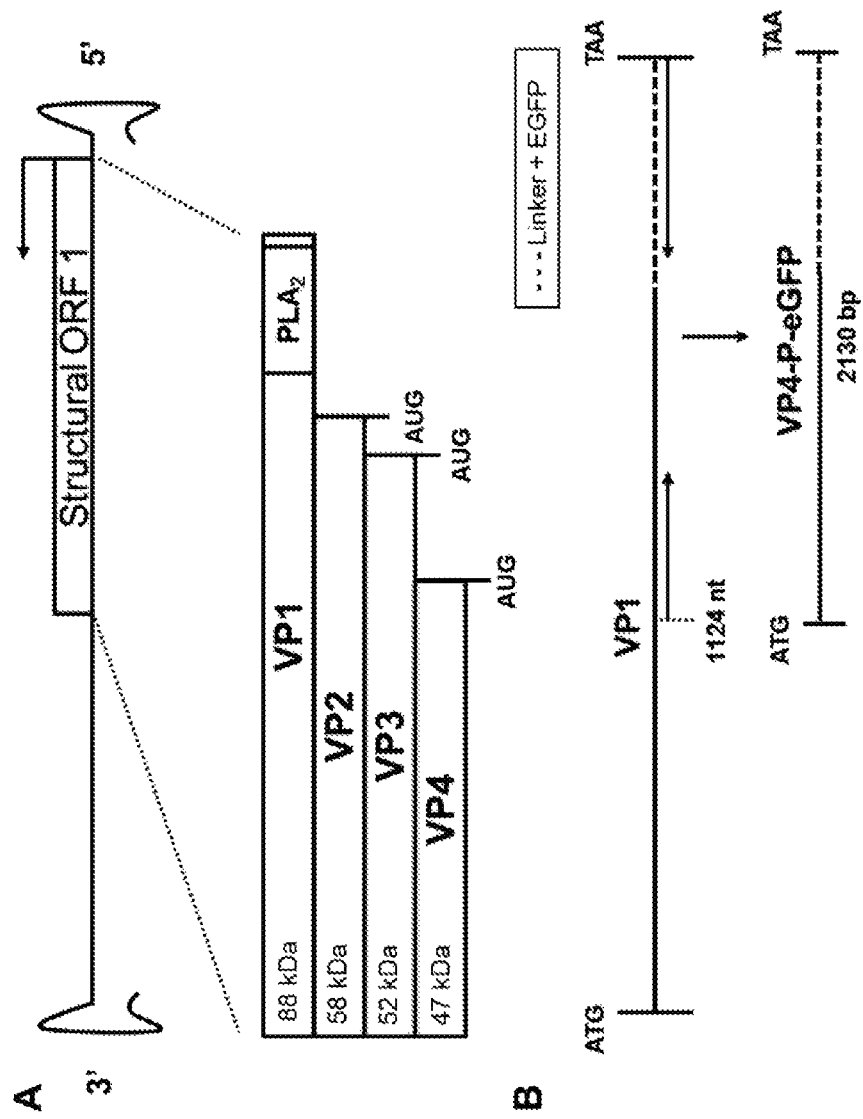
FIG. 7 is a schematic illustrating the construction of a recombinant DNA encoding a JcDNV VP4 fusion protein according to one embodiment of the disclosed invention.

FIG. 7 is a schematic illustrating the construction of a recombinant DNA encoding a JcDNV VP4 fusion protein according to one embodiment. Panel A of FIG. 7 shows the JcDNV open reading frame that encodes the structural protein VP1, which contains a Phospholipase A2 (PLA2) region. VP2, VP3, and VP4 are produced by leaky scanning. The open reading frame encoding the structural proteins of JcDNV results in production of VP1, VP2, VP3, and VP4, which share a common C terminus, but differ in length due to leaky scanning Panel B of FIG. 7 illustrates a recombinant DNA encoding fusion protein VP1-P-eGFP and VP4-P-eGFP. In the recombinant DNA encoding VP1-P-eGFP, a nucleic acid fragment for VP1 is attached to a nucleic acid fragment for eGFP via a nucleic acid fragment for a peptide linker. In the recombinant DNA encoding VP4-P-eGFP, a nucleic acid fragment for VP4 is attached to a nucleic acid fragment for eGFP via a nucleic acid fragment for a peptide linker. The DNA encoding fusion protein VP4-P-eGFP has a sequence set forth in SEQ ID No: 13. The peptide linker can be a proline-rich linker. The VP4-P-eGFP can be amplified by polymerase chain reaction (PCR) using VP1-P-eGFP DNA as a template. The positions of forward and reverse primers are indicated by black arrows. As shown in FIG. 7, the forward primer starts from the 1124th nucleotide of the DNA sequence for VP1. The fusion protein VP4-P-eGFP encoded by the sequence set forth in SEQ ID No: 13 is about 78 kDa. In the DNA sequence encoding VP4-P-eGFP, the nucleic acid sequence for the peptide linker between VP4 and eGFP is set forth in SEQ ID No: 14.

For simplicity of illustration, FIG. 7 only shows the construction of a recombinant DNA encoding VP4-P-eGFP. However, a recombinant DNA disclosed herein can also encode any insecticidal fusion protein disclosed above, such as a fusion protein comprising a JcDNA coat protein attached to an insect toxin via a peptide linker. The toxin can be an insect-specific neurotoxin. Embodiments provide a recombinant DNA encoding fusion protein VP4-P-Hv1a, wherein JcDNV VP4 is fused to the N-terminus of insect toxin Hv1a via a peptide linker such as a proline rich linker.

In an alternative embodiment, a recombinant DNA encodes VP4 attached to a venom derived from an insect predatory species. The insect predatory species can be one or more of scorpions, wasps, predaceous mites, cone snails, anemones, lacewings, and parasitoids. In an alternative embodiment, a toxin can be an arthropod-derived neuropeptides, enzymes, and/or hormone. The toxin can further be proctolin or *Aedes aegypti* trypsin modulating oostatic factor (TMOF). In alternative embodiments, the second peptide or protein that is fused to a JcDNV coat protein can be an *Androctonus australis* Hector insect toxin (AaHIT), as shown in FIG. 5. The AaHIT fused to VP4 can be variants AaHIT1, AaHIT2, AaHIT4, or AaHIT5. The sequence for AaHIT1 is set forth in SEQ ID No: 7; the sequence for AaHIT2 is set forth in SEQ ID No: 8; the sequence for AaHIT4 is set forth in SEQ ID No: 9; the sequence for AaHIT5 is set forth in SEQ ID No: 10. Alternatively, an insecticidal fusion protein can comprise VP4 fused to insect toxin LqHIT2 or LqqIT2 shown in FIG. 6. LqHIT2 is an insect toxin derived from Scorpion, *Leiurus quinquestriatus hebraeus* and has a sequence set forth in SEQ ID No: 11. LqqIT2 is a beta-insect depressant toxin derived from Scorpion, *Leiurus quinquestriatus hebraeus*, and has a sequence set forth in SEQ ID No: 12.

Embodiments further develop a vector comprising and expressing the recombinant DNA disclosed herein. The vector encompasses an expressing cassette for expression of the recombinant proteins described herein. In particular, a vector disclosed herein comprises an expression cassette having a regulatory region operably linked to a nucleic acid sequence encoding a recombinant protein described above. The regulatory region regulates the expression of the recombinant protein in a cell carrying the vector. In some embodiment, the expression of the recombinant is regulated under a regulatory region comprising an inducible promoter, and the recombinant protein is not consistently expressed in a cell carrying the vector but can be induced as needed. In some embodiment, the expression of a recombinant protein described herein in a cell carrying the vector is controlled under a constitutively promoter.

In one embodiment, the vector comprises an expression cassette for expression of a fusion protein comprising a carrier protein fused to a second peptide or protein in an insect. The carrier protein is derived from a JcDNV coat protein. In an alternative embodiment, a vector comprises an expression cassette for expression of a fusion protein comprising VP4 fused to a second peptide or protein via a peptide linker, i.e., a VP4-P-fusion protein.

Figure 8:
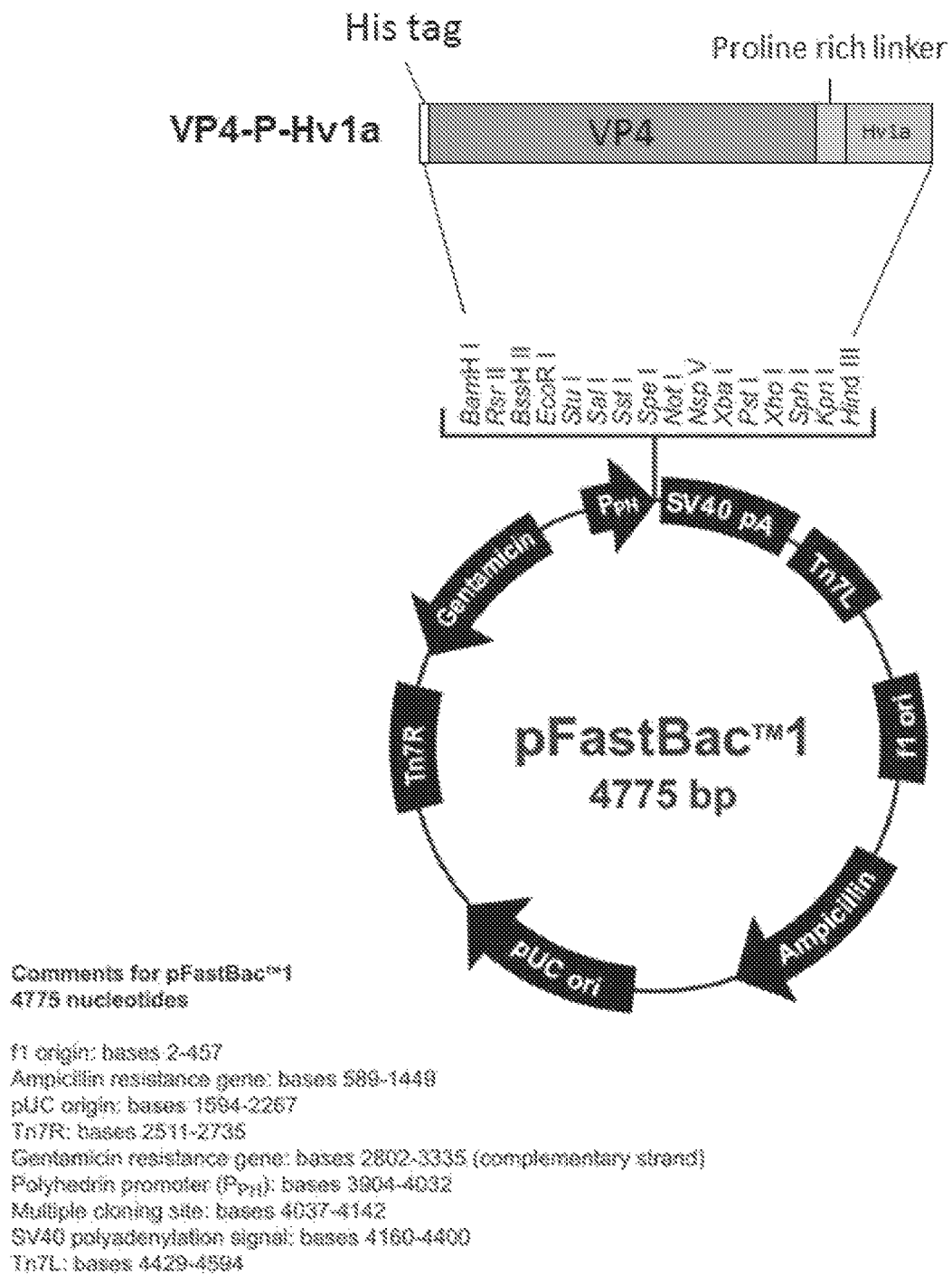
FIG. 8 illustrates an exemplary plasmid vector used for expression of VP4-P-Hv1a in insect cells according to one embodiment of the disclosed invention.

FIG. 8 illustrates an exemplary plasmid vector used for expression of VP4-P-Hv1a in insect cells according to one embodiment of the disclosed invention. In FIG. 8, the sequence encoding a fusion protein comprising His tagged VP4-P-Hv1a is cloned into plasmid pFASTBAC™1 using BamH1 and HindIII restriction sites. However, the restriction sites for cloning a VP4-P-fusion protein into an expression plasmid are not limited to BamH1 and HindIII. Other proper restriction sites shown in FIG. 8 can be utilized to clone a recombinant DNA for a VP4-P-fusion protein into the pFASTBAC™1 plasmid. In FIG. 8, proline rich linker is shown to be used to connect VP4 and Hv1a. However, a VP4-P-fusion protein can comprise VP4 fused to a second peptide or protein via other peptide linker, including other protease-resistant peptide linker. The second peptide can be an insect toxin. The VP4-P-fusion protein can be produced in insect cells through the use of a recombinant baculovirus expression vector (BEVS), constructed from the plasmid pFASTBAC™1 and the BAC-TO-BAC® Baculovirus Expression System (Invitrogen). Large scale production of recombinant fusion protein is feasible using established procedures.

For simplicity of illustration, FIG. 8 only shows a plasmid comprising an expression cassette in which a regulatory region is operably linked to a nucleic acid sequence encoding a His-tagged VP4-P-eGFP. However, a vector disclosed herein can also comprise an expression cassette in which a regulatory region is operably linked to a nucleic acid sequence encoding a fusion protein comprising VP4 fused to an insect toxin disclosed herein. The insect toxin can be an insect-specific neurotoxin. Alternatively, the insect toxin can be an insect-specific toxin that is a venom derived from an insect predatory species. In alternative embodiments, the insect toxin can also be AaHIT1 (SEQ ID No: 7), AaHIT2 (SEQ ID No: 8), AaHIT4 (SEQ ID No: 9), or AaHIT5 (SEQ ID No: 10), as disclosed above. Alternatively, the insect toxin can be insect toxin LqHIT2 with a sequence set forth in SEQ ID No: 11. Alternatively, the insect toxin can be LqqIT2, which has a sequence set forth in SEQ ID No: 12.

According to disclosed embodiments, furthermore, a transformed plant or transgenic plant containing and expressing the disclosed recombinant DNA encoding an insecticidal fusion protein can be engineered. The insecticidal fusion protein can be expressed in phloem tissue, leaf tissue or root tissue of the transgenic plant. the insecticidal fusion protein disclosed herein. Accordingly, disclosed embodiments provide a recombinant DNA comprising a sequence encoding an insecticidal fusion protein disclosed herein and a plant promoter. The sequence encoding an insecticidal fusion protein disclosed herein is operably linked to the plant promoter.

Figure 9:
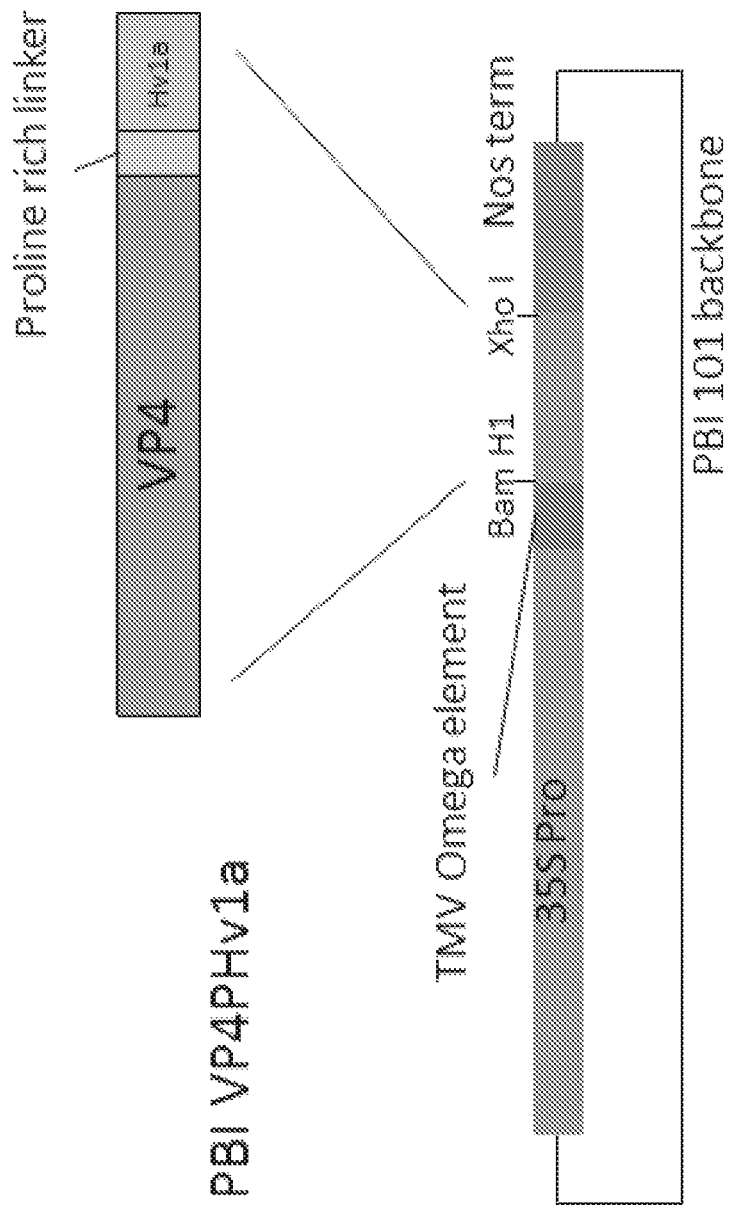
FIG. 9 is a schematic illustrating an exemplary vector for engineering a transgenic plant that expresses of a VP4-P-fusion protein such as VP4-P-Hv1a according to an embodiment of the disclosed invention.

FIG. 9 is a schematic illustrating an exemplary vector for engineering a transgenic plant that expresses of a VP4-P-fusion protein such as VP4-P-Hv1a according to an embodiment of the disclosed invention. As shown in FIG. 9, a nucleic acid sequence encoding an insecticidal fusion protein VP4-P-Hv1a can be cloned into a plant transformation vector pBI101 at particular restriction sites such as Bam H1 and Xho I. the 35S promoter is operably linked to the nucleic acid sequence encoding VP4-P-Hv1a. In an alternative embodiment, the plant promoter is a leaf-specific promoter. The plant promoter can also be a light-activated promoter or a leaf-damage activated promoter. Alternatively, the plant promoter is a constitutive promoter. For production of transgenic plants, constitutive promoters active in most plant tissues such as CAMV35S or FMV35S promoters may be used. *Agrobacterium tumefaciens*—mediated transformation of appropriate crop plants using a binary vector with fusion protein coding sequences inserted between the Cauliflower mosaic virus (CaMV) 35S promoter and Nos terminator of pBITG containing a viral translation enhancer (TMVΩ) downstream of the 35S promoter, can be used for production of transgenic plants expressing an insecticidal fusion protein disclosed herein. The plasmids will be transformed into strain C58C1 of *Agrobacterium tumefaciens* and used for *Agrobacterium*-mediated transformation of the crop plant.

Furthermore, a transformed plant or transgenic plant can be engineered by transforming a plant with a vector comprising an expressing cassette for expressing a disclosed insecticidal fusion protein that comprises an insect-specific toxin. The insect-specific toxin comprised in a disclosed insecticidal fusion protein can be an insect-specific neurotoxin. Furthermore, the insect-specific toxin can be an Arthropod-derived neuropeptides, enzymes, and/or hormone. Alternatively, the insect-specific toxin can be proctolin or *Aedes aegypti* trypsin modulating oostatic factor (TMOF). As a result, transgenic crop plants, or biotech crops, can endogenously express an insecticidal fusion protein comprising a hemocoelic insect-specific toxin attached to VP4 via a peptide linker. The insecticidal fusion protein can be expressed in phloem tissue, leaf tissue, or root tissue of the transgenic plant. The disclosed fusion proteins expressed in the transgenic crop plants are capable of killing a fall armyworm after the insect ingests the fusion proteins produced endogenously in the transgenic crop plants. After being fed to insects, an insecticidal fusion protein produced endogenously in a biotech crop can result in mortality of the insects.

Embodiments further provide a host cell containing the DNA encoding disclosed fusion proteins. The host cell can be a plant cell. The plant cell can be a cell of a crop, an ornamental plant, or a horticultural plant.

Thus, disclosed embodiments provide a method of control pest insect. This method includes feeding a target insect with a food source comprising an insecticidal fusion protein disclosed herein. In one embodiment, the target insect is the fall armyworm, *Spodoptera frugiperda*. After a fall armyworm ingests the food source, the fusion protein will pass across the gut epithelium into the hemocoel of a fall armyworm, allowing the insect-specific toxin in the fusion protein to act in the hemocoel of the target insect and kill the fall armyworm.

Embodiments further provide a method of inhibiting plant damage by a target insect, such as the fall armyworm. The method comprising bringing a food source comprising the insecticidal fusion protein into contact with a target insect under conditions that allow the target insect to ingest the food, whereby the insecticidal fusion protein ingested by the target insect inhibits feeding by or kills the target insect, resulting in reduced plant damage by the target insect. The target insect can be the fall armyworm, *Spodoptera frugiperda*.

The fall armyworm can be inhibited or killed by spraying a composition comprising an insecticidal fusion protein disclosed herein on a plant infected with a fall armyworm. After spraying, the composition comprising an insecticidal fusion protein disclosed herein, such as a VP4 fused to an insect toxin, will be deposited on the surface of the plant leaves or the other parts of the plant. After the fall armyworm ingests plant leaves or the other part of the plant containing the insecticidal fusion protein disclosed herein, the insecticidal fusion protein will pass across the gut epithelium into the hemocoel of the target insect, allowing the insect-specific toxin in the fusion protein to act in the hemocoel of the target insect and kill the target insect. Alternatively, the fall armyworm can be inhibited or killed by feeding on a transgenic plant expressing an insecticidal fusion protein disclosed herein.

Further provided is a method of making a insecticidal fusion toxin comprising a carrier peptide or a carrier protein fused to an insect toxin via a peptide linker. The carrier peptide or carrier protein is able to be transcytosed into the gut cavity. The disclosed method comprises identifying a gut binding peptide for a target insect which is transcytosed into the gut cavity and fusing the gut binding peptide with an insecticidal hemocoelic peptide. The gut binding peptide can be attached to the insecticidal hemocoelic peptide via a peptide linker as anN-terminal extension into the insecticidal hemocoel peptide. The peptide linker can be a protease resistant linker. Further, the insecticidal fusion toxin can be formulated in a composition to apply to a plant or a food resource for feeding a target insect. A recombinant nucleic acid sequence encoding the insecticidal fusion toxin can be further introduced into a plant, allowing the plant to express the insecticidal fusion toxin, thereby providing at least partial protection to the plant from a targeted insect pest.

As disclosed herein, the ability of a JcDNV coat protein to deliver proteins across the gut epithelium into the hemocoel (body cavity) allows a use of toxins that act within the hemocoel (e.g. insect-specific neurotoxins) for insect pest control. The disclosed technology provides an alternative to chemical insecticides. A an insecticidal fusion protein disclosed herein produced in a transgenic crop plant is unlikely to disrupt non-plant eating insects. A VP4/toxin fusion protein also has high specificity. Thus, present disclosure provides a technology that is of great interest to the industry.

Examples of the sequences of VP proteins and hemocoel toxins are provided herein and various analogs and homologs are known and readily available to those of skill in the art form sources such as Genbank. A nucleotide sequence encoding an amino acid sequence corresponding to one of the aforementioned coat protein sequences can be incorporated into the coding sequence of a toxin protein to form a fusion protein, especially where it is incorporated at the N-terminus of the protein (preceded by a Met residue to initiate transcription or where the recited sequence of amino acids is preceded by a signal peptide to allow secretion of the gut-binding fusion protein into the a transgenic plant expressing same.

The practice of the disclosed invention will employ, unless otherwise indicated, conventional techniques of microbiology, recombinant DNA technology and molecular biology and immunology, which are within the skills of the art.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art.

All documents, patents, journal articles and other materials cited in the present application are incorporated herein by reference.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The disclosed invention is further defined in the following Examples. It should be understood that these Examples are given by way of illustration only. From the above discussion and these Examples, one skilled in the art can ascertain the essential characteristics of embodiments of the disclosed invention. Without departing from the spirit and scope thereof, one skilled in the art can make various changes and modifications of the invention to adapt it to various usages and conditions. All publications, including patents and non-patent literature, referred to in this specification are expressly incorporated by reference herein.

EXAMPLES

Example 1

Fusion Protein Transport Across the Gut Epithelium of *S. frugiperda*

This example investigates the transport efficiency of selected fusion proteins across the gut of *Spodoptera frugiperda* (fall armyworm).

The information on transport of proteins from the insect gut into the hemocoel is very limited. In this example, the transport efficiency and mechanisms of selected proteins across the gut of Spodoptera frugiperda (Lepidoptera: Noctuidae) are investigated and the mechanisms of transcytosis[3] for selected proteins that cross the insect gut epithelium are characterized. A greater fundamental understanding of these processes can facilitate future exploitation of this pathway for arthropod pest control and to provide benefit to the crop protection industry.[4] This example examines a pathway that in the long term can be exploited for delivery of insecticidal proteins and peptides having hemocoelic target sites, and thus provides fundamental information about a pathway with potential of exploitation for novel pest control strategies.

Midgut Isolation

Figure 10:
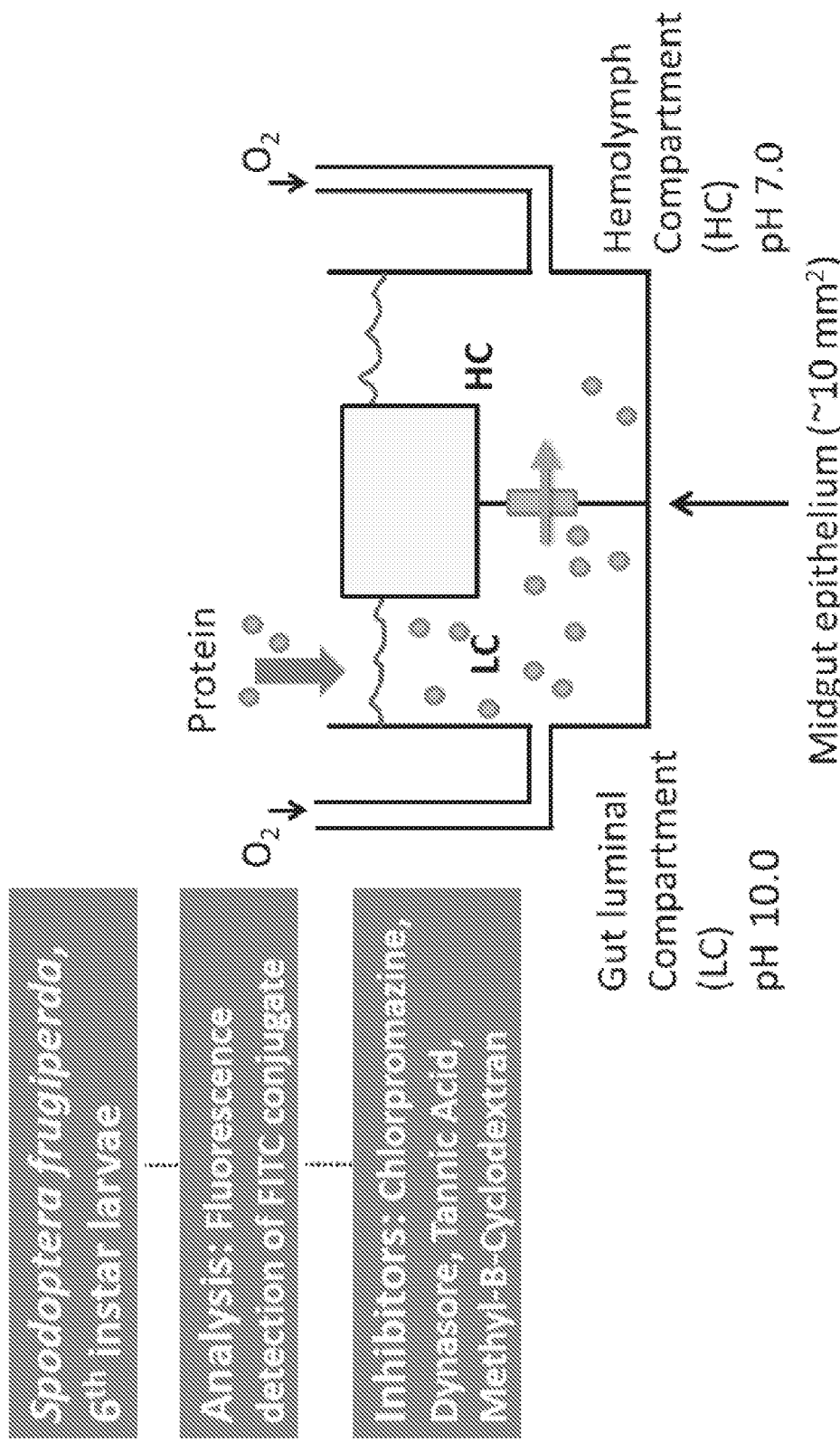
FIG. 10 is a schematic illustrating an experimental approach to examine ex vivo transport of a protein across the gut epithelium of *S. frugiperda* according to one embodiment of the disclosed invention.

FIG. 10 is a schematic illustration showing an experimental approach to examine ex vivo transport of a protein across the gut epithelium of S. frugiperda according to an embodiment of the disclosed invention. The midguts of sixth instars were isolated for chamber studies. Briefly, larvae were sedated on ice for 30 minutes prior to dissection. The midguts at this instar are large enough to mount on sliders without tissue perforation. The dissection was performed in cold Insect Physiological Solution (47 mM KCl, 20.5 mM $MgCl_2$, 20 mM $MgSO_4$, 1 mM $CaCl_2$, 88 mM Sucrose, 4.3 mM $K_2HPO_4$, 1.1 mM $KH_2PO_4$, adjusted to pH 7.5) (Cermenati et al. 2011). The larval gut was exposed by opening the cuticle via a longitudinal incision on the ventro-lateral side. The midgut was isolated excluding the anterior and posterior regions, opened longitudinally and mounted on sliders (0.1 $cm^2$) for transport studies using an Ussing chamber (Physiologic Instruments, Model P2300). Peritrophic membranes were removed for these experiments.

Ussing Chamber Experiments

An Ussing chamber is used to assess the efficiency of movement of selected proteins from the lumenal to the basal side of the S. frugiperda midgut epithelium at 2 days post molt to the sixth instar as described previously.[8, 9] Once mounted into this perfusion apparatus, the movement of proteins added to the luminal side of the midgut to the hemolymph side can be monitored using an appropriate detection assay (i.e. immunodetection or fluorescence for labeled proteins). The advantage of this approach is that the efficiency of protein movement can readily be quantified.

The midgut epithelium mounted in the Ussing chamber was perfused with 2.5-3 ml of luminal buffer (5 mM CaCl2, 24 mM MgSO4, 20 mM potassium gluconate, 190 mM sucrose, 5 mM CAPS, pH 10.0) in the lumen compartment and 2.5-3 ml of hemolymph buffer (5 mM CaCl2, 24 mM MgSO4, 20 mM potassium gluconate, 190 mM sucrose, 5 mM Tris, pH 7.0) in the hemocoel compartment. A continuous supply of oxygen was provided to both chambers, and experiments were performed at 27° C. protected from light. FITC-Albumin (15 uM and 3 uM), eGFP (3 uM) and VP4-P-eGFP (3 uM) were added to the lumen chamber. FITC-albumin was run through a gel matrix that removed unbound FITC, immediately before experimentation. Samples of 100 μl were collected at 10, 20, 30, 60, and 120 minutes. Total chamber volumes were collected after the 120 minute time point, and analyzed via standard western immunoblotting procedures to determine integrity of proteins in the lumen and hemocoel chamber.

Time course samples were analyzed using a fluorescence microplate reader (excitation wavelength 495 nm, emission wavelength 525 nm). Standard curves with known concentrations of the test protein in hemolymph buffer were used with each 96-well plate to calculate the amount of protein transported across the epithelium. The protein flux was expressed as $pmol/cm^2$. Rates of transport were calculated using the time course samples and expressed as $pmol/cm^2/2$ h. Flux experiments were repeated with a minimum of 6 midguts per protein, and inhibitor experiments with a minimum of 4 midguts per treatment. Mean±standard error is provided for flux and rates of each protein.

Experiments were run for no longer than 2 hours to ensure that tissue remained viable in the chamber during the course of each experiment. Sections of paraffin-embedded tissue taken from chamber experiments displayed healthy epithelium morphology with no apparent loss of integrity.

This example further addresses whether the same mechanisms are employed for transcytosis of selected proteins by insects in different orders, with the pea aphid, Acyrthosiphum pisum (Hemiptera) and the Colorado potato beetle, Leptinotarsa decemlineata (Coleoptera) as representative species.

Test for Movement of Fusion Proteins into the Hemocoel

Fifth instar larvae (n=30) will be starved for 3 hours and then droplet fed on a high concentration of purified recombinant VP4-P-eGFP or GFP. Hemolymph will be collected from an incision in the proleg at 30 min, 1 hr and 2 hr post feeding. Pericardial cells that line the dorsal aorta will also be dissected to assess whether VP4-P-eGFP is removed from the hemocoel as observed previously.[22] Pericardial cells will be observed for fluorescence, and western blot used for both pericardial cells and hemolymph samples for detection of fusion proteins using GFP antiserum.

Production of VP4 Fusion Protein

A VP4-P-fusion protein, can be produced in insect cells (Sf9) using the BAC-TO-BAC® Baculovirus Expression System (Invitrogen). In an example, the fusion protein VP4-P-eGFP with a C-terminal 6×His tag, as shown in FIG. 4, is expressed in insect cells (Sf9) using the BAC-TO-BAC® Baculovirus Expression System (Invitrogen) and further purified. As VP4-P-eGFP produced in Sf9 cells was insoluble, the fusion protein was denatured as described previously[23] and then refolded by slow dialysis against decreasing concentrations of urea. Refolded VP4-P-eGFP was concentrated using PEG20 and SLIDE-A-LYZER™ dialysis cassettes (ThermoFisher Scientific) prior to use.

Transport of VP4-P-Fusion Protein Across the S. frugiperda Gut

A fusion protein VP4-P-Hv1a shown in FIG. 4 is also expressed in insect cells using the baculovirus expression system and purified. The VP4-P-eGFP used in the example is estimated to be 80 to 90% pure. Add this in the body later. Larvae of S. frugiperda is droplet fed on a solution of fusion protein, or control fusion protein (VP4-P-Hv1a) which has two amino acid residues modified (N27A, R35A) which render the toxin inactive.[24] Following droplet feeding, larvae is transferred to artificial diet and maintained in a growth chamber. Mortality is scored every 12 hours. Larvae are observed for symptoms, in particular paralysis induced by Hv1a. Bioassays is conducted with different doses of fusion protein with three biological and three technical replicates and appropriate statistical analyses to assess the lethal dose of the VP4-P-Hv1a.

Figure 11:
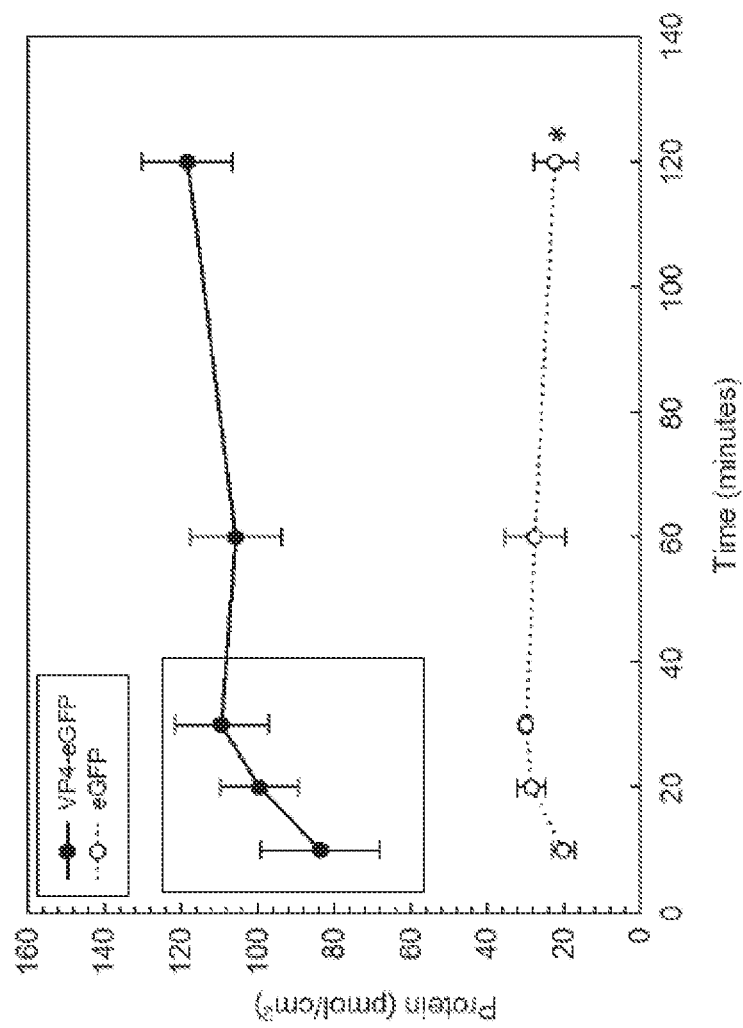
FIG. 11 is a graph illustrating transport of VP4-P-eGFP across the *S. frugiperda* gut epithelium according to one embodiment of the disclosed invention.

FIG. 11 is a graph showing transport of VP4-P-eGFP across the S. frugiperda gut epithelium according to one embodiment of the disclosed invention. In FIG. 11, *Mean±s.e. is significantly different from VP4-eGFP (p=0.016). As shown in FIG. 11, VP4 of densovirus crosses S. frugiperda midgut rapidly. VP4 mediates transport of eGFP across the gut epithelium. Transport rapidly occurs within 30 minutes of introduction of the fusion protein into the gut side of the Ussing Chamber.

Figure 12:
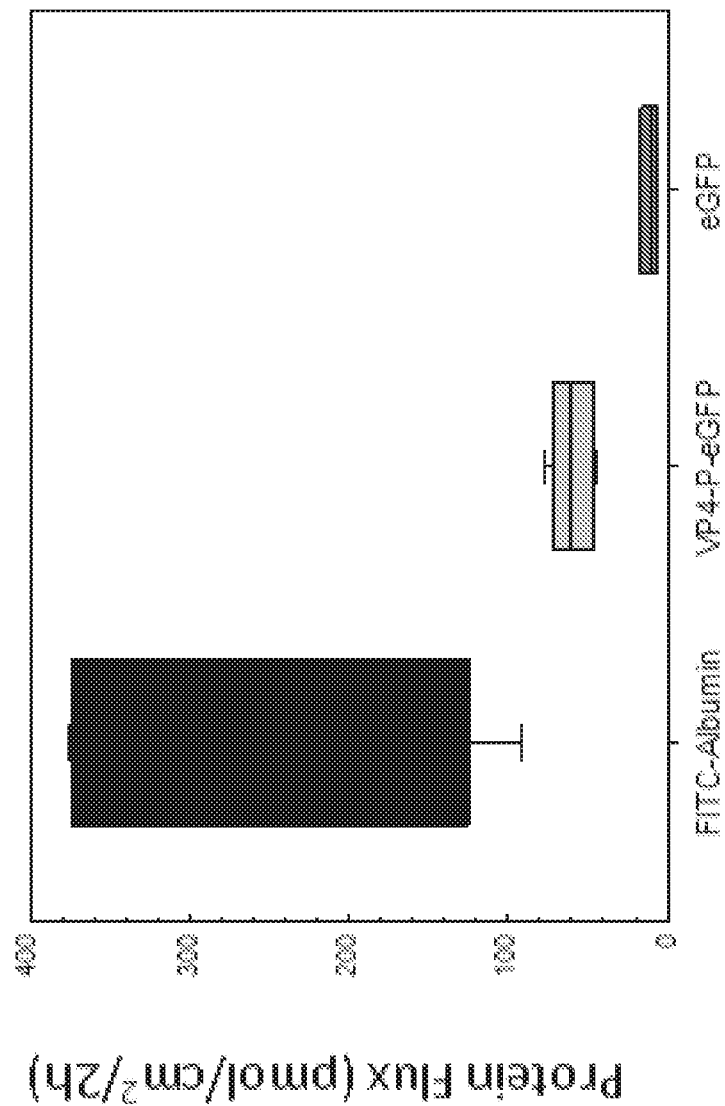
FIG. 12 is a graph illustrating a comparison of the amount of VP4-P-eGFP transported across the epithelium compared to eGFP alone, and to albumin according to one embodiment of the disclosed invention.

FIG. 12 is a graph illustrating comparison of amount of VP4-P-eGFP transported across the epithelium compared to eGFP alone, and to albumin. In FIG. 12, *Mean±s.e. is significantly different to VP4-P-eGFP (p=0.016). FIG. 12 shows that compared with albumin and dGFP, VP4-P-eGFP transports with controlled efficiency across the gut epithelium of *S. frugiperda*.

Figure 13:
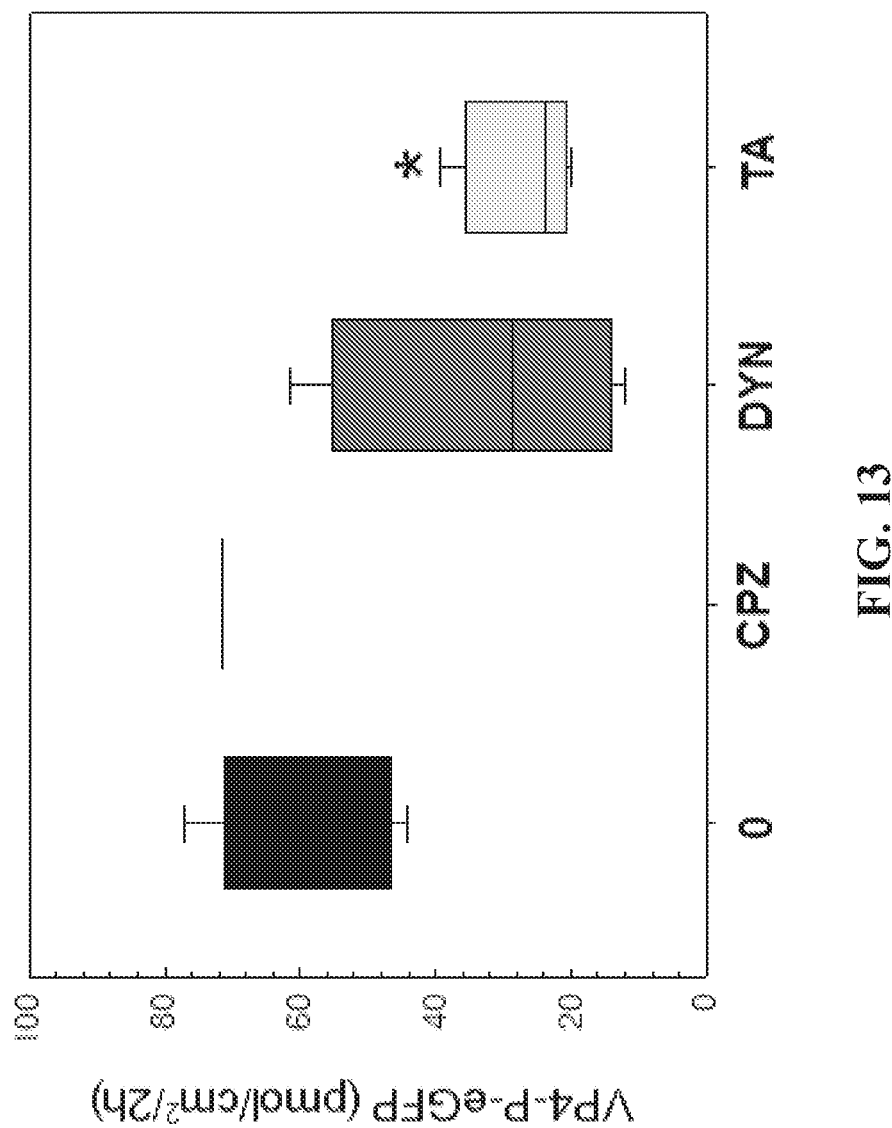
FIG. 13 is a graph illustrating that transport of VP4-P-eGFP is inhibited by addition of tannic acid according to one embodiment of the disclosed invention.

FIG. 13 is a graph illustrating transport of VP4-P-eGFP being inhibited by addition of tannic acid (TA) according to one embodiment of the disclosed invention.

Example 2

Techniques for Engineering the Disclosed Fusion Proteins and Plants that Express the Disclosed Fusion Proteins The engineering of disclosed fusion proteins and plants that express the disclosed fusion proteins employs genetic engineering and plant transformation techniques known in the art. This example generally describes such techniques.

Plant Transformation Methods

Numerous methods for introducing foreign genes into plants are known and can be used to insert a fusion toxin polynucleotide into a plant host, including biological and physical plant transformation protocols. See, e.g., Miki et al., "Procedure for Introducing Foreign DNA into Plants," in *Methods in Plant Molecular Biology and Biotechnology*, Glick and Thompson, eds., CRC Press, Inc., Boca Raton, pp. 67-88 (1993). The methods chosen vary with the host plant, and include chemical transfection methods such as calcium phosphate, microorganism-mediated gene transfer such as *Agrobacterium* (Horsch et al., *Science* 227:1229-31 (1985)), electroporation, micro-injection, and biolistic bombardment.

Expression cassettes and vectors and in vitro culture methods for plant cell or tissue transformation and regeneration of plants are known and available. See, e.g., Gruber et al., "Vectors for Plant Transformation," in *Methods in Plant Molecular Biology and Biotechnology*, supra, pp. 89-119.

The isolated polynucleotides or polypeptides may be introduced into the plant by one or more techniques typically used for direct delivery into cells. Such protocols may vary depending on the type of organism, cell, plant or plant cell, i.e. monocot or dicot, targeted for gene modification. Suitable methods of transforming plant cells include microinjection (Crossway, et al., (1986) *Biotechniques* 4:320-334; and U.S. Pat. No. 6,300,543), electroporation (Riggs, et al., (1986) *Proc. Natl. Acad. Sci. USA* 83:5602-5606, direct gene transfer (Paszkowski et al., (1984) *EMBO J.* 3:2717-2722), and ballistic particle acceleration (see, for example, Sanford, et al., U.S. Pat. No. 4,945,050; WO 91/10725; and McCabe, et al., (1988) *Biotechnology* 6:923-926). Also see, Tomes, et al., "Direct DNA Transfer into Intact Plant Cells Via Microprojectile Bombardment." pp. 197-213 in *Plant Cell, Tissue and Organ Culture, Fundamental Methods*. eds. O. L. Gamborg & G. C. Phillips. Springer-Verlag Berlin Heidelberg N.Y., 1995; U.S. Pat. No. 5,736,369 (meristem); Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); WO 91/10725 (maize); Klein, et al., (1988) *Plant Physiol.* 91:440-444 (maize); Fromm, et al., (1990) *Biotechnology* 8:833-839; and Gordon-Kamm, et al., (1990) *Plant Cell* 2:603-618 (maize); Hooydaas-Van Slogteren & Hooykaas (1984) *Nature* (London) 311:763-764; Bytebierm, et al., (1987) *Proc. Natl. Acad. Sci. USA* 84:5345-5349 (Liliaceae); De Wet, et al., (1985) *In The Experimental Manipulation of Ovule Tissues*, ed. G. P. Chapman, et al., pp. 197-209. Longman, N.Y. (pollen); Kaeppler, et al., (1990) *Plant Cell Reports* 9:415-418; and Kaeppler, et al., (1992) *Theor. Appl. Genet.* 84:560-566 (whisker-mediated transformation); U.S. Pat. No. 5,693,512 (sonication); D'Halluin, et al., (1992) *Plant Cell* 4:1495-1505 (electroporation); Li, et al., (1993) *Plant Cell Reports* 12:250-255; and Christou and Ford, (1995) *Annals of Botany* 75:407-413 (rice); Osjoda, et al., (1996) *Nature Biotech.* 14:745-750; *Agrobacterium* mediated maize transformation (U.S. Pat. No. 5,981,840); silicon carbide whisker methods (Frame, et al., (1994) *Plant J.* 6:941-948); laser methods (Guo, et al., (1995) *Physiologia Plantarum* 93:19-24); sonication methods (Bao, et al., (1997) *Ultrasound in Medicine & Biology* 23:953-959; Finer and Finer, (2000) *Lett Appl Microbiol.* 30:406-10; Amoah, et al., (2001) *J Exp Bot* 52:1135-42); polyethylene glycol methods (Krens, et al., (1982) *Nature* 296:72-77); protoplasts of monocot and dicot cells can be transformed using electroporation (Fromm, et al., (1985) *Proc. Natl. Acad. Sci. USA* 82:5824-5828) and microinjection (Crossway, et al., (1986) *Mol. Gen. Genet.* 202:179-185); all of which are herein incorporated by reference.

*Agrobacterium*-Mediated Transformation

The most widely utilized method for introducing an expression vector into plants is based on the natural transformation system of *Agrobacterium. A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) *Crit. Rev. Plant Sci.* 10:1. Descriptions of the *Agrobacterium* vector systems and methods for *Agrobacterium*-mediated gene transfer are provided in Gruber, et al., supra; Miki, et al., supra; and Moloney, et al., (1989) *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. Pat. No. 913,914, filed Oct. 1, 1986, as referenced in U.S. Pat. No. 5,262,306, issued Nov. 16, 1993; and Simpson, et al., (1986) *Plant Mol. Biol.* 6:403-15 (also referenced in the '306 patent); all incorporated by reference in their entirety.

Once constructed, these plasmids can be placed into *A. rhizogenes* or *A. tumefaciens* and these vectors used to transform cells of plant species, which are ordinarily susceptible to *Fusarium* or *Alternaria* infection. Several other transgenic plants are also contemplated by the disclosed invention including but not limited to soybean, corn, sorghum, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for transformation. Most dicotyledonous plants, some gymnosperms, and a few monocotyledonous plants (e.g., certain members of the Liliales and Arales) are susceptible to infection with *A. tumefaciens*. *A. rhizogenes* also has a wide host range, embracing most dicots and some gymnosperms, which includes members of the Leguminosae, Compositae, and Chenopodiaceae. Monocot plants can now be transformed with some success. European Patent Application No. 604 662 A1 discloses a method for transforming monocots using *Agrobacterium*. European Application No. 672 752 A1 discloses a method for transforming monocots with *Agrobacterium* using the scutellum of immature embryos. Ishida, et al., discuss a method for transforming maize by exposing immature embryos to *A. tumefaciens* (*Nature Biotechnology* 14:745-50 (1996)).

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) *Theor. Appl. Genet.* 69:235-40; U.S. Pat. No. 4,658,082; Simpson, et al., supra; and U.S. Pat. Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

Despite the fact that the host range for *Agrobacterium*-mediated transformation is broad, some major cereal crop species and gymnosperms have generally been recalcitrant to this mode of gene transfer, even though some success has recently been achieved in rice (Hiei, et al., (1994) *The Plant Journal* 6:271-82). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206; and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731; and Christou, et al., (1987) *Proc. Natl. Acad. Sci. USA* 84:3962. Direct uptake of DNA into protoplasts using $CaCl_2$ precipitation, polyvinyl alcohol, or poly-L-ornithine has also been reported. See, e.g., Hain, et al., (1985) *Mol. Gen. Genet.* 199:161; and Draper, et al., (1982) *Plant Cell Physiol.* 23:451.

Electroporation of protoplasts and whole cells and tissues has also been described. See, e.g., Donn, et al., (1990) *Abstracts of the VIIth Intl. Congress on Plant Cell and Tissue Culture IAPTC*, A2-38, p. 53; D'Halluin, et al., (1992) *Plant Cell* 4:1495-505; and Spencer, et al., (1994) *Plant Mol. Biol.* 24:51-61.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

In certain embodiments the nucleic acid sequences of the disclosed invention can be used in combination ("stacked") with other polynucleotide sequences of interest in order to create plants with a desired phenotype. The combinations generated can include multiple copies of any one or more of the polynucleotides of interest. The polynucleotides of the disclosed invention may be stacked with any gene or combination of genes to produce plants with a variety of desired trait combinations, including but not limited to traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,049); barley high lysine (Williamson, et al., (1987) *Eur. J. Biochem.* 165:99-106; and WO 98/20122); and high methionine proteins (Pedersen, et al., (1986) *J. Biol. Chem.* 261:6279; Kirihara, et al., (1988) *Gene* 71:359; and Musumura, et al., (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the disclosed invention can also be stacked with traits desirable for insect, disease or herbicide resistance (e.g., *Bacillus thuringiensis* toxic proteins (U.S. Pat. Nos. 5,366,892; 5,747,450; 5,736,514; 5,723,756; 5,593,881; Geiser, et al., (1986) *Gene* 48:109); lectins (Van Damme, et al., (1994) *Plant Mol. Biol.* 24:825); fumonisin detoxification genes (U.S. Pat. No. 5,792,931); avirulence and disease resistance genes (Jones, et al., (1994) *Science* 266:789; Martin, et al., (1993) *Science* 262:1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert, et al., (1988) *J. Bacteriol.* 170:5837-5847) facilitate expression of polyhydroxyalkanoates (PHAs)), the disclosures of which are herein incorporated by reference. One could also combine the polynucleotides of the disclosed invention with polynucleotides affecting agronomic traits such as male sterility (e.g., see U.S. Pat. No. 5,583,210), stalk strength, flowering time, or transformation technology traits such as cell cycle regulation or gene targeting (e.g., WO 99/61619; WO 00/17364; WO 99/25821), the disclosures of which are herein incorporated by reference.

Methods of Use for Insect Toxin Fusion Protein Polynucleotides, Expression Cassettes, and Additional Polynucleotides The nucleotides, expression cassettes and methods disclosed herein are useful in modulating expression of any heterologous nucleotide sequence in a host plant in order to vary the phenotype of a plant. Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Nucleic Acids

The disclosed invention provides, inter alia, isolated nucleic acids of RNA, DNA, homologs, paralogs and orthologs and/or chimeras thereof, comprising a fusion insect toxin polynucleotide. This includes naturally occurring as well as synthetic variants and homologs of the sequences.

Sequences homologous, i.e., that share significant sequence identity or similarity, to those provided herein derived from maize, rice or from other plants of choice, are also an aspect of the invention. Homologous sequences can be derived from any plant including monocots and dicots and in particular agriculturally important plant species, including but not limited to, crops such as soybean, wheat, corn (maize), potato, cotton, rape, oilseed rape (including canola), sunflower, alfalfa, clover, sugarcane, and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, tomatillo, watermelon, rosaceous fruits (such as apple, peach, pear, cherry and plum) and vegetable brassicas (such as broccoli, cabbage, cauliflower, Brussels sprouts, and kohlrabi). Other crops, including fruits and vegetables, whose phenotype can be changed and which comprise homologous sequences include barley; rye; millet; sorghum; currant; avocado; citrus fruits such as oranges, lemons, grapefruit and tangerines, artichoke, cherries; nuts such as the walnut and peanut; endive; leek; roots such as arrowroot, beet, cassava, turnip, radish, yam, and sweet potato; and beans. The homologous sequences may also be derived from woody species, such pine, poplar and eucalyptus, or mint or other labiates. In addition, homologous sequences may be derived from plants that are evolutionarily-related to crop plants, but which may not have yet been used as crop plants. Examples include deadly nightshade (*Atropa belladona*), related to tomato; jimson weed (*Datura strommium*), related to peyote; and teosinte (*Zea* species), related to corn (maize).

Orthologs and Paralogs

Homologous sequences as described above can comprise orthologous or paralogous sequences. Several different methods are known by those of skill in the art for identifying and defining these functionally homologous sequences. Three general methods for defining orthologs and paralogs are described; an ortholog, paralog or homolog may be identified by one or more of the methods described below.

Orthologs and paralogs are evolutionarily related genes that have similar sequence and similar functions. Orthologs are structurally related genes in different species that are derived by a speciation event. Paralogs are structurally related genes within a single species that are derived by a duplication event.

Within a single plant species, gene duplication may result in two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL (Thompson et al. (1994) Nucleic Acids Res. 22: 4673-4680; Higgins et al. (1996) Methods Enzymol. 266: 383-402). Groups of similar genes can also be identified with pair-wise BLAST analysis (Feng and Doolittle (1987) J. Mol. Evol. 25: 351-360).

Orthologous genes from different organisms have highly conserved functions, and very often essentially identical functions (Lee et al. (2002) Genome Res. 12: 493-502; Remm et al. (2001) J. Mol. Biol. 314: 1041-1052). Paralogous genes, which have diverged through gene duplication, may retain similar functions of the encoded proteins. In such cases, paralogs can be used interchangeably with respect to certain embodiments of the instant invention (for example, transgenic expression of a coding sequence).

Variant Nucleotide Sequences in the Non-Coding Regions

The fusion insect toxin protein nucleotide sequences are used to generate variant nucleotide sequences having the nucleotide sequence of the 5'-untranslated region, 3'-untranslated region, or promoter region that is approximately 70%, 75%, and 80%, 85%, 90% and 95% identical to the original nucleotide sequence. These variants are then associated with natural variation in the germplasm for component traits. The associated variants are used as marker haplotypes to select for the desirable traits.

Variant Amino Acid Sequences of Polypeptides

Variant amino acid sequences of the fusion insect toxin peptides are generated. In this example, one amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using a protein alignment, an appropriate amino acid can be changed. Once the targeted amino acid is identified, the procedure outlined herein is followed. Variants having about 70%, 75%, 80%, 85%, 90% and 95% nucleic acid sequence identity are generated using this method. These variants are then associated with natural variation in the germplasm for component traits related to NUE. The associated variants are used as marker haplotypes to select for the desirable traits.

The disclosed invention also includes polynucleotides optimized for expression in different organisms. For example, for expression of the polynucleotide in a particular plant, the sequence can be altered to account for specific codon.

Construction of Nucleic Acids

The isolated nucleic acids of the disclosed invention can be made using (a) standard recombinant methods, (b) synthetic techniques, or combinations thereof. In some embodiments, the polynucleotides of the disclosed invention will be cloned, amplified, or otherwise constructed from a fungus or bacteria.

The nucleic acids may conveniently comprise sequences in addition to a polynucleotide of the disclosed invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the disclosed invention. For example, a hexa-histidine marker sequence provides a convenient means to purify the proteins of the disclosed invention. The nucleic acid of the disclosed invention— excluding the polynucleotide sequence—is optionally a vector, adapter, or peptide linker for cloning and/or expression of a polynucleotide of the disclosed invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the disclosed invention less the length of its polynucleotide of the disclosed invention is less than 20 kilobase pairs, often less than 15 kb, and frequently less than 10 kb. Use of cloning vectors, expression vectors, adapters, and peptide linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pGEM, pSK+/−, pGEX, pSPORTI and II, pOPRSVI CAT, pOPI3 CAT, pXT1, pSG5, pPbac, pMbac, pMC1neo, pOG44, pOG45, pFRTβGAL, pNEOβGAL, pRS403, pRS404, pRS405, pRS406, pRS413, pRS414, pRS415, pRS416, lambda MOSSlox, and lambda MOSElox. Optional vectors for the disclosed invention, include but are not limited to, lambda ZAP II, and pGEX. For a description of various nucleic acids see, e.g., Stratagene Cloning Systems, Catalogs 1995, 1996, 1997 (La Jolla, Calif.); and, Amersham Life Sciences, Inc, Catalog '97 (Arlington Heights, Ill.).

Synthetic Methods for Constructing Nucleic Acids

The isolated nucleic acids of the disclosed invention can also be prepared by direct chemical synthesis by methods such as the phosphotriester method of Narang, et al., (1979) *Meth. Enzymol.* 68:90-9; the phosphodiester method of Brown, et al., (1979) *Meth. Enzymol.* 68:109-51; the diethylphosphoramidite method of Beaucage, et al., (1981) *Tetra. Letts.* 22(20):1859-62; the solid phase phosphoramidite triester method described by Beaucage et al., supra, e.g., using an automated synthesizer, e.g., as described in Needham-VanDevanter, et al., (1984) *Nucleic Acids Res.* 12:6159-68; and, the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 5<G>7 methyl GpppG RNA cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the disclosed invention provides 5' and/or 3' UTR regions for modulation of translation of heterologous coding sequences.

Further, the polypeptide-encoding segments of the polynucleotides of the disclosed invention can be modified to alter codon usage. Altered codon usage can be employed to alter translational efficiency and/or to optimize the coding sequence for expression in a desired host or to optimize the codon usage in a heterologous sequence for expression in rice. Codon usage in the coding regions of the polynucleotides of the disclosed invention can be analyzed statistically using commercially available software packages such as "Codon Preference" available from the University of Wisconsin Genetics Computer Group. See, Devereaux, et al., (1984) *Nucleic Acids Res.* 12:387-395); or MacVector 4.1 (Eastman Kodak Co., New Haven, Conn.). Thus, the disclosed invention provides a codon usage frequency characteristic of the coding region of at least one of the polynucleotides of the disclosed invention. The number of polynucleotides (3 nucleotides per amino acid) that can be used to determine a codon usage frequency can be any integer from 3 to the number of polynucleotides of the disclosed invention as provided herein. Optionally, the polynucleotides will be full-length sequences. An exemplary number of sequences for statistical analysis can be at least 1, 5, 10, 20, 50 or 100.

Sequence Shuffling

The disclosed invention provides methods for sequence shuffling using polynucleotides of the disclosed invention, and compositions resulting therefrom. Sequence shuffling is described in PCT publication No. 96/19256. See also, Zhang, et al., (1997) *Proc. Natl. Acad. Sci. USA* 94:4504-9; and Zhao, et al., (1998) *Nature Biotech* 16:258-61. Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an altered $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Recombinant Expression Cassettes

The present disclosure further provides recombinant expression cassettes comprising a nucleic acid of the present disclosure, preferably designed for reducing the activity of fusion insect toxin protein. A nucleic acid sequence coding for the desired polynucleotide of the present disclosure, for example a cDNA or a genomic sequence encoding a polypeptide long enough to code for an active protein of the present disclosure, can be used to construct a recombinant expression cassette which can be introduced into the desired host cell. A recombinant expression cassette will typically comprise a polynucleotide of the present disclosure operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site and/or a polyadenylation signal.

Promoters, Terminators, Introns

A plant promoter fragment can be employed which will direct expression of a polynucleotide of the present disclosure in essentially all tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of *Agrobacterium tumefaciens*, the Smas promoter, the cinnamyl alcohol dehydrogenase promoter (U.S. Pat. No. 5,683,439), the Nos promoter, the RuBisCO promoter, the GRP1-8 promoter, the 35S promoter from cauliflower mosaic virus (CaMV), as described in Odell, et al., (1985) Nature 313:810-2; rice actin (McElroy, et al., (1990) Plant Cell 163-171); ubiquitin (Christensen, et al., (1992) Plant Mol. Biol. 12:619-632 and Christensen, et al., (1992) Plant Mol. Biol. 18:675-89); pEMU (Last, et al., (1991) Theor. Appl. Genet. 81:581-8); MAS (Velten, et al., (1984) EMBO J. 3:2723-30) and maize H3 histone (Lepetit, et al., (1992) Mol. Gen. Genet. 231:276-85 and Atanassvoa, et al., (1992) Plant Journal 2(3):291-300); ALS promoter, as described in PCT Application Number WO 1996/30530 and other transcription initiation regions from various plant genes known to those of skill. For the present disclosure ubiquitin is the preferred promoter for expression in monocot plants.

Alternatively, the plant promoter can direct expression of a polynucleotide of the present disclosure in a specific tissue or may be otherwise under more precise environmental or developmental control. Such promoters may be "inducible" promoters. Environmental conditions that may affect transcription by inducible promoters include pathogen attack, anaerobic conditions or the presence of light. Examples of inducible promoters are the Adh1 promoter, which is inducible by hypoxia or cold stress, the Hsp70 promoter, which is inducible by heat stress and the PPDK promoter, which is inducible by light. Diurnal promoters that are active at different times during the circadian rhythm are also known (US Patent Application Publication Number 2011/0167517, incorporated herein by reference).

Examples of promoters under developmental control include promoters that initiate transcription only, or preferentially, in certain tissues, such as leaves, roots, fruit, seeds or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'-end of a polynucleotide coding region. The polyadenylation region can be derived from a variety of plant genes, or from T-DNA. The 3' end sequence to be added can be derived from, for example, the nopaline synthase or octopine synthase genes or alternatively from another plant gene or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan, et al., (1983) Nucleic Acids Res. 12:369-85); the potato proteinase inhibitor II (PINII) gene (Keil, et al., (1986) Nucleic Acids Res. 14:5641-50 and An, et al., (1989) Plant Cell 1:115-22) and the CaMV 19S gene (Mogen, et al., (1990) Plant Cell 2:1261-72).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, (1988) Mol. Cell Biol. 8:4395-4405; Callis, et al., (1987) Genes Dev. 1:1183-200). Such intron enhancement of gene expression is typically greatest when placed near the 5' end of the transcription unit. Use of maize introns Adh1-S intron 1, 2 and 6, the Bronze-1 intron are known in the art. See generally, The Maize Handbook, Chapter 116, Freeling and Walbot, eds., Springer, New York (1994).

Signal Peptide Sequences

Plant signal sequences, including, but not limited to, signal-peptide encoding DNA/RNA sequences which target proteins to the extracellular matrix of the plant cell (Dratewka-Kos, et al., (1989) J. Biol. Chem. 264:4896-900), such as the *Nicotiana plumbaginifolia* extension gene (DeLoose, et al., (1991) Gene 99:95-100); signal peptides which target proteins to the vacuole, such as the sweet potato sporamin gene (Matsuka, et al., (1991) Proc. Natl. Acad. Sci. USA 88:834) and the barley lectin gene (Wilkins, et al., (1990) Plant Cell, 2:301-13); signal peptides which cause proteins to be secreted, such as that of PRIb (Lind, et al., (1992) Plant Mol. Biol. 18:47-53) or the barley alpha amylase (BAA)

(Rahmatullah, et al., (1989) Plant Mol. Biol. 12:119) or signal peptides which target proteins to the plastids such as that of rapeseed enoyl-Acp reductase (Verwaert, et al., (1994) Plant Mol. Biol. 26:189-202) are useful in the disclosure.

Markers

The vector comprising the sequences from a polynucleotide of the present disclosure will typically comprise a marker gene, which confers a selectable phenotype on plant cells. The selectable marker gene may encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance. Also useful are genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Constructs described herein may comprise a polynucleotide of interest encoding a reporter or marker product. Examples of suitable reporter polynucleotides known in the art can be found in, for example, Jefferson, et al., (1991) in Plant Molecular Biology Manual, ed. Gelvin, et al., (Kluwer Academic Publishers), pp. 1-33; DeWet, et al. (1987) Mol. Cell. Biol. 7:725-737; Goff, et al., (1990) EMBO J. 9:2517-2522; Kain, et al., (1995) Bio Techniques 19:650-655 and Chiu, et al., (1996) Current Biology 6:325-330. In certain embodiments, the polynucleotide of interest encodes a selectable reporter. These can include polynucleotides that confer antibiotic resistance or resistance to herbicides. Examples of suitable selectable marker polynucleotides include, but are not limited to, genes encoding resistance to chloramphenicol, methotrexate, hygromycin, streptomycin, spectinomycin, bleomycin, sulfonamide, bromoxynil, glyphosate and phosphinothricin.

In some embodiments, the expression cassettes disclosed herein comprise a polynucleotide of interest encoding scorable or screenable markers, where presence of the polynucleotide produces a measurable product. Examples include a .beta.-glucuronidase, or uidA gene (GUS), which encodes an enzyme for which various chromogenic substrates are known (for example, U.S. Pat. Nos. 5,268,463 and 5,599,670); chloramphenicol acetyl transferase and alkaline phosphatase. Other screenable markers include the anthocyanin/flavonoid polynucleotides including, for example, a R-locus polynucleotide, which encodes a product that regulates the production of anthocyanin pigments (red color) in plant tissues, the genes which control biosynthesis of flavonoid pigments, such as the maize C1 and C2, the B gene, the p1 gene and the bronze locus genes, among others. Further examples of suitable markers encoded by polynucleotides of interest include the cyan fluorescent protein (CYP) gene, the yellow fluorescent protein gene, a lux gene, which encodes a luciferase, the presence of which may be detected using, for example, X-ray film, scintillation counting, fluorescent spectrophotometry, low-light video cameras, photon counting cameras or multiwell luminometry, a green fluorescent protein (GFP) and DsRed2 (Clontechniques, 2001) where plant cells transformed with the marker gene are red in color, and thus visually selectable. Additional examples include a p-lactamase gene encoding an enzyme for which various chromogenic substrates are known (e.g., PADAC, a chromogenic cephalosporin), a xylE gene encoding a catechol dioxygenase that can convert chromogenic catechols, an .alpha.-amylase gene and a tyrosinase gene encoding an enzyme capable of oxidizing tyrosine to DOPA and dopaquinone, which in turn condenses to form the easily detectable compound melanin.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as .beta.-galactosidase and fluorescent proteins such as green fluorescent protein (GFP) (Su, et al., (2004) Biotechnol Bioeng 85:610-9 and Fetter, et al., (2004) Plant Cell 16:215-28), cyan florescent protein (CYP) (Bolte, et al., (2004) J. Cell Science 117:943-54 and Kato, et al., (2002) Plant Physiol 129:913-42) and yellow florescent protein (PhiYFP™ from Evrogen, see, Bolte, et al., (2004) J. Cell Science 117:943-54). For additional selectable markers, see generally, Yarranton, (1992) Curr. Opin. Biotech. 3:506-511; Christopherson, et al., (1992) Proc. Natl. Acad. Sci. USA 89:6314-6318; Yao, et al., (1992) Cell 71:63-72; Reznikoff, (1992) Mol. Microbiol. 6:2419-2422; Barkley, et al., (1980) in The Operon, pp. 177-220; Hu, et al., (1987) Cell 48:555-566; Brown, et al., (1987) Cell 49:603-612; Figge, et al., (1988) Cell 52:713-722; Deuschle, et al., (1989) Proc. Natl. Acad. Aci. USA 86:5400-5404; Fuerst, et al., (1989) Proc. Natl. Acad. Sci. USA 86:2549-2553; Deuschle, et al., (1990) Science 248:480-483; Gossen, (1993) Ph.D. Thesis, University of Heidelberg; Reines, et al., (1993) Proc. Natl. Acad. Sci. USA 90:1917-1921; Labow, et al., (1990) Mol. Cell. Biol. 10:3343-3356; Zambretti, et al., (1992) Proc. Natl. Acad. Sci. USA 89:3952-3956; Bairn, et al., (1991) Proc. Natl. Acad. Sci. USA 88:5072-5076; Wyborski, et al., (1991) Nucleic Acids Res. 19:4647-4653; Hillenand-Wissman, (1989) Topics Mol. Struc. Biol. 10:143-162; Degenkolb, et al., (1991) Antimicrob. Agents Chemother. 35:1591-1595; Kleinschnidt, et al., (1988) Biochemistry 27:1094-1104; Bonin, (1993) Ph.D. Thesis, University of Heidelberg; Gossen, et al., (1992) Proc. Natl. Acad. Sci. USA 89:5547-5551; Oliva, et al., (1992) Antimicrob. Agents Chemother. 36:913-919; Hlavka, et al., (1985) Handbook of Experimental Pharmacology, Vol. 78 (Springer-Verlag, Berlin); Gill, et al., (1988) Nature 334:721-724. Such disclosures are herein incorporated by reference. The above list of selectable marker genes is not meant to be limiting. Any selectable marker gene can be used in the compositions and methods disclosed herein.

Typical vectors useful for expression of genes in higher plants are well known in the art and include vectors derived from the tumor-inducing (Ti) plasmid of *Agrobacterium tumefaciens* described by Rogers, et al., (1987) Meth. Enzymol. 153:253-77. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) Gene 61:1-11 and Berger, et al., (1989) Proc. Natl. Acad. Sci. USA, 86:8402-6.

Another useful vector herein is plasmid pBI101.2 that is available from CLONTECH Laboratories, Inc. (Palo Alto, Calif.).

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198: 1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the disclosed invention are available using *Bacillus* sp. and *Salmonella* (Palva, et al., (1983) *Gene* 22:229-35; Mosbach, et al., (1983) *Nature* 302:543-5). The pGEX-4T-1 plasmid vector from Pharmacia is the preferred *E. coli* expression vector for the disclosed invention.

Expression in Eukaryotes

A variety of eukaryotic expression systems such as yeast, insect cell lines, plant and mammalian cells, are known to those of skill in the art. As explained briefly below, the disclosed invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, et al., (1982) *Methods in Yeast Genetics*, Cold Spring Harbor Laboratory is a well-recognized work describing the various methods available to produce the protein in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the disclosed invention, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins of the disclosed invention can also be ligated to various expression vectors for use in transfecting cell cultures of, for instance, mammalian, insect, or plant origin. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HAS tk promoter or pgk (phosphoglycerate kinase) promoter), an enhancer (Queen, et al., (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the disclosed invention are available, for instance, from the American Type Culture Collection Catalogue of Cell Lines and Hybridomas ($7^{th}$ ed., 1992).

Appropriate vectors for expressing proteins of the disclosed invention in insect cells are usually derived from the SF9 baculovirus. Suitable insect cell lines include mosquito larvae, silkworm, armyworm, moth, and *Drosophila* cell lines such as a Schneider cell line (see, e.g., Schneider, (1987) *J. Embryol. Exp. Morphol.* 27:353-65).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague et al., *J. Virol.* 45:773-81 (1983)). Additionally, gene sequences to control replication in the host cell may be incorporated into the vector such as those found in bovine papilloma virus type-vectors (Saveria-Campo, "Bovine Papilloma Virus DNA a Eukaryotic Cloning Vector," in *DNA Cloning: A Practical Approach*, vol. II, Glover, ed., IRL Press, Arlington, Va., pp. 213-38 (1985)).

In addition, the fusion inset toxin gene placed in the appropriate plant expression vector can be used to transform plant cells. The polypeptide can then be isolated from plant callus or the transformed cells can be used to regenerate transgenic plants. Such transgenic plants can be harvested, and the appropriate tissues (seed or leaves, for example) can be subjected to large scale protein extraction and purification techniques.

Additional Modifications to Plants

Additional, agronomically important traits such as oil, starch, and protein content can be genetically altered in addition to using traditional breeding methods and are contemplated herein along with the fusion insect toxin protein. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885, 802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson, et al., (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley, et al., (1989)

Proceedings of the World Congress on Vegetable Protein Utilization in Human Foods and Animal Feedstuffs, ed. Applewhite (American Oil Chemists Society, Champaign, Ill.), pp. 497-502; herein incorporated by reference); corn (Pedersen, et al., (1986) J. Biol. Chem. 261:6279; Kirihara, et al., (1988) Gene 71:359; both of which are herein incorporated by reference); and rice (Musumura, et al., (1989) Plant Mol. Biol. 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, Bacillus thuringiensis toxic protein genes (U.S. Pat. Nos. 5,366,892; 5,747,450; 5,736,514; 5,723,756; 5,593,881; and Geiser, et al., (1986) Gene 48:109); and the like.

Genes encoding disease resistance traits include detoxification genes, such as against fumonosin (U.S. Pat. No. 5,792,931); avirulence (avr) and disease resistance (R) genes (Jones, et al., (1994) Science 266:789; Martin, et al., (1993) Science 262:1432; and Mindrinos, et al., (1994) Cell 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see, Schubert, et al., (1988) J. Bacteriol. 170:5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

Hybrid Seed Production

Hybrid seed production requires elimination or inactivation of pollen produced by the female parent. Incomplete removal or inactivation of the pollen provides the potential for selfing, raising the risk that inadvertently self-pollinated seed will unintentionally be harvested and packaged with hybrid seed. Once the seed is planted, the selfed plants can be identified and selected; the selfed plants are genetically equivalent to the female inbred line used to produce the hybrid. Typically, the selfed plants are identified and selected based on their decreased vigor relative to the hybrid plants. For example, female selfed plants of e are identified by their less vigorous appearance for vegetative and/or reproductive characteristics, including shorter plant height, small ear size, ear and kernel shape, cob color or other characteristics. Selfed lines also can be identified using molecular marker analyses (see, e.g., Smith and Wych, (1995) Seed Sci. Technol. 14:1-8). Using such methods, the homozygosity of the self-pollinated line can be verified by analyzing allelic composition at various loci in the genome.

Because hybrid plants are important and valuable field crops, plant breeders are continually working to develop high-yielding hybrids that are agronomically sound based on stable inbred lines. The availability of such hybrids allows a maximum amount of crop to be produced with the inputs used, while minimizing susceptibility to pests and environmental stresses. To accomplish this goal, the plant breeder must develop superior inbred parental lines for producing hybrids by identifying and selecting genetically unique individuals that occur in a segregating population. The present disclosure contributes to this goal, for example by providing plants that, when crossed, generate male sterile progeny, which can be used as female parental plants for generating hybrid plants.

Use in Breeding Methods

The insect toxin fusion protein plants of the disclosure may be used in a plant breeding program. The goal of plant breeding is to combine, in a single variety or hybrid, various desirable traits. For field crops, these traits may include, for example, resistance to diseases and insects, tolerance to heat and drought, tolerance to chilling or freezing, reduced time to crop maturity, greater yield and better agronomic quality. With mechanical harvesting of many crops, uniformity of plant characteristics such as germination and stand establishment, growth rate, maturity and plant and ear height is desirable. Traditional plant breeding is an important tool in developing new and improved commercial crops. This disclosure encompasses methods for producing a plant by crossing a first parent plant with a second parent plant wherein one or both of the parent plants is a transformed plant displaying a phenotype as described herein.

Plant breeding techniques known in the art and used in a plant breeding program include, but are not limited to, recurrent selection, bulk selection, mass selection, backcrossing, pedigree breeding, open pollination breeding, restriction fragment length polymorphism enhanced selection, genetic marker enhanced selection, doubled haploids and transformation. Often combinations of these techniques are used.

The development of hybrids in a plant breeding program requires, in general, the development of homozygous inbred lines, the crossing of these lines and the evaluation of the crosses. There are many analytical methods available to evaluate the result of a cross. The oldest and most traditional method of analysis is the observation of phenotypic traits. Alternatively, the genotype of a plant can be examined.

A genetic trait which has been engineered into a particular plant using gene editing or transformation techniques can be moved into another line using traditional breeding techniques that are well known in the plant breeding arts. For example, a backcrossing approach is commonly used to move a modified plant to an elite inbred line and the resulting progeny would then comprise the modification. Also, if an inbred line was used for the transformation or editing, then those plants could be crossed to a different inbred in order to produce a hybrid plant. As used herein, "crossing" can refer to a simple X by Y cross or the process of backcrossing, depending on the context.

The development of a hybrid in a plant breeding program involves three steps: (1) the selection of plants from various germplasm pools for initial breeding crosses; (2) the selfing of the selected plants from the breeding crosses for several generations to produce a series of inbred lines, which, while different from each other, breed true and are highly homozygous and (3) crossing the selected inbred lines with different inbred lines to produce the hybrids. During the inbreeding process, the vigor of the lines decreases. Vigor is restored when two different inbred lines are crossed to produce the hybrid. An important consequence of the homozygosity and homogeneity of the inbred lines is that the hybrid created by crossing a defined pair of inbreds will always be the same. Once the inbreds that give a superior hybrid have been identified, the hybrid seed can be reproduced indefinitely as long as the homogeneity of the inbred parents is maintained.

Transgenic plants of the present disclosure may be used to produce, e.g., a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B) times (C×D). A three-way cross hybrid is produced from three inbred lines where two of the inbred lines are crossed (A×B) and then the resulting F1 hybrid is crossed with the third inbred (A×B)×C. Much of the hybrid vigor and uniformity exhibited by F1 hybrids is lost in the next generation (F2). Consequently, seed produced by hybrids is consumed rather than planted.

Having described the many embodiments of the disclosed invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

It is intended that the invention not be limited to the particular embodiment disclosed herein contemplated for carrying out this invention, but that the invention will include all embodiments falling within the scope of the claims.

REFERENCES

The following references are referred to above and are incorporated herein by reference:

1. Sanahuja, G., et al. (2011) *Bacillus thuringiensis*: a century of research, development and commercial applications. Plant Biotech J 9, 283-300.
2. Windley, M. J., et al. (2012) Spider-venom peptides as bioinsecticides. Toxins (Basel) 4, 191-227.
3. Tuma, P. L. and Hubbard, A. L. (2003) Transcytosis: Crossing cellular barriers. Physiol Rev 83, 871-932.
4. Bonning, B. C. and Chougule, N. P. (2014) Delivery of intrahemocoelic peptides for insect pest management. Trends Biotechnol, 32(2), 91-98.
5. Fitches, E., et al. (2001) In vitro and in vivo binding of snowdrop (*Galanthus nivalis* agglutinin; GNA) and jackbean (*Canavalia ensiformis*; Con A) lectins within tomato moth (*Lacanobia oleracea*) larvae; mechanisms of insecticidal action. J Insect Physiol 47, 777-787.
6. Jeffers, L. A. and Roe, R. M. (2008) The movement of proteins across the insect and tick digestive system. J Insect Physiol 54, 319-332.
7. Dahlman, D. L., et al. (2003) A teratocyte gene from a parasitic wasp that is associated with inhibition of insect growth and development inhibits host protein synthesis. Insect Mol Biol 12, 527-534.
8. Wang, Y., et al. (2013) Densovirus crosses the insect midgut by transcytosis and disturbs the barrier epithelial function. J Virol., 87 (22), 12380-12391.
9. Fiandra, L., et al. (2009) The intestinal barrier in lepidopteran larvae: permeability of the peritrophic membrane and of the midgut epithelium to two biologically active peptides. J Insect Physiol 55, 10-18.
10. Casartelli, M., et al. (2008) A megalin-like receptor is involved in protein endocytosis in the midgut of an insect (*Bombyx mori*, Lepidoptera). Am J Physiol Regul Integr Comp Physiol 295, R1290-1300.
11. Cermenati, G. C. P., et al. (2007) A morphological and functional characterization of *Bombyx mori* larval midgut cells in culture. Invertebr. Survival 4, 119-126.
12. Cermenati, G., et al. (2011) The CPP Tat enhances eGFP cell internalization and transepithelial transport by the larval midgut of *Bombyx mori* (Lepidoptera, Bombycidae). J Insect Physiol 57, 1689-1697.
13. Wolfsberger, M., et al. (1987) Preparation and partial characterization of amino acid transporting brush border membrane vesicles from the larval midgut of the cabbage butterfly (*Pieris brassicae*). Comp. Biochem. Phyisol. 86, 301-308
14. Bruemmer A1, Scholari F, Lopez-Ferber M, Conway J F, Hewat E A. Structure of an insect parvovirus (*Junonia coenia* Densovirus) determined by cryo-electron microscopy. J Mol Biol. 2005 Apr. 8; 347(4):791-801.
15. Ffrench-Constant, R. H. et al. (2007) Insecticidal toxins from *Photorhabdus* bacteria and their potential use in agriculture. Toxicon 49, 436-451
16. Primor N and Zlotkin E., Penetrability of proteins through the digestive system of *Sarcophaga falculata* blowfly. Biochim Biophys Acta. 1980 Jan. 3; 627(1):82-90.
17. Stone G M, Murphy L, Miller B G., Hormone receptor levels and hormone, RNA and protein metabolism in the genital tract during the oestrous cycle in the ewe. Theriogenology. 1976 December; 6(6):617.
18. Gade, G. (2004). Regulation of intermediary metabolism and water balance of insects by neuropeptides. Annual review of entomology 49: 93-113.
19. Schoofs et al. (1991) Schoofs L, Janssen I, Veelaert D, Vanden Broeck J, Tobe S S, De Loof A. Ecdysiostatins and allatostatins in *Schistocerca gregaria*. Ann N Y Acad Sci. 1998 May 15; 839:301-5.
20. Casartelli, M., et al. (2005) Absorption of albumin by the midgut of a lepidopteran larva. J. Insect Physiology 51, 933-940.
21. AK Mukherjee et al., Orally active acaricidal peptide toxins from spider venom. Toxicon 2006; 47:182-7.

22. Bonning B C et al. Toxin delivery by the coat protein of an aphid-vectored plant virus provides plant resistance to aphids. Nat Biotechnol, 2014 January; 32(1):102-5.
23. O'Shaughnessy, L.; Doyle; S. Purification of proteins from baculovirus-infected insect cells. In *Protein Chromatography: Methods and Protocols*; Walls, D.; Loughran, S., Eds.; Humana Press: 2011.
24. Tedford, H. W.; Fletcher, J. I.; King, G. F. Functional significance of the beta hairpin in the insecticidal neurotoxin omega-atracotoxin-Hv1a. *J Biol Chem* 2001, 276, 26568-26576.
25. Ffrench-Constant R H and Bass C, Does resistance really carry a fitness cost? Curr Opin Insect Sci. 2017 June; 21:39-46.
26. Dumas, B., M. Jourdan, A. M. Pascaud, and M. Bergoin. 1992. Complete nucleotide sequence of the cloned infectious genome of *Junonia coenia* densovirus reveals an organization unique among parvoviruses. Virology 191: 202-222.
27. Adly Abd-Alla, et al., NS-3 Protein of the *Junonia coenia* Densovirus Is Essential for Viral DNA Replication in an Ld 652 Cell Line and *Spodoptera littoralis* Larvae. J Virol. 2004 January; 78(2): 790-797.

All documents, patents, journal articles and other materials cited in the present application are incorporated herein by reference.

While the disclosed invention has been disclosed with references to certain embodiments, numerous modification, alterations, and changes to the described embodiments are possible without departing from the sphere and scope of the disclosed invention, as defined in the appended claims. Accordingly, it is intended that the disclosed invention not be limited to the described embodiments, but that it has the full scope defined by the language of the following claims, and equivalents thereof.

What is claimed is:

1. A fusion protein comprising a carrier protein attached to a second peptide via a peptide linker, wherein the carrier protein is a *Junonia coenia* densovirus (JcDNV) coat protein.

2. The fusion protein of claim 1, wherein the JcDNV coat protein is VP4 that has an amino acid sequence SEQ ID No: 2.

3. The fusion protein of claim 1, wherein the JcDNV coat protein is VP1 that has an amino acid sequence SEQ ID No: 1.

4. The fusion protein according to claim 1, wherein the peptide linker is a protease-resistant linker.

5. The fusion protein according to claim 1, wherein the second peptide comprises an insect toxin.

6. The fusion protein according to claim 5, wherein the insect toxin is Hv1a that has an amino acid sequence SEQ ID NO: 6.

7. The fusion protein according to claim 6, wherein the fusion protein comprises VP4 attached to the N-terminus of insect toxin Hv1Ia through a proline rich linker, and wherein the peptide linker has an amino acid sequence SEQ ID No: 4.

8. The fusion protein according to claim 5, wherein the insect toxin comprises an arthropod-derived insecticidal peptide.

9. The fusion protein according to claim 5, wherein the insect toxin is an *Androctonus australis* Hector insect toxin (AaHIT) or a Scorpion, *Leiurus quinquestriatus hebraeus* toxin.

10. A composition comprising a fusion protein according to claim 1.

11. The composition according to claim 10, wherein the composition is in a spray formulation.

12. A method of controlling insect pests comprising feeding a fall army worm, *Spodoptera frugiperda*, with a food source comprising a fusion protein comprising a JcDNV coat protein attached to an insect toxin via a peptide linker, thereby allowing the fusion protein to pass across the gut epithelium of the fall armyworm and act within the hemocoel of the fall armyworm after the fusion protein is ingested by the fall armyworm.

13. The method according to claim 12, wherein the food source is a plant sprayed with a composition comprising the fusion protein, and whereby the fusion protein is deposited on a surface of the plant.

* * * * *